United States Patent
Goodman et al.

(10) Patent No.: US 10,478,501 B2
(45) Date of Patent: Nov. 19, 2019

(54) METHOD OF TREATING DISORDERS USING A PHARMACEUTICAL COMPOSITION OF OLIGOPEPTIDES

(75) Inventors: Simon Goodman, Griesheim (DE); Christiane Amendt, Muehltal / Trautheim (DE); Marcus Eber, Nauheim (DE)

(73) Assignee: Merck Patent GmbH, Darmstadt (DE)

( * ) Notice: Subject to any disclaimer, the term of this patent is extended or adjusted under 35 U.S.C. 154(b) by 1170 days.

(21) Appl. No.: 14/122,956

(22) PCT Filed: May 16, 2012

(86) PCT No.: PCT/EP2012/002117
§ 371 (c)(1),
(2), (4) Date: Jan. 23, 2014

(87) PCT Pub. No.: WO2012/167870
PCT Pub. Date: Dec. 13, 2012

(65) Prior Publication Data
US 2016/0228551 A1    Aug. 11, 2016

Related U.S. Application Data

(60) Provisional application No. 61/494,988, filed on Jun. 9, 2011.

(51) Int. Cl.
| | | |
|---|---|---|
| *A61K 38/12* | (2006.01) | |
| *A61K 47/14* | (2017.01) | |
| *A61K 9/00* | (2006.01) | |
| *A61K 9/10* | (2006.01) | |
| *A61K 47/44* | (2017.01) | |
| *A61K 9/08* | (2006.01) | |
| *A61K 9/16* | (2006.01) | |
| *A61K 39/395* | (2006.01) | |
| *A61N 5/10* | (2006.01) | |
| *A61K 9/14* | (2006.01) | |
| *A61K 39/00* | (2006.01) | |

(52) U.S. Cl.
CPC ............ *A61K 47/14* (2013.01); *A61K 9/0019* (2013.01); *A61K 9/08* (2013.01); *A61K 9/10* (2013.01); *A61K 9/1611* (2013.01); *A61K 9/1617* (2013.01); *A61K 9/1664* (2013.01); *A61K 9/1682* (2013.01); *A61K 38/12* (2013.01); *A61K 39/39558* (2013.01); *A61K 47/44* (2013.01); *A61N 5/1077* (2013.01); *A61K 9/14* (2013.01); *A61K 2039/54* (2013.01); *A61K 2039/545* (2013.01)

(58) Field of Classification Search
None
See application file for complete search history.

(56) References Cited

U.S. PATENT DOCUMENTS 6,001,961 A * 12/1999 Jonczyk ................... C07K 7/64
530/317

FOREIGN PATENT DOCUMENTS

| WO | 2009/040071 A2 | 4/2009 | |
|---|---|---|---|
| WO | WO 2009040071 A2 * | 4/2009 | ............. A61K 38/07 |
| WO | 2010/133367 A2 | 11/2010 | |
| WO | 2011/069629 A2 | 6/2011 | |
| WO | WO-2011069629 A2 * | 6/2011 | ........... A61K 9/0019 |

OTHER PUBLICATIONS

Reardon et al. "Randomized Phase II Study of Cilengitide, an Integrin-Targeting Arginine-Glycine-Aspartic Acid Peptide, in Recurrent Glioblastoma Multiforme", Journal of Clinical Oncology, 2008, 5610-5617.*
Barajas et al. "Differentiation of Recurrent Glioblastoma Multiforme from Radiation Necrosis after External Beam Radiation Therapy with Dynamic Susceptibility-weighted Contrast-enhanced Perfusion MR Imaging", Radiology, 2009; pp. 486-496.*
Birbilis et al., "Spinal Metastasis of Glioblastoma Multiforme: An Uncommon Suspect?", Spine, 2010, E264-E269.*
Reardon et al., "Randomized Phase II Study ofCilengitide, an Integrin-Targeting Arginine-Glycine-Aspartic Acid Peptide, in Recurrent Glioblastoma Multiforme", Journal of Clinical Oncology, 2008, 5610-5617 (Year: 2008).*
Barajas et al.. "Differentiation of Recurrent Glioblastoma Multiforme from Radiation Necrosis after External Beam Radiation Therapy with Dynamic Susceptibility-weighted Contrast-enhanced Perfusion MR Imaging", Radiology, 2009; pp. 486-496 (Year: 2009).*
Birbilis et al., "Spinal Metastasis of Glioblastoma Multiforme: An Uncommon Suspect?", Spine, 2010, E264-E269 (Year: 2010).*
Duong LT et al; Front Biosci (1998) 3:d757-68.
Carlo Mas-Moruno; Anti-Cancer Agents in Medicinal Chemistry (2010) 753-768.
Guise TA; Genes Dev (2009) 23:2117-2123.
Schwartz MA; Trends Cell Biol (2001) 11:466-70.
Varner JA, Brooks PC, Cheresh DA; Cell Adhes Commun (1995) 3:367-74.
Hynes RO; Cell (2002) 110:673-87.
Max R, Gerritsen, et al.; Int J Cancer (1997) 71(3):320-4.
Nemeth JA et al.; Cancer Investigation (2007) 25:632-46.
Mulder WJ et al.; Angiogenesis(2009) 12:17-24.
Nemeth JA et al.; Clinical & Experiental Metastasis (2003) 20:413-20.

(Continued)

*Primary Examiner* — Lianko G Garyu
(74) *Attorney, Agent, or Firm* — Grüneberg and Myers PLLC

(57) ABSTRACT

The present invention relates to a pharmaceutical composition of oligopeptides, preferably cyclic oligopeptides, said composition further comprising one or more lipophilic and/or amphiphilic compounds, in the presence or absence of water as the main ingredients, the use of the lipophilic and/or amphiphilic compounds for making pharmaceutical compositions of said oligopeptides, and methods of making said pharmaceutical composition.

25 Claims, 21 Drawing Sheets

Specification includes a Sequence Listing.

(56) References Cited

OTHER PUBLICATIONS

Pecheur I et al.: Faseb J ( 2002) 16:1266-8.
Sloan EK et al.; Breast Cancer Research (2006) 8:R20.
Silvestri I et al.; Int J Cancer (2002) 102(6):562-71.
Inoue M, Ross FP et al; Endocrinology (2000) 141:284-90.
Reardon DA et al; Expert Opin Investig Drugs (2008) 17(8):1225-35.
Dechantsreiter MA et al; J Med Chem (1999) 42:3033-40.
Nisato RE et al; Angiogenesis (2003) 6:105-19.
Patsenker E et al; Hepatology (2009) 50:1501-11.
Xiong JP et al; Science (2002) 296:151-5.
Buerkle MA et al; Br J Cancer (2002) 86:788-95.
Reardon DA et al; J Clin Oncol (2008) 26:5610-7.
Strieth S et al; Int J Cancer (2006) 119:423-31.
Hodivala-Dilke K; Curr Opin Cell Biol (2008) 20:514-9.
Taverna D et al; Proc Natl Acad Sci U S A (2004) 101:763-8.
Bäuerle T et al; Eur J Radio (2010) 73:280-7.
Bäuerle T et al; Neoplasia (2008) 10:511-20.
Mitjans F et al; J Cell Sci (1995) 108 ( Pt 8):2825-38.
Cheresh DA et al; J Biol Chem (1987) 262:17703-11.
Weinacker A et al; J Biol Chem (1994) 269:6940-8.
Bäuerle T et al; Int J Cancer (2005) 115(2):177-86.
Yamada S et al; Neurosurgery (2006) 59(6):1304-12.
Brix G et al; J Comput Assist Tomogr (1991) 15(4):621-8.
Harms JF et al; Clin Exp Metastasis (2004) 21:119-28.
Zhao Y et al; Cancer Res (2007) 67:5821-30.
Eliceiri BP et al; J Cell Biol (2002) 157:149-60.
Nakamura I et al; J Bone Miner Metab (2007) 25:337-44.
Andersen TL et al; Am J Pathol (2009) 174(1):239-47.
Hamaoka T et al; J Clin Oncol (2004) 22(14):2942-53.
Lai CF et al; J Bone Miner Res (2005) 20(2):330-40.
Bäuerle T et al; Int J Oncol (2006) 28(3):573-83.
Karadag A et al; Journal of the National Cancer Institute (2004) 96(12):956-65.
Mitjans F et al; Int J Cancer (2000) 87:716-23.
MacDonald TJ et al; Neurosurgery (2001) 48(1):151-7.
Chen Q et al; Clin Exp Metastasis (2008) 25:139-48.
Reynolds AR et al; Nat Med (2009) 15(4):392-400.
Brooks PC et al; Cell (1994) 79:1157-64.
Alghisi GC et al; PLoS One (2009) 4(2):e4449.
Abdollahi A et al; Clin Cancer Res (2005) 11:6270-9.
Mikkelsen T et al; Int J Cancer (2009) 124(11):2719-27.
Albert JM et al; Int J Radiat Oncol Biol Phys (2006) 65:1536-43.
Reynolds LE et al; Nat Med (2002) 8(1):27-34.

* cited by examiner

Single crystal structure of form A1

Figs. 13A, B. Quantification of histological analysis. Values of fractional mean area stained for smooth Muscle actin (SMA) and collagen IV (Col. IV) are expressed as percent total area examined (A), While the blood vessel diameters are presented as mean values in μm (B). Error bars, SEM; *, $p<0.05$; **, $p<0.01$.

Cilengitide with radiation in U251 MG xenograft orthotopic brain model in nude rat Cell death response amplified by cilengitide in presence of radiotherapy Representative MRI sections of rat brains implanted with U251 and treated.

Kaplan Meir Survival Plot. U251Control (n=10), Cilengitide alone (n=4), RT alone (n=8) Cilengitide + RT (n=9)

Figure 20
Cilengitide in combination with Herceptin in Her2+ breast cancer model BT474
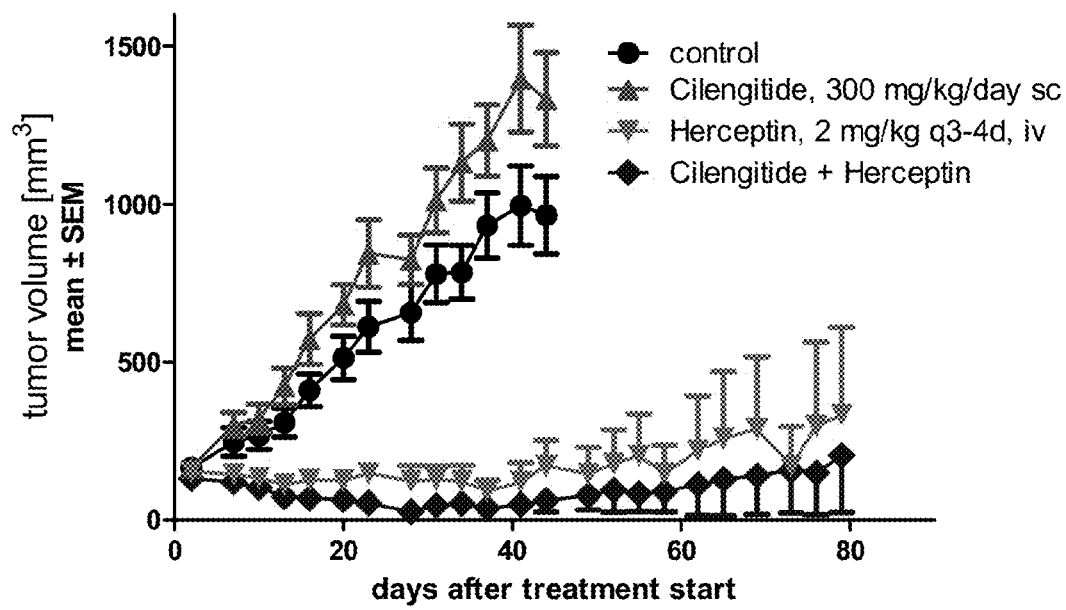
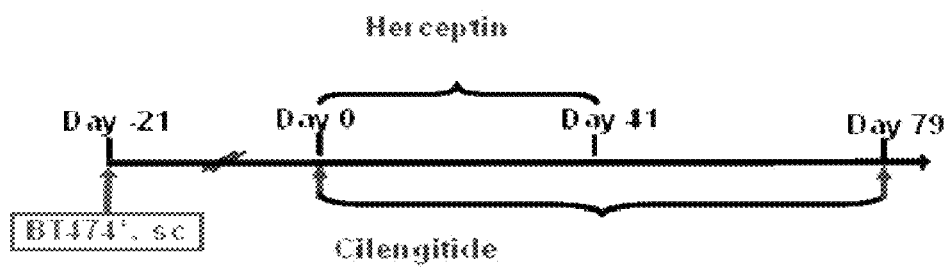
| | Progressive disease | Stable disease | Partial Response | Complete Regression |
|---|---|---|---|---|
| Herceptin | 1 | 3 | 5 | 1 |
| Herceptin + Cilengitide s.c. | 1 | 2 | 1 | 6 |

Study 007: MDA-MB-468 – primary tumor growth

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic peptide
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (5)..(5)
<223> OTHER INFORMATION: NMeVal

<400> SEQUENCE: 1

Arg Gly Asp Phe Val
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic peptide
<220> FEATURE:
<221> NAME/KEY: MOD_RES
<222> LOCATION: (4)..(4)
<223> OTHER INFORMATION: D-Phe

<400> SEQUENCE: 2

Arg Gly Asp Phe Val
1               5
```

METHOD OF TREATING DISORDERS USING A PHARMACEUTICAL COMPOSITION OF OLIGOPEPTIDES

The present invention relates to a method of treating disorders, said method comprising the administration of a pharmaceutical composition of oligopeptides, preferably cyclic oligopeptides, said composition further comprising one or more lipophilic and/or amphiphilic compounds, preferably in the presence of water as one of the main ingredients, the use of the lipophilic and/or amphiphilic compounds for making pharmaceutical compositions of said oligopeptides, and methods of making said pharmaceutical composition.

The principally given high performance or efficacy of an active principle or drug in the treatment of diseases can nevertheless be hampered by a poor bioavailability, short half life or an complicated or inconvenient administration route. This is even more so, if the dose to be administered as high and/or the solubility of the respective active principle is low.

Thus, in many cases, the clinical and/or commercial success of an active principle or drug is completely linked to a suitable formulation that enables a convenient administration and/or an advantageous exposure of the subject of the administration to said active principle. For example, the efficacy and the balance between side-effects and efficacy can be strongly influenced by the pharmacodynamic behaviour of the respective active principle or drug in the respective formulation and/or the respective administration route.

Solubility of active pharmaceutical ingredients (API) represents one main issue for formulators as inadequate aqueous solubility may hinder development of parenterals for IV, IM or SC administration. Many new therapeutic compounds are of poor solubility; such compounds with insufficient solubility bring along a higher risk of failure during discovery and development since insufficient solubility may compromise both pharmacokinetic and pharmacodynamic properties of the compound. Commonly used excipients have a substantial potential for drug-excipient interactions, e. g. by altering protein binding and blood cell/plasma distribution. In consequence, the formulation vehicle can be an important determinant for the disposition of drug doses. Therefore, solubility may affect the overall commercial developability of the compound.

Solubility of peptides may range from low micrograms per ml to several hundreds of milligrams per ml, and is often very specific for the respective class of peptides. Even rather small structural differences can lead to significant changes in the characteristics of the respective class of peptides, including rather dramatic changes in the solubility. The required dose and route of administration may demand a higher concentration than possible in simple formulations, challenging the development of a clinically or commercially viable product. One important challenge is that peptides and proteins are typically administered via injections due to poor bioavailability by other delivery which restricts the types and concentration of excipients. On top, only small volumes of administration are appropriate for subcutaneous and intramuscular delivery routes in order to comply with patient compliance and ease of delivery, in contrast to volume and concentration constraints as known for intravenous administration settings. For subcutaneously delivery approximately 1.5 mL may be considered acceptable, preferably presented as clear solutions of low viscosity. This requires formulations which contain up to hundreds of mg/mL peptide or protein. Moreover, toxicological studies may assess approximately 10-fold higher doses than those planned for clinical studies in order to establish a safety window. This necessitates even higher concentrations for non-clinical formulations than for clinical formulations.

During formulation development, excipients are added to enhance the API's solubility (solubilizers) and/or stability (buffers, antioxidants, and chelating agents), as well as to assure safety (antimicrobial preservatives), to minimize pain and irritation upon injection (tonicity agents), and control or prolong drug delivery (polymers). On the down-side, incorporation of excipients, such as surfactants, can enhance solubility but may have negative impact on regulatory approval, toxicity and/or overall stability of the drug product.

Active pharmaceutical ingredients that belong to the class of peptidic compounds generally additionally face stability problems in many types of formulations. In formulations having about neutral pH-values, the peptides tend to show satisfying stability, but a rather low or even very low solubility in the presence of many solvents and/or excipients, even solvents and/or excipients having a rather high polarity, e.g. water. In formulations showing lower or higher than neutral pH-values, however, the solubility of said peptidic compounds often dramatically increases, but in most cases also the degradation of the peptidic structure increases dramatically.

As an alternative, liquid pharmaceutical preparations that contain at least a part of the active ingredient(s) or API as solid particles, generally referred to as suspensions, have been successfully developed and commercialized, for example suspensions with controlled-/sustained release of the active ingredients or API. Prominent examples of such pharmaceutical preparations in the form of suspensions are liquid insulin or hormone preparations. Generally, such suspensions allow subcutaneous, intramuscular, intraarticular, intravitreal, etc. injection. Typically, these pharmaceutical suspensions are oil or water based (fluid) systems.

For physico-chemical stability of suspensions it is essential that there is any or hardly any particle growth over shelf-time—known in literature as Ostwalt ripening, defined as the growth of large particles at the expense of smaller ones as a result of a difference in the solubility of the particles of varying sizes. As a direct consequence, it is common knowledge that only poorly-soluble drugs can be formulated as physically stable suspensions, i. e. with drug solubilities well below 1 mg/mL in the respective water or oil based (fluid) systems.

Pharmaceutically active oligopeptides are generally not suitable for oral administration, mostly due to poor resorption, short half life and/or lack of stability against metabolic degradation. Since such oligopeptides generally have a solubility in water well above 1 mg/mL, mostly well above 10 mg/mL, but usually well below 100 mg/mL, they are generally formulated and administered to the patient as aqueous solutions, for example solutions for (topical) ophtalmic use and intravenous (i.v.) infusion solutions for systemic administration. However, if high drug loads or high dosages regarding said oligopeptides for systemic administration are required or desired in the treatment of the patients, the only possible way of administration for said oligopeptides is the i.v. infusion of rather high volumes of said aqueous solutions.

Measures to improve the solubility or generally raise the concentration of pharmaceutically active oligopeptides in the respective formulation are little known and/or have serious disadvantages. For example, adjusting the pH value of the formulation to higher or lower pH than at physiological conditions generally improves the solubility of the pharmaceutically active oligopeptide, but leads to serious disadvantages, such as a accelerated chemical degradation and poor tonicity.

If a formulation of a pharmaceutically active oligopeptide is intended to be administrable several times per week or even several times per day, additional functional requirements have to be fulfilled, such as high tolerability, high chemical stability, high physical stability, ease of use and/or high reliability. Additionally, a convenient method of manufacturing such a formulation of a pharmaceutical active oligopeptide is highly desirous. There still exists a growing need in the art in order to develop new pharmaceuticals, including you compounds and advantageous formulations of non-compounds for treating cancer and/or metastases thereof. Preferably, said new pharmaceuticals should allow for convenient and/or efficacious systemic application or administration.

An object of the present invention therefore was to develop such a new pharmaceutical, preferably a new and advantageous formulation. It should preferably be applicable to systemic treatment, preferably lower the dose and/or preferably increase the efficiency of the pharmaceutical to be applied and/or allow for a more convenient administration and/or dosing regimen.

Thus, there is a high medical need to provide a more effective, better tolerated method for the treatment of subjects, preferably mammalian subjects, more preferably human subjects humans and especially human cancer patients that may be suffering from various cancers and/or metastasis thereof, thus preferably also leading to enhanced progression-free survival (PFS), improved quality of life (QOL) and/or increased median survival.

Recent results show that inhibiting integrins, especially $\alpha v \beta 3$ and/or $\alpha v \beta 5$, commonly expressed in various cancerous cells, can significantly decrease the resistance to chemotherapeutic agents and/or ionising radiation of otherwise chemo- or radioresistant cancerous cells and/or can induce an increased sensitivity of cancerous cells towards chemotherapeutic agents and/or ionising radiation.

Accordingly, specific integrin ligands, especially integrin ligands specific to $\alpha_v \beta_3$ and/or $\alpha_v \beta_5$ integrins according to the invention can be successfully applied to improve the efficacy of various cancer cotherapeutic agents.

For example, a phase I clinical study used cilengitide treatment in a dose escalation study on various brain tumors (NABT 9911). In some of the GBM patients in this study, an indication of response was seen. Cilengitide (=cyclo-(Arg-Gly-Asp-DPhe-NMe-Val), in very marked contrast to most cancer therapeutics currently in use has a very innocuous side effect profile, with no known MTD in humans—and is very well tolerated.

In addition to the essentially 100% mortality in GBM patients (2-year survival rate about 25%), the morbidity from neurological complications also rapidly degrades the quality of life (QOL).

For example, the standard of treatment of glioblastoma multiforme, associating radiotherapy and temozolomide, has only increased the median survival of resected patients by 2.5 months (12.1→14.6 months) compared to radiotherapy alone (Stupp et al., 2005). However, in combination with at cyclo-(Arg-Gly-Asp-DPhe-NMe-Val), this standard treatment shows significantly improved efficacy with respect to an increased median survival and quality of life. The literature cited in this paragraph is explicitly incorporated into the disclosure of the instant application by reference.

The annual worldwide incidence of squamous cell cancer of the head and neck (or Squamous Cell Carcinoma of the Head and Neck), both also referred to as SCCHN, is estimated at 500,000 patients; in the United States and Europe, 118.000 new patients are diagnosed annually. SCCHN is more predominant in males with a male:female ratio of 2:1-4:1. There is a positive relationship between smoking habits, alcohol consumption, and head and neck cancer. Approximately 90% of all head and neck malignancies are of squamous cell histology (SCCHN). Most patients are diagnosed with SCCHN at an age of 50-70 years.

A majority of patients (75%) have locally advanced disease at diagnosis. Those patients are mainly treated with radiotherapy and in some cases surgery. Newer strategies such as induction chemotherapy or chemoradiotherapy could provide better survival; however, the 5-year survival rate remains around 30%, and 60% of subjects will experience a loco-regional or distant relapse within 2 years of initial treatment.

The group of subjects with recurrent disease and/or with newly diagnosed distant metastases has very heterogeneous disease characteristics. Their median survival time, however, remains around 6-8 months with a poor quality of life. This dismal prognosis has not changed in the past 30 years.

Lung cancer is the leading cause of cancer deaths worldwide. About 170,000 new cases of lung cancer and 160,000 deaths due to this disease per year occur in the United States alone. NSCLC accounts for approximately 80% of all lung cancers.

At the time of diagnosis, approximately 30% of NSCLC patients present with locally advanced, and 40% with metastatic disease. Surgical results in earlier stages are poor compared to other tumor types (about 40% of recurrence in stages I-II). In metastatic disease, chemotherapy is the treatment of choice, but survival benefits have been modest, resulting in one-year survival of 40%, and five-year survival of less than 15%.

It is commonly accepted that the standard treatment for advanced disease (stage IV and IIIb with malignant pleural effusion) consists of platin-based (cisplatin or carboplatin) chemotherapy. However, there are many open questions in the management of these patients, such as the role of combination therapy regimen including more than two drugs, non-platinum-based therapies, and new targeted therapeutical approaches.

Currently, response rates of about 20%-30% and median survival times of 6 to 11 months have been observed in the treatment of metastatic NSCLC. Several chemotherapy combinations are used with comparable efficacy. Accordingly, also in this field is a high unmet medical need for improved methods of treatment.

Small cell lung cancer (SCLC) accounts for 15-20% of all lung cancer cases in the world, equating to approximately 80,000 new patients every year. A recent analysis of the Surveillance, Epidemiology and End Results database confirmed that in the United States, the proportion of small cell lung cancer patients has decreased from about 20% to 13.8% in 1998, likely due to the implementation of smoking cessation programs. This success, however, is to some extent outweighed by the high and rising prevalence of tobacco smoking in other parts of the world.

SCLC is typically disseminated at the time of presentation, with approximately 60% to 70% of patients having disseminated (extensive-stage) disease at presentation. Thus, surgery is rarely an option, and applies only to patients with localized (limited) disease. Relapse and death from SCLC is imminent even in patients who are treated with surgical resection. Without other therapy than surgery, survival was 2 months for patients with extensive-stage SCLC and 3 months for patients with limited-stage SCLC (Green, Am J Med 1969).

Systemic combination chemotherapy remains the mainstay of SCLC treatment, both in limited and extensive stage of their disease. For more than 20 years, etoposide and cis-/carboplatin are considered the current standard agents used in combination for the first-line treatment of patients with SCLC in the Western world. Combination therapy with more than two drugs in clinical trials has resulted in higher response rates, but also higher toxicity, and did not result in a clinically relevant overall survival benefit. Time to progression is short, with the majority of patients progressing within 3 months of completing chemotherapy. The median survival is 7 to 11 months. Less than 5% of patients survive longer than 2 years.

The term breast cancer or malignant breast neoplasm is commonly used as the generic name for cancers originating from breast tissue, most commonly from the inner lining of milk ducts or the lobules that supply the ducts with milk. Cancers originating from ducts are often referred to as ductal carcinomas; those originating from lobules are often referred to as lobular carcinomas. However, there are many different types of breast cancer, with different stages (spread), aggressiveness, and genetic makeup; survival varies greatly depending on those factors. Breast cancer is about 100 times more common in women than in men, although males tend to have poorer outcomes due to delays in diagnosis.

Breast cancer (BRCA) is the most common cancer in women worldwide, accounting for ~30% of all female cancers. It represents a major public health problem mainly due to its high incidence, excess mortality and therapeutic challenges. More than 1.1 million women are diagnosed with BRCA each year worldwide, and more than 400,000 succumb to this disease. Approximately 75% of all newly diagnosed patients are women with early stage BRCA.

Generally, treatment options include surgery, drug based therapy, including but not limited to hormonal therapy and/or chemotherapy, and radiation. Some breast cancers require hormones to grow, such as estrogen and/or progesterone, and have receptors for those hormones. After surgery those cancers are treated with drugs that interfere with those hormones and/or shut off the production of said hormones in the ovaries or elsewhere. Such drugs are generally referred to as hormone antagonists or hormone blockers.

However, despite surgery and the use of adjuvant treatments such as chemotherapy, hormonal therapy, radiotherapy and targeted drugs, many of these patients will die as a result of local or distant recurrence. The 5-year survival rate for metastatic breast cancer is in the range of 25%.

As can be seen from the above, management of BRCA has been difficult and it still is difficult.

Thus, even in view of the results achieved within the last years, the prognosis of the patients regarding most cancerous diseases is still very grim. Thus, there is a need for improved medicaments, therapy methods and treatment regimen.

According to the instant invention, this medical need is met by the provision of the new method of treating disorders, comprising administering a new and advantageous formulation to a subject. Said formulation is an advantageous formulation for peptidic compounds, preferably oligopeptides, more preferably cyclic oligopeptides, and especially cyclic oligopeptides as described herein, and comprises compounds as formulation partners with advantageous effects on the desired formulation of said peptides.

Preferably, said formulation provide for more stable formulations of said peptides, higher concentration of said peptides in said formulations, improved routes or forms of administration of said formulation, an improved pharmacological profile of said formulation, an improved efficacy and/or an optimised efficacy at a comparable dose or even at a lower dose when applied to the respective subject.

In this context, a suitable formulation for oligopeptides from the class of RGD containing oligopeptides and especially from the class of RGD containing cyclic oligopeptides, such as cyclo-(Arg-Gly-Asp-DPhe-NMeVal), should be developed, especially for use as a pharmaceutical composition or preparation. This formulation or pharmaceutical preparation should satisfy a variety of requirements. For example, it should allow a more convenient administration than i.v. infusion, e. g. subcutaneous administration, intramuscular administration or the like. Thus, as a target product profile for this formulation, it should fulfill one or more of the following criteria, preferably among others:

enable convenient administration, such as intramuscular, subcutaneous, etc.,
enable self-administration,
enable chronic or semi-chronic administration
enable daily administration, preferably in multiple daily doses (preferably up to 3 or more),
enable high drug concentration, preferably exceeding 50 mg/mL and more preferably exceeding, 100 mg/mL
enable controlled release and preferably sustained release of the drug, and
enable suitable shelf-life of pharmaceutical preparation.
shall enable a sustained release characteristic, if desired Moreover, the applied raw materials, excipients, and drug delivery technologies should preferably be compliant with the respective toxicological and clinical requirements predetermined by the intended chronic and/or multiple daily administration.

For the oligopeptide Cilengitide (EMD121974), various salts and/or polymorphic forms have been isolated which are soluble in aqueous preparations, ranging from about 8 mg/mL to about 20 mg/mL. Many of such salts and/or polymorphic forms and methods for obtaining them are described in EP 0 770 622 A1, U.S. Pat. No. 6,001,961 B1, WO 2000/053627 A1, EP 09006790.1, filed by the same applicant on May 20, 2009, and/or PCT/EP2010/003100, the disclosure of which is included herein by reference in their entirety. In general, such above described aqueous solubilities do not allow development of physically stable pharmaceutical suspensions due to expected growth of particles (see above).

During formulation experiments, solubility screening studies with the polymorphic form A1-anhydrate of EMD 121974 in oils or oily systems (such as soybean oil, sesame oil or Miglyol® 812) have been performed. These oils or oily systems, hereinafter also referred to as lipophilic compounds, surprisingly show that the typical coarse A1-anhydrate crystals as obtained by synthesis and purification (typical particle size distribution of d(10)=13 µm, d(50)=61 µm, and d(90)=241 µm) are subject to further size reduction and micronisation just when contacted to said oily systems. For example, modest stirring on a magnetic stirrer at room temperature of such coarse, non milled or non-micronized A1-anhydrate crystals makes the large drug particles disappear over time, while in return a fully homogenous, milky white suspension of very fine particles results. Depending on the size or size distribution of the employed particles and the stirring speed, this process is generally completed within 24 to 36 h, and the above described milky white suspension of very fine particles is obtained. Typically, the thus obtained homogenous, milky white suspensions do not contain any of the initially added course drug particles, but these course drug particles are "ground" and/or "micronized" in the liquid phase without introducing any relevant mechanical energy as know from ball mills or jet milling. Depending on the respective oily system, typically the drug particle size is reduced spontaneously (i.e. without grinding and/or milling processes) to d(10)=1-5 µm, d(50)=5-10 µm, and d(90)=20-30 µm) over time. Even after storage over several weeks at room temperature, this particle size distribution is maintained without any noticeable particle re-growth, thus indicating the formation of a physically stable suspension. Although the underlying mechanism of this spontaneous micronisation of the macroscopic drug particles in the presence of the liquid phase is not fully understood, it is believed that the drug particle size will converge to discrete preferred particle size distribution.

Based on the above described formation of stable suspensions of oligopeptides due to "spontaneous" drug particle size reduction in oily systems, water-based systems with lipid-like excipients were tested. As a result, such lipid-like excipients, hereinafter also referred to as amphiphilic compounds, surprisingly show a "spontaneous" drug particle size reduction in water-based systems and thus also enable stable suspensions of oligopeptides in water or water-based systems in the presence of said lipid-like excipients. It is thus believed that such amphiphilic compounds interact with the oligopeptides in a similar manner as said lipophilic compounds due to having or being composed of groups, moieties or structural units being similar or having similar properties and characteristics as the groups, moieties or structural units found in such lipophilic compounds or oils. More specifically, phospholipids have been selected as especially preferred lipid-like excipients or amphiphilic compounds, as they contain various fatty acids which are also found in the said lipophilic compounds or oils. Even more specifically, glycerophospholipids and their derivates, such as DOPG, DMPC, DMPG, DPPG, DSPG, DSPE and soy lecithin, were tested as they are ubiquitous in the human body and are major components of biological membranes. Aqueous systems containing glycerophospholipids also show that the typical coarse A1-anhydrate crystals as obtained by synthesis and purification (typical particle size distribution of d(10)=13 µm, d(50)=61 µm, and d(90)=241 µm) are subject to further size reduction and micronisation just when contacted to said aqueous systems containing said glycerophospholipid(s). Also here, modest stirring on a magnetic stirrer at room temperature makes the course, non-micronized drug particles disappear over time (generally completed within 24 to 36 h), while in return a fully homogenous, milky white suspension of very fine particles results.

Typically, the obtained homogenous, milky white suspension does not contain any of the initially added course drug particles, but these course drug particles have been ground and micronized in the liquid phase without introduction of any relevant mechanical energy as known from ball mills or jet milling. Potentially depending on the aqueous system and the phospholipid applied, the drug particle size is reduced "spontaneously" (i.e. without grinding and/or milling processes) to d(10)=1-5 µm, d(50)=5-10 µm, and d(90)=20-30 µm) or to d(10)=1-10 µm, d(50)=10-25 µm and d(90)=25-60 µm over time (more than 24 hours). Even after storage over several weeks at room temperature, this particle size distribution is maintained without any noticeable particle re-growth, thus indicating the formation of a physically stable suspension of the oligopeptide also in the water based system in the presence of one or more amphiphilic compounds. Although the underlying mechanism of this spontaneous micronisation of the macroscopic drug particles in the presence of the liquid phase is not yet fully understood, it is believed that the drug particle size will converge to discrete preferred particle size distribution, not only in the previous described oily systems, but also in aqueous systems if suitable excipients, i.e. the lipid-like excipients or amphiphilic compounds, are added as described herein. Additionally, the formation of the above discussed stable suspensions can preferably be facilitated and/or accelerated by grinding or preferably micronizing the particles of the respective oligopeptide before they are contacted with the liquid phase consisting of or containing the lipophilic compounds and/or the amphilphilic compounds.

The accordingly obtained suspensions show advantageous properties which make them very suitable pharmaceutical compositions or at least a very suitable basis for pharmaceutical compositions. This is discussed in more detail below.

Thus, an advantageous formulation or composition of peptides can be achieved by contacting one or more peptides and especially one or more oligopeptides with one or more lipophilic and/or amphiphilic compounds. Advantageously, novel compositions can be formed which can preferably be characterised as suspensions. Generally, these compositions comprise a continuous liquid phase, containing a major amount of said one or more lipophilic and/or amphiphilic compounds, and a discontinuous phase, containing the major amount of said one or more peptides. These advantageous formulations can be water-based or essentially free of water, depending inter-alia on the amount of the lipophilic and/or amphiphilic compounds employed in said formulation Subject of the instant invention is thus a new formulation, composition or pharmaceutical composition as described below. The new formulation, composition or pharmaceutical composition as described below preferably shows one or more of the advantageous properties described herein.

BRIEF DESCRIPTION OF THE FIGURES

FIG. 20: Cilengitide in combination with Herceptin in Her2+ breast cancer model BT474; Graphical display of treatment schedule; Tabular Display of results (See Example 24).

Figure 1:
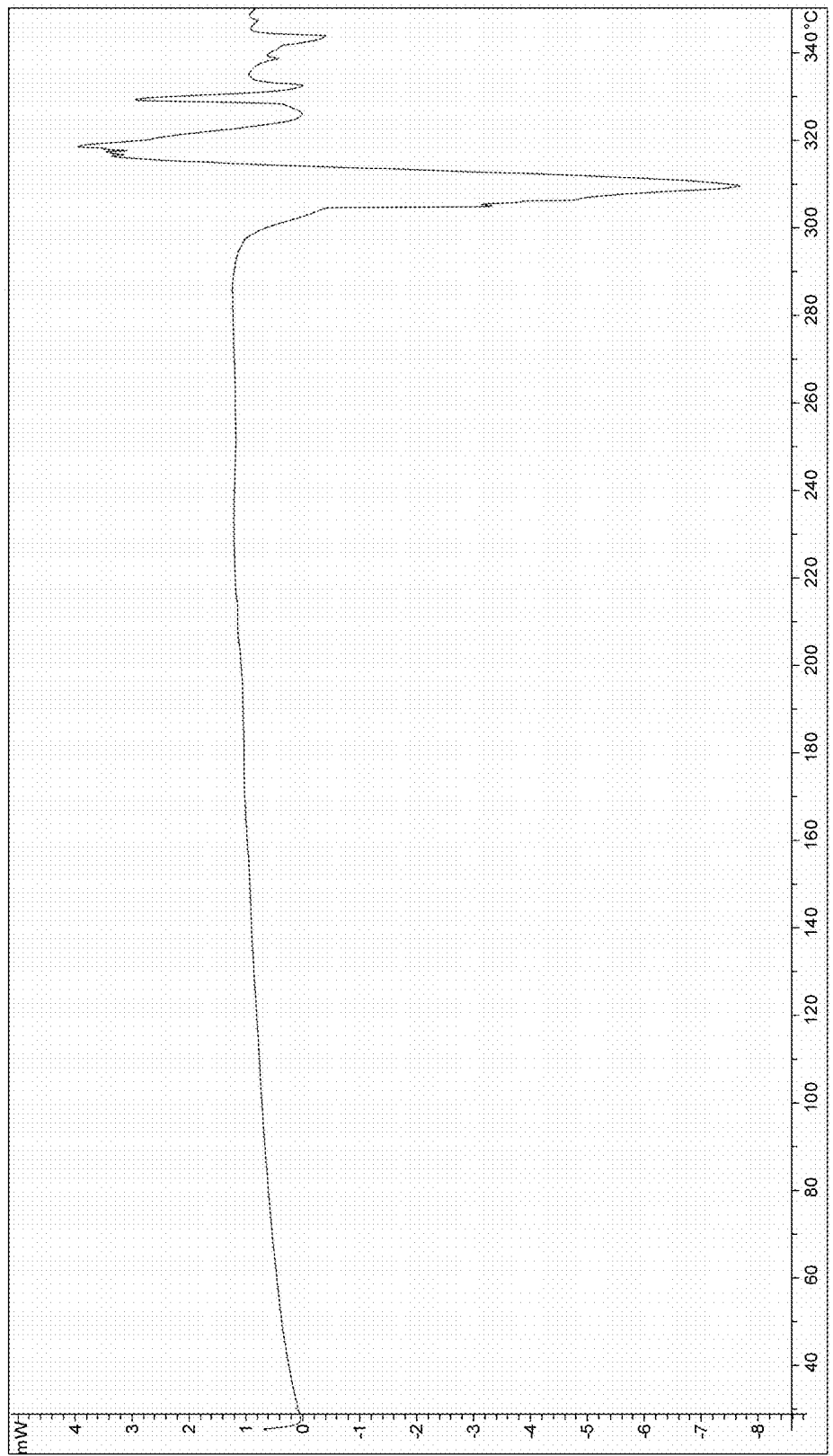
FIG. 1 shows the DSC scan of form A1 (Mettler-Toledo DSC 821, 5 K/min, nitrogen purge gas 50 ml/min).

Thus, subjects of the instant invention are:

[1] A method for treating disorders, said method comprising administering to a subject a composition, preferably a pharmaceutical composition, wherein said composition comprises composition, comprising
a) 8 to 80% and preferably 12 to 90% of at least one oligopeptide, preferably at least one cyclic oligopeptide, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, even more preferably between 6 mg/ml and 10 mg/ml, and especially between 5 mg/ml and 9 mg/ml,
b) 0.01 to 90%, preferably 0.01 to 80 percent, more preferably, 0.01 to 70 percent and especially 0.1 to 60%, of one or more lipophilic and/or amphiphilic compounds having a molar weight in the range of 200 g/mol to 2000 g/mol, preferably 300 g/mol to 1500 g/mol, more preferably 500 g/mol to 1000 g/mol, and especially 700 g/mol to 900 g/mol,
and optionally
c) 0 to 89% of water,
with the proviso that the sum of a), b) and c) makes up to 40 or more %, preferably 50 or more percent, more preferably 70 or more percent, even more preferably 90 percent or more and especially 95 percent or more, of the total composition.

[2] Preferred is a method for treating disorders as described herein and especially as described paragraph [1] and/or the paragraphs relating thereto, wherein said method comprises administering to a subject a composition, preferably a pharmaceutical composition, as described herein and especially as described in paragraph [1].

[3] Especially preferred is a method for treating disorders as described herein and especially as described in paragraphs [1], [2] and/or the paragraphs relating thereto, wherein said method comprises administering to a mammalian subject, more preferably to a human subject and especially to a human patient, a composition, preferably a pharmaceutical composition, as described herein and especially as described in paragraph [1].

The solubility of said cyclic oligopeptide(s) is preferably determined as described herein.

Amphiphilic compounds according to the invention in the broadest sense preferably are molecules which comprise both a polar (hydrophilic) moiety or group and an apolar (hydrophobic or lipophilic) moiety or group; preferably, the amphiphilic compounds according to the invention show interfacial activity and/or surface activity. For example, they preferably are surface active agents and/or surfactants, or preferably are able to act as surface active agents and/or surfactants.

Lipophilic compounds according to the invention in the broadest sense preferably are molecules which either i) exclusively consist of one or more apolar (hydrophobic or lipophilic) moieties or groups, but contain no polar (hydrophobic or lipophilic) moiety or group; or ii) are predominantly comprised of one or more apolar (hydrophobic or lipophilic) moieties or groups and contain an only to a minor extent polar (hydrophobic or lipophilic) moiety or group, so that it is not or hardly soluble in water, but very soluble in oils; preferably, the lipophilic compounds according to the invention show no interfacial activity and/or no surface activity.

[4] Composition, preferably pharmaceutical composition, for use in the method for treating disorders as described herein and especially as described in paragraph numbered [1], [2], [3] and/or preferably also as described in the paragraphs relating thereto, wherein at least one of the lipophilic and/or amphiphilic compounds according to b) comprises:

α) a glycerol moiety,

β) one or more fatty acid moieties, and/or

γ) one or more fatty alcohol moieties; and more preferably

α) a glycerol moiety, and/or

β) one or more fatty acid moieties.

More preferably, the amphiphilic compounds according to b) comprise:

α) a glycerol moiety, and at least one moiety selected from

β) one or more fatty acid moieties and

γ) one or more fatty alcohol moieties.

Even more preferably, the amphiphilic compounds according to b) comprise:

α) a glycerol moiety, and

β) one or more fatty acid moieties.

A glycerol moiety according to the invention preferably is a moiety that is derived from glycerol or can be derived from glycerol. More specifically, the glycerol moiety is preferably selected from the following structures in the squares:

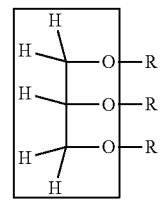
i)

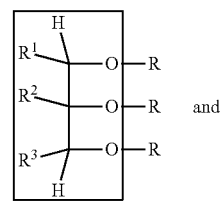
ii) and

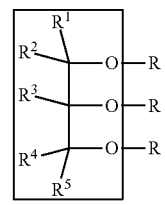
iii)

wherein $R^1$, $R^2$, $R^3$, $R^4$ and $R^5$ are independently from each other are selected from H, methyl, ethyl and hydrophilic moieties, more preferably from H and hydrophilic moieties; preferably with the proviso that only one or two of $R^1$, $R^2$, $R^3$, $R^4$ and $R^5$ are hydrophilic moieties, and more preferably that only one of $R^1$, $R^2$, $R^3$, $R^4$ and $R^5$ is a hydrophilic moiety;

and all salts and/or stereoisomers thereof.

The glycerol moiety is preferably selected from the following structures in the squares:

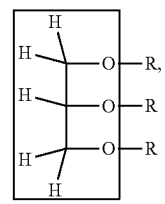
i)

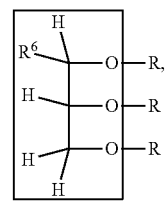
ii)

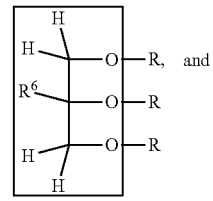
iii) and iv)

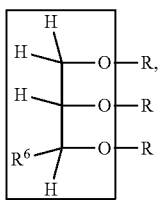

wherein $R^6$ is selected from methyl, ethyl and hydrophilic moieties, more preferably from methyl and hydrophilic moieties;
and all salts and/or stereoisomers thereof.

Hydrophilic moieties in this regard are preferably selected from the group consisting of:
α) —OH, —ONa, —OK, —O⁻, —NH$_2$, —NH$_3^+$, —N(CH$_3$)$_3^+$, —PO$_3$H, —PO$_3$Na, —PO$_3$K, —PO$_3^-$, —O—PO$_3$H, —O—PO$_3$Na, —O—PO$_3$K, —O—PO$_3^-$;
β) —(CH$_2$)$_n$—OH, —(CH$_2$)$_n$—ONa, —(CH$_2$)$_n$—OK, —(CH$_2$)$_n$—O⁻, —(CH$_2$)$_n$—NH$_2$, —(CH$_2$)$_n$—NH$_3^+$, —(CH$_2$)$_n$—N(CH$_3$)$_3^+$, —(CH$_2$)$_n$—PO$_3$H, —(CH$_2$)$_n$—PO$_3$Na, —(CH$_2$)$_n$—PO$_3$K, —(CH$_2$)$_n$—PO$_3^-$, —(CH$_2$)$_n$—O—PO$_3$H, —(CH$_2$)$_n$—O—PO$_3$Na, —(CH$_2$)$_n$—O—PO$_3$K, —(CH$_2$)$_n$—O—PO$_3^-$,
wherein n is 1, 2, 3 or 4, preferably 1, 2 or 3 and especially 1 or 2; and/or
γ) an ethanolamine moiety, a choline moiety, a phosphatidyl moiety, a phosphatidylcholine moiety, a sulfatidyl and a sulfatidylcholine moiety;
and a salt or other salt thereof.

The glycerol moieties in lipophilic compounds preferably do not comprise hydrophilic residues (which are bound to the carbon backbone of the glycerol moiety) as described above.

A fatty acid moiety in the context of the instant invention preferably is a moiety that is derived from a fatty acid or can be derived from a fatty acid. More preferably, a fatty acid moiety is the part of fatty acid, preferably a fatty acid as defined below, that is chemically bound to another moiety, e.g. esterified to another moiety, that is part of said lipophilic and/or amphiphilic compound.

The meaning of the term fatty acid is well known in the art and is preferably to be understood here in its broadest context. More preferably, a fatty acid in the context of the instant invention is an aliphatic saturated or (ethylenically) unsaturated, branched or unbranched carboxylic acid having 4 to 35 carbon atoms, more preferably 6 to 30 carbon atoms and especially 8 to 25 carbon atoms. Even more preferably, a fatty acid in the context of the instant invention is an aliphatic saturated or once, twice, three times or four times (ethylenically) unsaturated, branched or unbranched, preferably unbranched, carboxylic acid having 4 to 35 carbon atoms, more preferably 6 to 30 carbon atoms and especially 8 to 25 carbon atoms. Even more preferably, a fatty acid in the context of the instant invention is an aliphatic saturated or once or twice (ethylenically) unsaturated, branched or unbranched, preferably unbranched, carboxylic acid having 4 to 35 carbon atoms, more preferably 6 to 30 carbon atoms and especially 8 to 25 carbon atoms.

Thus, the fatty acid moiety according to the invention preferably is one of the structures given in the squares below, whereas the structures in the circles constitute the fatty acid as the whole:

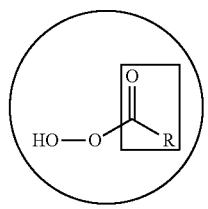

and/or

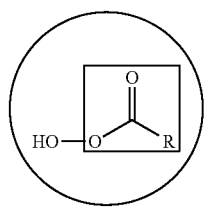

preferably

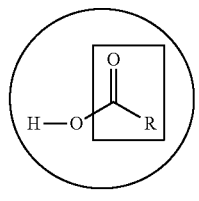

Thus, especially preferably, a fatty acid moiety according to the invention is the acyl moiety or acyl residue of the corresponding fatty acid.

Even more preferred fatty acid moieties are selected from the following formulae:

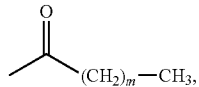

wherein m is 2 to 33, more preferably 4 to 28 and even more preferably 6 to 23;

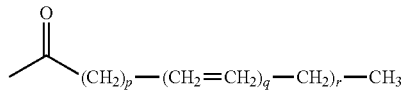

wherein
p is 1 to 20, more preferably 3 to 18, even more preferably 4 to 15 and especially 6 to 13,
q is 0 to 6, more preferably 1 to 5, more preferably 1, 2, 3, or 4 and especially 1, 2 or 3,
r is 1 to 20, more preferably 3 to 15, even more preferably 6 to 12 and especially 6, 7 or 8,
preferably with the proviso that the sum of p and r is 4 to 30, more preferably 5 to 25, even more preferably 8 to 22 and especially 10 to 20 and/or with the proviso that the sum of p, q and r is 5 to 30, more preferably 6 to 25, even more preferably 9 to 23 and especially 11 to 21;

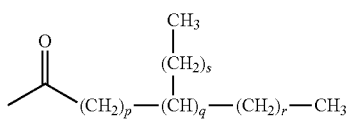

wherein p is 1 to 20, more preferably 3 to 18, even more preferably 4 to 15 and especially 6 to 13, q is 0 to 6, more preferably 1 to 5, more preferably 1, 2, 3, or 4 and especially 1, 2 or 3, r is 1 to 20, more preferably 3 to 15, even more preferably 6 to 12 and especially 6, 7 or 8, and s is 1 to 20, more preferably 1 to 15, even more preferably 1 to 10 and especially 1 to 5, preferably with the proviso that the sum of p, r and s is 4 to 30, more preferably 5 to 25, even more preferably 8 to 22 and especially 10 to 20 and/or with the proviso that the sum of p, q, r and s is 5 to 30, more preferably 6 to 25, even more preferably 9 to 23 and especially 11 to 21; and/or

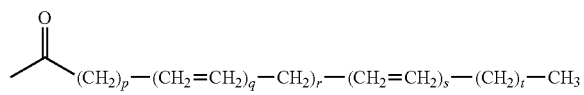

wherein p is 1 to 20, more preferably 3 to 15, even more preferably 6 to 12 and especially 6, 7 or 8, q is 0 to 6, more preferably 1 to 5, more preferably 1, 2, 3, or 4 and especially 1, 2 or 3, r is 1 to 20, more preferably 3 to 18, even more preferably 4 to 15 and especially 6 to 12, and s is 0 to 6, more preferably 1 to 5, more preferably 1, 2, 3, or 4 and especially 1, 2 or 3, t is 1 to 20, more preferably 1 to 15, even more preferably 1 to 10, even more preferably 3 to 8 and especially 4, 5, 6, 7 or 8, preferably with the proviso that the sum of p, r and t is 4 to 30, more preferably 6 to 25, even more preferably 8 to 22 and especially 10 to 20 and/or with the proviso that the sum of p, q, r, s and t is 5 to 30, more preferably 7 to 25, even more preferably 9 to 23 and especially 11 to 21.

Even more preferably, the fatty acid moieties are selected from the group of:

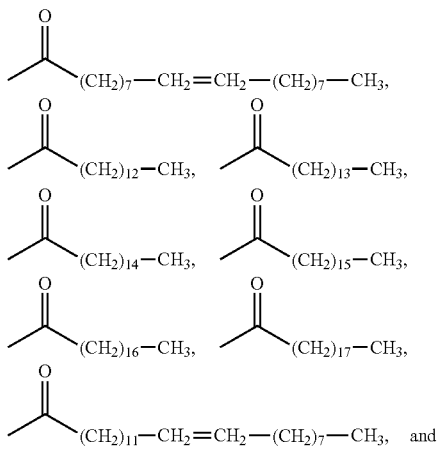

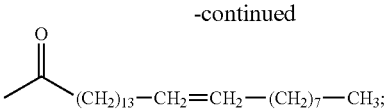

and, in case of the unsaturated fatty acid moieties, all stereoisomers thereof.

Even more preferably, the fatty acid moieties are selected from the group consisting of myristoyl (corresponds to myristic acid), oleoyl (corresponds to oleic acid), palmitoyl (corresponds to palmitic acid), stearoyl (corresponds to stearic acid), margaroyl (corresponds to margaric acid), arachidoyl (corresponds to arachic or arachidic acid), behenoyl (corresponds to behenic acid), erucoyl (corresponds to erucic acid), linoleoyl (corresponds to linoleic acid) and linolenoyl (corresponds to linolenic acid).

Even more preferably, the fatty acid moieties are selected from the group consisting of myristoyl, oleoyl, palmitoyl and stearoyl.

Even more preferably, the fatty acid moieties are selected from the group consisting of myristoyl, palmitoyl and stearoyl.

Especially preferably, the fatty acid moiety is myristoyl.

A fatty alcohol moiety in the context of the instant invention preferably is a moiety that is derived from a fatty alcohol or can be derived from a fatty alcohol. More preferably, a fatty alcohol moiety is a fatty alcohol, preferably a fatty alcohol as defined below, that is chemically bound to another moiety, e.g. esterified to another moiety, that is part of said lipophilic and/or amphiphilic compound.

The meaning of the term fatty alcohol is well known in the art and is preferably to be understood here in its broadest context. More preferably, a fatty alcohol in the context of the instant invention is an aliphatic saturated or (ethylenically) unsaturated, branched or unbranched carboxylic acid having 4 to 35 carbon atoms, more preferably 6 to 30 carbon atoms and especially 8 to 25 carbon atoms. Even more preferably, a fatty alcohol in the context of the instant invention is an aliphatic saturated or once, twice, three times or four times (ethylenically) unsaturated, branched or unbranched, preferably unbranched, carboxylic acid having 4 to 35 carbon atoms, more preferably 6 to 30 carbon atoms and especially 8 to 25 carbon atoms. Even more preferably, a fatty alcohol in the context of the instant invention is an aliphatic saturated or once or twice (ethylenically) unsaturated, branched or unbranched, preferably unbranched, alcohol having 4 to 35 carbon atoms, more preferably 6 to 30 carbon atoms and especially 8 to 25 carbon atoms. Typically, such fatty alcohols are derived, can be derived or are obtainable from the corresponding alcohol, e.g. by a reduction of the corresponding fatty acid.

Thus, the fatty alcohol moiety according to the invention preferably are the structures given in the squares below, whereas the structures in the circles constitute the fatty alcohol as the whole:

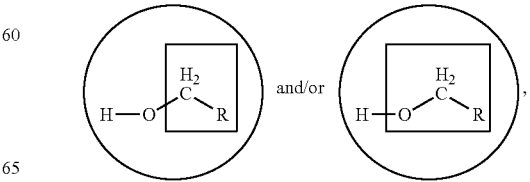

preferably

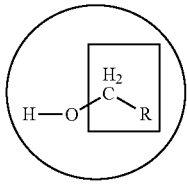

Thus, especially preferably, a fatty alcohol moiety according to the invention is the alkyl moiety or alkyl residue of the corresponding fatty alcohol.

Even more preferred fatty alcohol moieties are selected from the following formulae:

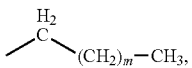

wherein m is 2 to 33, more preferably 4 to 28 and even more preferably 6 to 23;

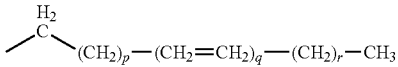

wherein
p is 1 to 20, more preferably 3 to 18, even more preferably 4 to 15 and especially 6 to 13,
q is 0 to 6, more preferably 1 to 5, more preferably 1, 2, 3, or 4 and especially 1, 2 or 3,
r is 1 to 20, more preferably 3 to 15, even more preferably 6 to 12 and especially 6, 7 or 8,
preferably with the proviso that the sum of p and r is 4 to 30, more preferably 5 to 25, even more preferably 8 to 22 and especially 10 to 20 and/or with the proviso that the sum of p, q and r is 5 to 30, more preferably 6 to 25, even more preferably 9 to 23 and especially 11 to 21;

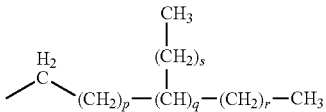

wherein
p is 1 to 20, more preferably 3 to 18, even more preferably 4 to 15 and especially 6 to 13,
q is 0 to 6, more preferably 1 to 5, more preferably 1, 2, 3, or 4 and especially 1, 2 or 3,
r is 1 to 20, more preferably 3 to 15, even more preferably 6 to 12 and especially 6, 7 or 8, and
s is 1 to 20, more preferably 1 to 15, even more preferably 1 to 10 and especially 1 to 5,
preferably with the proviso that the sum of p, r and s is 4 to 30, more preferably 5 to 25, even more preferably 8 to 22 and especially 10 to 20 and/or with the proviso that the sum of p, q, r and s is 5 to 30, more preferably 6 to 25, even more preferably 9 to 23 and especially 11 to 21; and/or

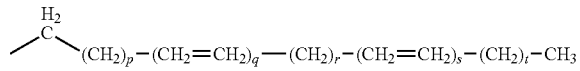

wherein
p is 1 to 20, more preferably 3 to 15, even more preferably 6 to 12 and especially 6, 7 or 8,
q is 0 to 6, more preferably 1 to 5, more preferably 1, 2, 3, or 4 and especially 1, 2 or 3,
r is 1 to 20, more preferably 3 to 18, even more preferably 4 to 15 and especially 6 to 12, and
s is 0 to 6, more preferably 1 to 5, more preferably 1, 2, 3, or 4 and especially 1, 2 or 3,
t is 1 to 20, more preferably 1 to 15, even more preferably 1 to 10, even more preferably 3 to 8 and especially 4, 5, 6, 7 or 8,
preferably with the proviso that the sum of p, r and t is 4 to 30, more preferably 6 to 25, even more preferably 8 to 22 and especially 10 to 20 and/or with the proviso that the sum of p, q, r, s and t is 5 to 30, more preferably 7 to 25, even more preferably 9 to 23 and especially 11 to 21.

Even more preferably, the fatty alcohol moieties are selected from the group of:

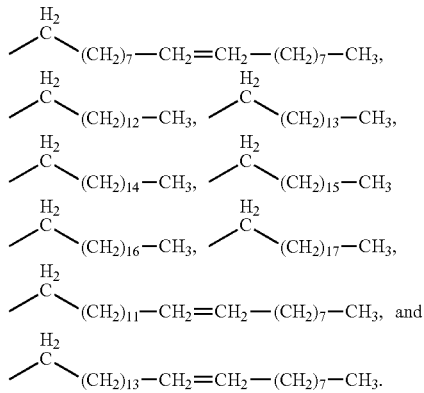

Even more preferably, the fatty alcohol moieties are independently selected from the alkyl residues of the fatty alkohols of the group consisting of oleic alcohol, myristic alcohol, palmitic alcohol, stearic alcohol, margaric alcohol, arachic alcohol, behenic alcohol, erucic alcohol, linolic alcohol and linolenic alcohol.

[5] Preferred for use in the methods according to the instant invention are compositions as described herein and especially as described in one or more of the paragraphs numbered [1], [2], [3], [4] and/or the paragraphs relating thereto, wherein
at least one of the lipophilic and/or amphiphilic compounds according to b) comprises a hydrophilic moiety, and especially wherein
at least one of the amphiphilic compounds according to b) comprises a hydrophilic moiety. Suitable hydrophilic moieties are known to the skilled artisan.

[6] Preferred for use in the methods according to the instant invention are compositions as described herein and especially as described in the paragraph numbered [5], wherein the hydrophilic moiety comprises an ethanolamine moiety, a choline moiety, a phosphatidyl moiety and/or a sulfatidyl moiety, and/or a salt thereof, or more preferably is an ethanolamine moiety, a choline moiety, a phosphatidyl moiety and/or a sulfatidyl moiety, and/or a salt thereof.

[7] Preferred for use in the methods according to the instant invention are compositions as described herein and especially as described in the paragraph numbered [5] and/or [6], wherein the hydrophilic moiety comprises a phosphoethanolamine moiety, a phosphatidylcholine moiety, a phosphatidylglycerol moiety and/or a sulfatidylglycerol moiety, and/or a salt thereof, or more preferably is phosphoethanolamine moiety, a phosphatidylcholine moiety, a phosphatidylglycerol moiety and/or a sulfatidylglycerol moiety and especially a phosphatidylglycerol moiety, and/or a salt thereof.

As regards the salts thereof, a basic hydrophilic moiety can be present as a salt, such as an acid addition salt, or can be converted into a salt with an acid, such as into the associated acid addition salt, for example by reacting equivalent quantities of the compound comprising the basic hydrophilic moiety and the acid in an inert solvent such as ethanol and then concentrating by evaporation. Suitable acids for such salts are, in particular, those which give rise to physiologically harmless salts. Thus, use can be made of inorganic acids, for example sulphuric acid, nitric acid, hydrohalic acids such as hydrochloric acid or hydrobromic acid, phosphoric acids such as orthophosphoric acid, and sulphamic acid, and, in addition, organic acids, in particular aliphatic, alicyclic, araliphatic, aromatic or heterocyclic monobasic or polybasic carboxylic, sulphonic or sulphuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulphonic acid, ethanesulphonic acid, ethanedisulphonic acid, 2-hydroxyethanesulphonic acid, benzenesulphonic acid, p-toluenesulphonic acid, naphthalenemonosulphonic acid, naphthalenedisulphonic acid and lauryl sulphuric acid. Alternatively, an acidic hydrophilic moiety can be present as a salt, such as a base addition salt, or can be converted into a salt with a base, e.g. into the associated base addition salt. In this regard, the sodium, potassium, magnesium, calcium and ammonium salts of the acidic hydrophilic moieties are particularly preferred. Also preferred are substituted ammonium salts, for example the dimethyl-, diethyl- or diisopropylammonium salts, monoethanol-, diethanol- or diisopropylammonium salts, cyclohexyl- and dicyclohexylammonium salts, and dibenzylethylenediammonium salts, and also, for example, salts with arginine or lysine.

Especially preferred in this regard are the sodium salts, the potassium salts, ammonium salts and the hydrochloric acid salts. Especially preferred in this regard are the sodium salts.

Lipophilic compounds and especially natural and/or synthetic oils are known to the skilled artisan. Preferred are natural and/or synthetic oils having a molar weight in the range of 200 g/mol to 2000 g/mol, preferably 300 g/mol to 1500 g/mol, more preferably 500 g/mol to 1000 g/mol, and especially 700 g/mol to 900 g/mol. Preferably, the natural and/or synthetic oils are liquid at about room temperature (about 25° C.) and especially are liquid at physiological conditions and/or physiological temperatures (about 37° C.). Thus, the melting point of said natural and/or synthetic oils, and preferably also of the mixtures thereof, is +20° C. or lower, preferably +10° C. or lower and even more preferably 0° C. or lower. However, typically a melting point below the above given values, but above −50° C., above −40° C., above −30° C., above −20° C. or even above −10° C. is sufficient.

Preferred lipophilic compounds that are natural and/or synthetic oils include, but are not limited to
i) fatty acid mono-, di-, tri- or polyesters of mono-, di-, tri- and polyoles,
ii) fatty acid diester of di-, tri- or polyoles,
iii) fatty acid triester of tri- or polyoles, and/or
iv) fatty alcohol mono-, di-, tri- or polyesters of mono-, di-, tri- and polyoles,
v) fatty alcohol diether of di-, tri- or polyoles,
vi) fatty alcohol triether of tri- or polyoles,
and preferably also mixtures thereof.

Especially preferred in this regard are fatty acid diester of dioles and/or fatty acid triester of trioles, wherein the fatty acids or fatty acid moieties preferably are as defined herein and/or wherein the dioles and trioles preferably are as defined herein.

Even more preferred are natural and/or synthetic oils that are fatty acid triester of trioles, wherein the fatty acid moiety is as described herein and/or the triol moiety is a glycerol moiety as described herein.

Preferably, said natural and/or synthetic oils and especially the fatty acid triester of trioles do not comprise a hydrophilic moiety as described herein.

Preferred examples of natural oils are selected from vegetable oils, and more preferably selected from sesame oil, rapeseed oil, soybean oil, sunflower oil and olive oil, and mixtures thereof.

Preferred examples of synthetic oils are selected from pharmaceutically acceptable oils, e.g. the pharmaceutically acceptable oils described in the Pharmacopeia, and more preferably selected from pharmaceutically acceptable triglycerides, preferably middle sized chain triglycerides, such as Miglyols®, preferably Miglyol® 810, Miglyol® 812, Miglyol® 818, Miglyol® 829 and Miglyol® 840, and especially Miglyol® 812, and mixtures thereof.

Said Miglyols are preferably selected from the group consisting of caprylic/capric triglycerides (Miglyol® 810, Miglyol® 812), caprylic/capric/linoleic triglycerides (Miglyol® 818), caprylic/capric/succinic triglycerides (Miglyol® 829) and propylene glycol dicaprylate/dicaprate (Miglyol® 840 and more preferably selected from caprylic/capric triglycerides (Miglyol® 810, Miglyol® 812), caprylic/capric/linoleic triglycerides (Miglyol® 818), caprylic/capric/succinic triglycerides (Miglyol® 829).

However, all triacylglycerides or fatty acid triester of trioles that are pharmaceutically acceptable and have a melting point in the herein given ranges are deemed suitable lipophilic compounds according the invention.

Thus, preferred is a composition, preferably a pharmaceutical composition, as described herein and especially as described in one or more of the paragraphs numbered [1] to [4] and preferably also as described in the paragraphs relating thereto for use in the methods according to the instant invention, comprising
a) 12 to 90%, preferably 20 to 80%, more preferably 20 to 60% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml,
b) 10 to 90%, preferably 20 to 80% more preferably 40 to 80% and especially 60 to 80% of at least one lipophilic compound selected from natural oils and synthetic oils and mixtures thereof, preferably pharmaceutically acceptable natural oils and/or synthetic oils and mixtures thereof, and especially fatty acid triester of trioles, wherein the fatty acid moiety is as described herein and the triol moiety is a glycerol moiety as described herein, and optionally
c) 0 to 30%, preferably 0 to 20%, more preferably 0 to 10% and especially 0.01 to 5% of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

Preferred in this regard are oligopeptides or cyclic oligopeptides which comprise the Arg-Gly-Asp-subsequence.

A Composition as described herein and especially as described in one or more of the paragraphs numbered [1] to [4] and preferably also as described in the paragraphs relating thereto for use in the methods according to the instant invention, comprising
a) 7 to 80% or 12 to 90%, preferably 20 to 80%, more preferably 20 to 60% and especially 20 to 40% of a cyclic oligopeptide selected from cyclo-(Arg-Gly-Asp-DPhe-NMeVal), cyclo-(Arg-Gly-Asp-DPhe-Val) and the pharmaceutically acceptable derivatives, solvates and/or salts thereof, and preferably selected from cyclo-(Arg-Gly-Asp-DPhe-NMeVal) and the pharmaceutically acceptable solvates and/or salts, preferably having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml,
b) 10 to 90%, preferably 20 to 80% more preferably 40 to 80% and especially 60 to 80% of at least one lipophilic compound selected from natural oils and synthetic oils and mixtures thereof, preferably pharmaceutically acceptable natural oils and/or synthetic oils and mixtures thereof, and especially fatty acid triester of trioles, wherein the fatty acid moiety is as described herein and the triol moiety is a glycerol moiety as described herein, and optionally
c) 0 to 30%, preferably 0 to 20%, more preferably 0 to 10% and especially 0.01 to 5% of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [4] and preferably also as described in the paragraphs relating thereto for use in the methods according to the instant invention, comprising
a) 12 to 90%, preferably 20 to 80%, more preferably 20 to 60% and especially 20 to 40% of cyclo-(Arg-Gly-Asp-DPhe-NMeVal), more preferably of an anhydrate of the inner salt of cyclo-(Arg-Gly-Asp-DPhe-NMeVal) and especially of the crystalline form A1 of the inner salt of cyclo-(Arg-Gly-Asp-DPhe-NMeVal),
b) 10 to 90%, preferably 20 to 80% more preferably 40 to 80% and especially 60 to 80% of at least one lipophilic compound selected from natural oils and synthetic oils and mixtures thereof, preferably pharmaceutically acceptable natural oils and/or synthetic oils and mixtures thereof, and especially fatty acid triester of trioles, wherein the fatty acid moiety is as described herein and the triol moiety is a glycerol moiety as described herein, and optionally
c) 0 to 30%, preferably 0 to 20%, more preferably 0 to 10% and especially 0.01 to 5% of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [4] and preferably also as described in the paragraphs relating thereto for use in the methods according to the instant invention, comprising
a) 12 to 90%, preferably 20 to 80%, more preferably 20 to 60% and especially 20 to 40% of cyclo-(Arg-Gly-Asp-DPhe-NMeVal), more preferably of an anhydrate of the inner salt of cyclo-(Arg-Gly-Asp-DPhe-NMeVal) and especially of the crystalline form A1 of the inner salt of cyclo-(Arg-Gly-Asp-DPhe-NMeVal), preferably having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml,
b) 10 to 90%, preferably 20 to 80% more preferably 40 to 80% and especially 60 to 80% of at least one lipophilic compound selected from natural oils and synthetic oils and mixtures thereof, preferably pharmaceutically acceptable natural oils and/or synthetic oils and mixtures thereof, and especially fatty acid triester of trioles, wherein the fatty acid moiety is as described herein and the triol moiety is a glycerol moiety as described herein, and optionally
c) 0 to 30%, preferably 0 to 20%, more preferably 0 to 10% and especially 0.01 to 5% of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [4] and preferably also as described in the paragraphs relating thereto for use in the methods according to the instant invention, comprising
a) 12 to 90%, preferably 15 to 80%, preferably 15 to 60%, more preferably 15 to 50% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml b) 0.01 to 60%, preferably 0.01 to 30%, more preferably 0.01 to 15%, even more preferably 0.05 to 10%, even more preferably 0.05 to 5% and especially 0.1 to 5%, of one or more amphiphilic compounds, c) 10 to 89.99%, preferably 20 to 89.99%, more preferably 30 to 84.99%, even more preferably 40 to 84.99%, even more preferably 50 to 84.95% and especially 60 to 79.95% of water, with the proviso that the sum of a), b) and c) makes up to 70 or more %, preferably 80 or more %, more preferably 90 or more %, even more preferably 95 or more % and especially 95 to 99.9% of the total composition.

Amphiphilic compounds and especially amphiphilic lipids are known to the skilled artisan. Amphiphilic compounds in the context of the instant invention preferably comprise one or more lipophilic parts and one or more hydrophilic parts. Preferred are amphiphilic compounds and especially amphiphilic lipids having a molar weight in the range of 200 g/mol to 2000 g/mol, preferably 300 g/mol to 1500 g/mol, more preferably 500 g/mol to 1000 g/mol, and especially 700 g/mol to 900 g/mol. Preferably, amphiphilic lipids in the context of the instant invention comprise at least one fatty acid moiety or at least one fatty alcohol moiety, preferably as a part of the lipophilic part, and/or a mono-, di-, tri- or polyole, preferably a diole or triole, preferably as a part of the hydrophilic part. Preferably, said mono-, di-, tri- or polyole, preferably a diole or triole, additionally comprises a hydrophilic moiety as described herein.

[8] More preferably, amphiphilic lipids in the context of the instant invention comprise at least one or two fatty acid moieties, preferably as a part of the lipophilic part, and/or a triole, preferably glycerol, preferably as a part of the hydrophilic part. Thus, preferred are amphiphilic lipids having phosphatidyl-polyol or sulfatidyl-polyol moieties as the hydrophilic part, and derivatives, salts and/or alcoholates thereof and more preferably the salts thereof. Even more preferred are amphiphilic lipids having phosphatidyl-glycerol or sulfatidyl-glycerol moieties as the hydrophilic part, and derivatives, salts and/or alcoholates thereof and more preferably the salts thereof.

Thus, even more preferred are amphiphilic lipids having

α) phosphatidyl-glycerol or sulfatidyl-glycerol moieties, preferably as the hydrophilic part, and β) one or two, preferably two fatty acid moieties, preferably as the lipophilic part, and derivatives, salts and/or alcoholates thereof and more preferably the salts thereof.

Preferably, the amphiphilic compounds according to b) can be selected from the group consisting of:

fatty acid monoesters of phosphatidylpolyoles, and derivatives, salts and alcoholates thereof;

fatty acid diesters of phosphatidylpolyoles, and derivatives, salts and alcoholates thereof;

and the salts and alcoholates thereof;

fatty acid triesters of phosphatidylpolyoles, and derivatives, salts and alcoholates thereof;

fatty acid polyesters of phosphatidylpolyoles, and derivatives, salts and alcoholates thereof;

fatty acid monoesters of sulfatidylpolyoles, and derivatives, salts and alcoholates thereof;

fatty acid diesters of sulfatidylpolyoles, and derivatives, salts and alcoholates thereof;

and the salts and alcoholates thereof;

fatty acid triesters of sulfatidylpolyoles, and derivatives, salts and alcoholates thereof;

fatty acid polyesters of sulfatidylpolyoles, and derivatives, salts and alcoholates thereof.

Alternatively preferably, the amphiphilic compounds according to b) can be selected from the group consisting of:

fatty alcohol monoethers of phosphatidylpolyoles, and derivatives, salts and alcoholates thereof;

fatty alcohol diethers of phosphatidylpolyoles, and derivatives, salts and alcoholates thereof;

and the salts and alcoholates thereof;

fatty alcohol triethers of phosphatidylpolyoles, and derivatives, salts and alcoholates thereof;

fatty alcohol polyethers of phosphatidylpolyoles, and derivatives, salts and alcoholates thereof;

fatty alcohol monoethers of sulfatidylpolyoles, and derivatives, salts and alcoholates thereof;

fatty alcohol diethers of sulfatidylpolyoles, and derivatives, salts and alcoholates thereof;

and the salts and alcoholates thereof;

fatty alcohol triethers of sulfatidylpolyoles, and derivatives, salts and alcoholates thereof;

fatty alcohol polyethers of sulfatidylpolyoles, and derivatives, salts and alcoholates thereof.

Phosphatidylpolyoles according to the invention preferably comprise mono- and pyrophosphatidylpolyoles, including, but not limited to, monophosphatidylpolyoles, diphosphatidylpolyoles, triphosphatidylpolyoles, tetraphosphatidylpolyoles and higher polyphosphatidylpolyoles. Preferably, the phosphatidylpolyoles according to the invention are selected from monophosphatidylpolyoles, diphosphatidylpolyoles and triphosphatidylpolyoles, and/or the salts thereof.

Sulfatidylpolyoles according to the invention preferably comprise mono- and pyrosulfatidylpolyoles, including, but not limited to, monosulfatidylpolyoles, disulfatidylpolyoles, trisulfatidylpolyoles, tetrasulfatidylpolyoles and higher polypsulfatidylpolyoles. Preferably, the sulfatidylpolyoles according to the invention are selected from monosulfatidylpolyoles, disulfatidylpolyoles and trisulfatidylpolyoles, and/or the salts thereof.

Preferred for use in the compositions for use in the methods according to the invention are phosphatidylpolyoles and/or sulfatidylpolyoles, wherein the polyol-substructure therein is preferably derived or selected from dioles, trioles, tetroles, pentoles and hexoles, including, but not limited to glycol, propanedioles, including, but not limited to propane-1,3-diol and propane-1,2-diol, diethylene glycol, glycerol, butanedioles, including, but not limited to butane-1,2-diol, butane-1,3-diol, butane-1,4-diol, butane-2,2-diol, butane-2,3-diol, butanetrioles, including, but not limited to 2-Hydroxymethyl-propane-1,3-diol, 2-Methyl-propane-1,2,3-triol, butane-1,2,3-triol and butane-1,2,4-triol, and 1,2,3,4-butane1,2,3,4-tetrol, including, but not limited to erythritol and threitol.

More preferred for use in the compositions for use in the methods according to the invention are phosphatidylpolyoles and/or sulfatidylpolyoles, wherein the polyol-substructure therein is preferably derived or selected from dioles, trioles and tetroles, and especially selected from trioles, preferably trioles as described above.

Generally, the fatty acid esters of polyoles are preferred over the fatty alcohol ethers of polyoles.

[11] Preferably, the phosphatidyl- or sulfatidyl-polyoles are selected from
a) polyphosphatidylglycerol, triphosphatidylglycerol, diphosphatidylglycerol and monophosphatidylglycerol, and/or
b) polysulfatidylglycerol, trisulfatidylglycerol, disulfatidylglycerol and monosulfatidylglycerol,
and/or the salts thereof.

More preferably, the phosphatidyl- or sulfatidyl-polyoles are selected from
a) triphosphatidylglycerol, diphosphatidylglycerol, monophosphatidylglycerol, especially monophosphatidylglycerol, and/or
b) polysulfatidylglycerol, trisulfatidylglycerol, disulfatidylglycerol, and monosulfatidylglycerol, especially monosulfatidylglycerol,
and/or the salts thereof.

If not explicitly referred to otherwise, monophosphatidylglycerol and monosulfatidylglycerol are preferably also referred to as phosphatidylglycerol and sulfatidylglycerol, respectively.

Especially preferably, the fatty acids are in each case independently selected from the group consisting of myristic acid, oleic acid, palmitic acid, stearic acid, margaric acid, arachic or arachidic acid, behenic acid, erucic acid, linoleic acid and linolenic acid. Even more preferably, the fatty acids are in each case independently selected from the group consisting of myristic acid, oleic acid, palmitic acid and stearic acid.

Thus, in the fatty acid esters comprising more than one fatty acid, the fatty acids can be all the same or different. For example, in a fatty acid diester, both fatty acid moieties can be the same, e.g. both oleoyl or both palmitoyl, or different, e.g. one oleoyl and one palmitoyl. Alternatively, fatty acid diesters or triesters can comprise two or more different fatty acid moieties in a mixture, e.g. a statistical mixture.

Thus, preferred amphiphilic compounds according to the invention are preferably selected from one or more of the following formulae:

i)
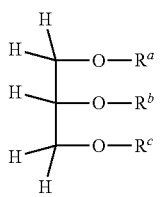

ii)
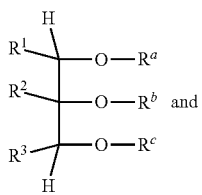
and iii)
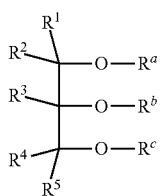

wherein
α) $R^1$, $R^2$, $R^3$, $R^4$ and $R^5$ are independently from each other are selected from H, methyl, ethyl and hydrophilic moieties, more preferably from H, methyl and ethyl; preferably with the proviso that only one or two of $R^1$, $R^2$, $R^3$, $R^4$ and $R^5$ are other than H, and more preferably that only one of $R^1$, $R^2$, $R^3$, $R^4$ and $R^5$ is other than H;
β) $R^a$, $R^b$ and $R^c$ are independently from each other are selected from H and $R^6$
wherein each $R^6$ is independently selected from the group consisting of
  i) fatty acid moieties and fatty alcohol moieties, preferably fatty acid moieties and fatty alcohol moieties as described herein and especially fatty acid moieties as described herein, and
  ii) hydrophilic moieties, preferably hydrophilic moieties as described herein;
with the proviso that one or more of $R^a$, $R^b$ and $R^c$, preferably two or more of $R^a$, $R^b$ and $R^c$ and especially all of $R^a$, $R^b$ and $R^c$ are $R^6$
and with the further proviso that only one or two, preferably only one of $R^6$ is a hydrophilic moiety;
and the salts and/or stereoisomers thereof, and preferably the salts thereof.

Thus, more preferred amphiphilic compounds according to the invention are preferably selected from the following formula:

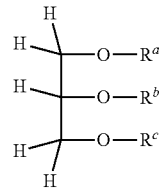

wherein
$R^a$, $R^b$ and $R^c$ are independently from each other are selected from H and $R^6$,
wherein each $R^6$ is independently selected from the group consisting of
  i) fatty acid moieties and fatty alcohol moieties, preferably fatty acid moieties and fatty alcohol moieties as described herein and especially fatty acid moieties as described herein, and
  ii) hydrophilic moieties, preferably hydrophilic moieties as described herein; with the proviso that one or more of $R^a$, $R^b$ and $R^c$, preferably two or more of $R^a$, $R^b$ and $R^c$ and especially all of $R^a$, $R^b$ and $R^c$ are $R^6$
and with the further proviso that only one or two, preferably only one of $R^6$ is a hydrophilic moiety,
and the salts and/or stereoisomers thereof, and preferably the salts thereof.

Thus, even more preferred amphiphilic compounds according to the invention are preferably selected from the following formula:

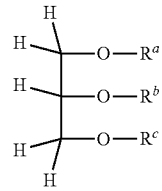

wherein
a) both $R^a$ and $R^b$ independently of each other are selected from acid moieties and fatty alcohol moieties, preferably fatty acid moieties and fatty alcohol moieties as described herein and especially fatty acid moieties as described herein, and $R^c$ is a hydrophilic moiety, preferably a hydrophilic moiety as described herein,
b) both $R^a$ and $R^c$ independently of each other are selected from acid moieties and fatty alcohol moieties, preferably fatty acid moieties and fatty alcohol moieties as described herein and especially fatty acid moieties as described herein, and $R^b$ is a hydrophilic moiety, preferably a hydrophilic moiety as described herein, or
c) both $R^b$ and $R^c$ independently of each other are selected from acid moieties and fatty alcohol moieties, preferably fatty acid moieties and fatty alcohol moieties as described herein and especially fatty acid moieties as described herein, and $R^a$ is a hydrophilic moiety, preferably a hydrophilic moiety as described herein and the salts and/or stereoisomers thereof, and preferably the salts thereof.

With regard to $R^a$, $R^b$ and/or $R^c$ the hydrophilic moieties are preferably selected from the group consisting of:
i) —$PO_3H$, —$PO_3Na$, —$PO_3K$, —$PO_3^-$;
ii) —$(PO_2$—$O)_v$—$PO_3H$, —$(PO_2$—$O)_v$—$PO_3Na$, —$(PO_2$—$O)_v$—$PO_3K$, —$(PO_2$—$O)_v$—$PO_3^-$
iii) —$SO_3H$, —$SO_3Na$, —$SO_3K$, —$SO_3^-$;
iv) —$(SO_2$—$O)_w$—$SO_3H$, —$(SO_2$—$O)_w$—$SO_3Na$, —$(SO_2$—$O)_w$—$SO_3K$, —$(SO_2$—$O)_w$—$SO_3^-$
v) —$(CH_2)_n$—$OH$, —$(CH_2)_n$—$ONa$, —$(CH_2)_n$—$OK$, —$(CH_2)_n$—$O^-$, —$(CH_2)_n$—$NH_2$, —$(CH_2)_n$—$NH_3^+$, —$(CH_2)_n$—$N(CH_3)_3^+$, —$(CH_2)_n$—$PO_3H$, —$(CH_2)_n$—$PO_3Na$, —$(CH_2)_n$—$PO_3K$, —$(CH_2)_n$—$PO_3^-$, —$(CH_2)_n$—$O$—$PO_3H$, —$(CH_2)_n$—$O$—$PO_3Na$, —$(CH_2)_n$—$O$—$PO_3K$, —$(CH_2)_n$—$O$—$PO_3^-$
vi) —$(CH_2)_n$—$(PO_2$—$O)_x$—$PO_3H$, —$(CH_2)_n$—$(PO_2$—$O)_x$—$PO_3Na$, —$(CH_2)_n$—$(PO_2$—$O)_x$—$PO_3K$, —$(CH_2)_n$—$(PO_2$—$O)_x$—$PO_3^-$,
vii) —$(CH_2)_n$—$(SO_2$—$O)_y$—$SO_3H$, —$(CH_2)_n$—$(SO_2$—$O)_y$—$SO_3Na$, —$(CH_2)_n$—$(SO_2$—$O)_y$—$SO_3K$, —$(CH_2)_n$—$(SO_2$—$O)_y$—$SO_3^-$,
wherein
n is 1, 2, 3 or 4, preferably 1, 2 or 3 and especially 1 or 2,
v is 1, 2, 3 or 4, preferably 1, 2 or 3 and especially 1 or 2,
w is 1, 2, 3 or 4, preferably 1, 2 or 3 and especially 1 or 2,
x is 1, 2, 3 or 4, preferably 1, 2 or 3 and especially 1 or 2, and
y is 1, 2, 3 or 4, preferably 1, 2 or 3 and especially 1 or 2;

and/or
γ) an ethanolamine moiety, a choline moiety, a phosphatidyl moiety, a phosphatidylcholine moiety, a sulfatidyl and a sulfatidylcholine moiety;
and a salt or other salt thereof.

With regard to $R^a$, $R^b$ and/or $R^c$ the hydrophilic moieties are even more preferably selected from the group consisting of:
i) —$PO_3H$, —$PO_3Na$, —$PO_3K$, —$PO_3^-$;
ii) —$(PO_2$—$O)_v$—$PO_3H$, —$(PO_2$—$O)_v$—$PO_3Na$, —$(PO_2$—$O)_v$—$PO_3K$, —$(PO_2$—$O)_v$—$PO_3^-$
iii) —$(CH_2)_n$—$OH$, —$(CH_2)_n$—$ONa$, —$(CH_2)_n$—$OK$, —$(CH_2)_n$—$O^-$, —$(CH_2)_n$—$NH_2$, —$(CH_2)_n$—$NH_3^+$, —$(CH_2)_n$—$N(CH_3)_3^+$, —$(CH_2)_n$—$PO_3H$, —$(CH_2)_n$—$PO_3Na$, —$(CH_2)_n$—$PO_3K$, —$(CH_2)_n$—$PO_3^-$, —$(CH_2)_n$—$O$—$PO_3H$, —$(CH_2)_n$—$O$—$PO_3Na$, —$(CH_2)_n$—$O$—$PO_3K$, —$(CH_2)_n$—$O$—$PO_3^-$,
wherein
n is 1, 2, 3 or 4, preferably 1, 2 or 3 and especially 1 or 2, and
v is 1, 2, 3 or 4, preferably 1, 2 or 3 and especially 1 or 2,
and/or
iv) an ethanolamine moiety, a choline moiety, a phosphatidyl moiety, a phosphatidylcholine moiety, a sulfatidyl and a sulfatidylcholine moiety;
and a salt or other salt thereof.

With regard to $R^a$, $R^b$ and/or $R^c$, the fatty acid moieties are preferably selected from the group of:

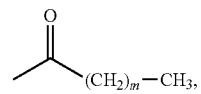

wherein m is 2 to 33, more preferably 4 to 28 and even more preferably 6 to 23;

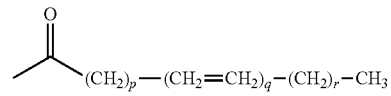

wherein
p is 1 to 20, more preferably 3 to 18, even more preferably 4 to 15 and especially 6 to 13,
q is 0 to 6, more preferably 1 to 5, more preferably 1, 2, 3, or 4 and especially 1, 2 or 3,
r is 1 to 20, more preferably 3 to 15, even more preferably 6 to 12 and especially 6, 7 or 8,
preferably with the proviso that the sum of p and r is 4 to 30, more preferably 5 to 25, even more preferably 8 to 22 and especially 10 to 20 and/or with the proviso that the sum of p, q and r is 5 to 30, more preferably 6 to 25, even more preferably 9 to 23 and especially 11 to 21;

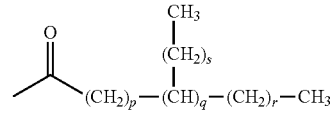

wherein
p is 1 to 20, more preferably 3 to 18, even more preferably 4 to 15 and especially 6 to 13,
q is 0 to 6, more preferably 1 to 5, more preferably 1, 2, 3, or 4 and especially 1, 2 or 3,
r is 1 to 20, more preferably 3 to 15, even more preferably 6 to 12 and especially 6, 7 or 8, and
s is 1 to 20, more preferably 1 to 15, even more preferably 1 to 10 and especially 1 to 5,
preferably with the proviso that the sum of p, r and s is 4 to 30, more preferably 5 to 25, even more preferably 8 to 22 and especially 10 to 20 and/or with the proviso that the sum of p, q, r and s is 5 to 30, more preferably 6 to 25, even more preferably 9 to 23 and especially 11 to 21; and/or

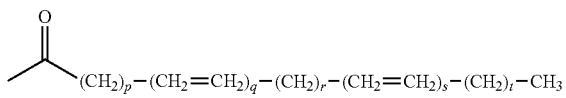

wherein
p is 1 to 20, more preferably 3 to 15, even more preferably 6 to 12 and especially 6, 7 or 8,
q is 0 to 6, more preferably 1 to 5, more preferably 1, 2, 3, or 4 and especially 1, 2 or 3,
r is 1 to 20, more preferably 3 to 18, even more preferably 4 to 15 and especially 6 to 12, and
s is 0 to 6, more preferably 1 to 5, more preferably 1, 2, 3, or 4 and especially 1, 2 or 3,
t is 1 to 20, more preferably 1 to 15, even more preferably 1 to 10, even more preferably 3 to 8 and especially 4, 5, 6, 7 or 8,
preferably with the proviso that the sum of p, r and t is 4 to 30, more preferably 6 to 25, even more preferably 8 to 22 and especially 10 to 20 and/or with the proviso that the sum of p, q, r, s and t is 5 to 30, more preferably 7 to 25, even more preferably 9 to 23 and especially 11 to 21.

With regard to $R^a$, $R^b$ and/or $R^c$, the fatty acid moieties are even more preferably selected from the group of:

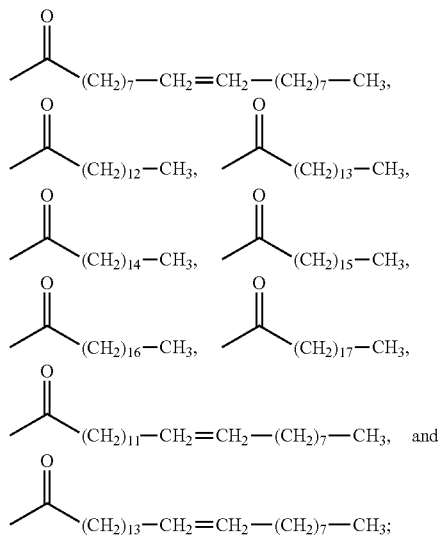

and, in case of the unsaturated fatty acid moieties, all stereoisomers thereof.

With regard to $R^a$, $R^b$ and/or $R^c$, the fatty acid moieties are even more preferably selected from the group of:
the fatty acid moieties are selected from the group consisting of myristoyl, oleoyl, palmitoyl (corresponds to palmitic acid), stearoyl, margaroyl, arachidoyl, behenoyl, erucoyl, linoleoyl and linolenoyl.

With regard to $R^a$, $R^b$ and/or $R^c$, the fatty acid moieties are selected from the group consisting of myristoyl, oleoyl, palmitoyl and stearoyl.

Especially preferred amphiphilic compounds according to the invention are preferably selected from dioleoylphosphatidylglycerol (DOPG), dimyristoylphosphatidylcholine (DMPC), distearoylphosphatidylglycerol (DSPG), dioleoylglycerophosphocholine (DOPC), dipalmitoylglycerophosphoglycerol (DPPG), distearoylglycerophosphoethanolamine (DSPE), egg phosphatidylcholine (EPC) and soy phosphatidylcholine (SPC), more preferably dioleoylphosphatidylglycerol (DOPG), dimyristoylphosphatidylglycerol (DMPG), distearoylphosphatidylglycerol (DSPG), dioleoylglycerophosphocholine (DOPC), dipalmitoylglycerophosphoglycerol (DPPG), even more preferably dioleoylphosphatidylglycerol (DOPG), dimyristoylphosphatidylglycerol (DMPG), distearoylphosphatidylglycerol (DSPG), dipalmitoylglycerophosphoglycerol (DPPG), even more preferably dioleoylphosphatidylglycerol (DOPG) and dimyristoylphosphatidylglycerol (DMPG), and especially dimyristoylphosphatidylglycerol (DMPG); and/or the salts thereof, preferably the salts described herein, and especially the alkaline and/or ammonium salts thereof. Also preferred are mixtures of said amphiphilic compounds and/or the salts thereof, preferably including mixtures of different salts of the same compound and mixtures of different salts of different compounds.

Alternatively preferred amphiphilic compounds according to the invention are amphiphilic compounds which comprise two different fatty acids, fatty acids as described herein. More preferably, these amphiphilic compounds are selected from
myristoylstearoylphosphatidylcholine (MSPC),
myristoylpalmitoylphosphatidylcholine (MPPC),
myristoyloleoylphosphatidylcholine (MOPC),
palmitoylstearoylphosphatidylcholine (PSPC),
palmitoyloleoylphosphatidylcholine (POPC),
stearoyloleoylphosphatidylcholine (SOPC),
myristoylstearoylphosphatidylglycerol (MSPG),
myristoyloleoylphosphatidylglycerol (MOPG),
myristoylpalmitoylphosphatidylglycerol (MPPG),
palmitoylstearoylphosphatidylglycerol (PSPG),
palmitoyloleoylphosphatidylglycerol (POPG),
stearoyloleoylphosphatidylglycerol (SOPG),
myristoylstearoylglycerophosphocholine (MSPC),
myristoyloleoylglycerophosphocholine (MOPC),
myristoylpalmitoylglycerophosphocholine (MPPC),
palmitoylstearoylglycerophosphocholine (PSPC),
palmitoyloleoylglycerophosphocholine (POPC),
stearoyloleoylglycerophosphocholine (SOPC),
myristoylstearoylglycerophosphoethanolamine (MSPE),
myristoyloleoylglycerophosphoethanolamine (MOPE),
myristoylpalmitoylglycerophosphoethanolamine (MPPE),
palmitoylstearoylglycerophosphoethanolamine (PSPE),
palmitoyloleoylglycerophosphoethanolamine (POPE), and
stearoyloleoylglycerophosphoethanolamine (SOPE);
and/or the salts thereof, preferably the salts described herein, and especially the alkaline and/or ammonium salts thereof. Also preferred are mixtures of said amphiphilic compounds and/or the salts thereof, preferably including mixtures of different salts of the same compound and mixtures of different salts of different compounds.

Especially preferred amphiphilic compounds and/or the salts thereof according to the invention can preferably also defined by their Chemical Abstracts Numbers (CAS-Numbers):
DOPG (sodium salt): 67254-28-8
DMPC: 18194-24-6
DMPG (sodium salt): 67232-80-8
DSPG (sodium salt): 108347-80-4
DOPC: 4235-95-4
DPPG (sodium salt): 42367232-81-9
DSPE: 1069-79-0
SPC: 97281-47-5.

Especially preferred amphiphilic compounds and/or the salts thereof according to the invention can preferably also defined by their Chemical Abstracts Numbers (CAS-Numbers):
DOPG (sodium salt): 67254-28-8, and/or
DMPG (sodium salt): 67232-80-8

From a toxicological point of view, negatively charged or uncharged amphiphilic compounds may be preferred over positively charged amphiphilic compounds (Recent advances in tumor vasculature targeting using liposomal drug delivery systems Amr S Abu Lila, Tatsuhiro Ishida, Hiroshi Kiwada, Expert Opinion on Drug Delivery, DOI 10.1517/17425240903289928.

Examples of negatively charged amphiphilic compounds include, but are not limited to:
dioleoylphosphatidylglycerol (DOPG)
dimyristoylphosphatidylglycerol (DMPG)
distearoylphosphatidylglycerol (DSPG)
dipalmitoylglycerophosphoglycerol (DPPG).

Examples of neutral amphiphilic compounds include, but are not limited to: distearoylglycerophosphoethanolamine (DSPE).

Examples of positively charged amphiphilic compounds include, but are not limited to:
dimyristoylphosphatidylcholine (DMPC)
dioleoylglycerophosphocholine (DOPC)
soy phosphatidylcholine (SPC).

A preferred amphiphilic compound according to the invention and/or for use according to the invention is dioleoylphosphatidylglycerol (DOPG) and/or the sodium salt thereof, preferably as defined by the CAS-Number 67254-28-8.

An especially preferred amphiphilic compound according to the invention and/or for use according to the invention is dimyristoylphosphatidylglycerol (DMPG) and/or the sodium salt thereof, preferably as defined by the CAS-Number 67232-80-8.

[9a] Composition as described herein and especially as described in one or more of the paragraphs numbered [1] to [8] and preferably also as described in the paragraphs relating thereto, comprising a) 7 to 80% or 12 to 90%, preferably 12 to 60%, more preferably 15 to 40% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, b) 0.01 to 60%, preferably 0.01 to 40%, more preferably 0.01 to 20%, even more preferably 0.01 to 10%, even more preferably 0.05 to 10%, even more preferably 0.05 to 5% and especially 0.1 to 10% or 0.1 to 5%, of one or more amphiphilic compounds, preferably one or more amphiphilic compounds as described herein, and c) 10 to 94.99%, preferably 30 to 89.99%, more preferably 40 to 84.99%, even more preferably 60 to 79.99% and especially 60 to 79.9 of water, with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

[9b] A Composition as described herein and especially as described in one or more of the paragraphs numbered [1] to [8] and preferably also as described in the paragraphs relating thereto, wherein said composition comprises a) 7 to 79.99%, preferably 7 to 49.99%, even more preferably 7 to 39.99% and especially 7 to 30.99% of at least one oligopeptide, b) 0.01 to 20%, preferably 0.01 to 15%, more preferably 0.01 to 10% and especially 0.01 to 5% of one or more amphiphilic compounds, c) 20 to 92.9%, preferably 50 to 92.9%, more preferably 60 to 92.9% and especially 69 to 92.9% of water, with the proviso that the sum of a), b) and c) sums up to 90 or more % of the total composition, more preferably up to 95 or more % of the total composition and especially up to 95 to 100% of the total composition. In said composition, the at least one oligopeptide is preferably selected from the group consisting of cyclo-(Arg-Gly-Asp-DPhe-NMeVal) and the pharmaceutically acceptable derivatives, solvates and/or salts thereof, preferably cyclo-(Arg-Gly-Asp-DPhe-NMeVal) and the pharmaceutically acceptable derivatives, solvates and/or salts thereof having a solubility in water at 20° C. between 1 mg/ml and 15 mg/ml and especially cyclo-(Arg-Gly-Asp-DPhe-NMeVal) in the polymorphic form A1. In said composition, the one on more amphiphilic compounds comprise or essentially consist of one or more compounds selected from the group consisting of dioleoylphosphatidylglycerol and dimyristoylphosphatidylglycerol and/or the salts thereof. Said method is especially preferred in the treatment of human subjects.

A Composition as described herein and especially as described in one or more of the paragraphs numbered [1] to [9] and preferably also as described in the paragraphs relating thereto, comprising a) 12 to 90%, preferably 15 to 80%, preferably 15 to 60%, more preferably 15 to 50% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml b) 0.01 to 60%, preferably 0.01 to 30%, more preferably 0.01 to 15%, even more preferably 0.05 to 10%, even more preferably 0.05 to 5% and especially 0.1 to 5%, of one or more amphiphilic compounds, c) 10 to 89.99%, preferably 20 to 89.99%, more preferably 30 to 84.99%, even more preferably 40 to 84.99%, even more preferably 50 to 84.95% and especially 60 to 79.95% of water, with the proviso that the sum of a), b) and c) makes up to 70 or more %, preferably 80 or more %, more preferably 90 or more %, even more preferably 95 or more % and especially 95 to 99.9% of the total composition.

Preferred in this regard are oligopeptides or cyclic oligopeptides which comprise the Arg-Gly-Asp-subsequence.

A Composition as described herein and especially as described in one or more of the paragraphs numbered [1] to

[9] and preferably also as described in the paragraphs relating thereto for use in the methods according to the invention, comprising
a) 12 to 90%, preferably 12 to 60%, more preferably 15 to 40% and especially 20 to 40% of a cyclic oligopeptide selected from cyclo-(Arg-Gly-Asp-DPhe-NMeVal), cyclo-(Arg-Gly-Asp-DPhe-Val) and the pharmaceutically acceptable derivatives, solvates and/or salts thereof, and preferably selected from cyclo-(Arg-Gly-Asp-DPhe-NMeVal) and the pharmaceutically acceptable solvates and/or salts, preferably having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml,
b) 0.01 to 60%, preferably 0.01 to 40%, more preferably 0.01 to 20%, even more preferably 0.01 to 10%, even more preferably 0.05 to 10%, even more preferably 0.05 to 5% and especially 0.1 to 10% or 0.1 to 5%, of one or more amphiphilic compounds, preferably one or more amphiphilic compounds as described herein, and
c) 10 to 94.99%, preferably 30 to 89.99%, more preferably 40 to 84.99%, even more preferably 60 to 79.99% and especially 60 to 79.9 of water,
with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

A Composition as described herein and especially as described in one or more of the paragraphs numbered [1] to [9] and preferably also as described in the paragraphs relating thereto for use in the methods according to the invention, comprising
a) 12 to 90%, preferably 12 to 60%, more preferably 15 to 40% and especially 20 to 40% of cyclo-(Arg-Gly-Asp-DPhe-NMeVal), more preferably of an anhydrate of the inner salt of cyclo-(Arg-Gly-Asp-DPhe-NMeVal) and especially of the crystalline form A1 of the inner salt of cyclo-(Arg-Gly-Asp-DPhe-NMeVal), preferably having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml,
b) 0.01 to 60%, preferably 0.01 to 40%, more preferably 0.01 to 20%, even more preferably 0.01 to 10%, even more preferably 0.05 to 10%, even more preferably 0.05 to 5% and especially 0.1 to 10% or 0.1 to 5%, of one or more amphiphilic compounds, preferably one or more amphiphilic compounds as described herein, and
c) 10 to 94.99%, preferably 30 to 89.99%, more preferably 40 to 84.99%, even more preferably 60 to 79.99% and especially 60 to 79.9 of water,
with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

[10] Alternatively preferred is a composition, preferably a pharmaceutical composition, for use in the methods according to the invention as described herein, comprising
a) 12 to 90%, preferably 12 to 60%, more preferably 15 to 40% and especially 20 to 40% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml,
b) 0.01 to 60%, preferably 0.01 to 40%, more preferably 0.01 to 20%, even more preferably 0.01 to 10%, even more preferably 0.05 to 10%, even more preferably 0.05 to 5% and especially 0.1 to 10% or 0.1 to 5%, one or more amphiphilic compounds, selected from
b1) fatty acid mono-, di- or polyesters of phosphatidyl- or sulfatidyl-polyoles, and derivatives, salts and/or alcoholates thereof, and
b2) fatty alcohol mono-, di- or polyethers of phosphatidyl- or sulfatidyl-polyoles, and derivatives, salts and/or alcoholates thereof,
c) 10 to 94.99%, preferably 30 to 89.99%, more preferably 40 to 84.99%, even more preferably 60 to 79.99% and especially 60 to 79.9 of water,
preferably with the proviso that the sum of a), b) and c) makes up to 70 or more %, preferably 80 or more %, more preferably 90 or more %, even more preferably 95% or more, even more preferably 95 to 99.9% and especially 98 to 99.9%, of the total composition.

Preferably, said oligopeptide or cyclic oligopeptide as described herein is selected from cyclo-(Arg-Gly-Asp-DPhe-NMeVal), an anhydrate of the inner salt of cyclo-(Arg-Gly-Asp-DPhe-NMeVal) and the crystalline form A1 of the inner salt of cyclo-(Arg-Gly-Asp-DPhe-NMeVal), said oligopeptide or cyclic oligopeptide preferably having a solubility in water at 20° C. between 1 mg/ml and 25 mg/ml, preferably between 2 mg/ml and 20 mg/ml, more preferably between 2 mg/ml and 15 mg/ml, even more preferably between 3 mg/ml and 10 mg/ml, and especially between 5 mg/ml and 9 mg/ml.

Even more preferably, said oligopeptide or cyclic oligopeptide as described herein is selected from cyclo-(Arg-Gly-Asp-DPhe-NMeVal), an anhydrate of the inner salt of cyclo-(Arg-Gly-Asp-DPhe-NMeVal) and the crystalline form A1 of the inner salt of cyclo-(Arg-Gly-Asp-DPhe-NMeVal), said oligopeptide or cyclic oligopeptide preferably having a solubility in water at 20° C. between 5 mg/ml and 20 mg/ml, more preferably between 5 mg/ml and 15 mg/ml, even more preferably between 6 mg/ml and 10 mg/ml, and especially between 5 mg/ml and 9 mg/ml.

[11] Composition as described herein and especially as described in the paragraphs numbered [8] and/or [10] and preferably also as described in the paragraphs relating thereto for use in the methods according to the invention as described herein, wherein the phosphatidyl- or sulfatidyl-polyoles are selected from
a) polyphosphatidylglycerol, triphosphatidylglycerol, diphosphatidylglycerol, monophosphatidylglycerol, and/or b) polysulfatidylglycerol, trisulfatidylglycerol, disulfatidylglycerol, and monosulfatidylglycerol,
and/or the salts thereof.

[12] Composition as described herein and especially as described in one or more of the paragraphs numbered [1] to [11] and preferably also as described in the paragraphs relating thereto for use in the methods according to the invention as described herein, wherein
i) the fatty acids are independently selected from the group consisting of oleic acid, myristic acid, palmitic acid, stearic acid, margaric acid, arachic acid, behenic acid, erucic acid, linolic acid and linolenic acid, and
ii) the fatty alcohols are independently selected from the group consisting of oleic alcohol, myristic alcohol, palmitic alcohol, stearic alcohol, margaric alcohol, arachic alcohol, behenic alcohol, erucic alcohol, linolic alcohol and linolenic alcohol,
iii) the fatty acid moieties are independently selected from the acyl residues of the fatty acids according to a), and/or
iv) the fatty alcohol moieties are independently selected from the alkyl residues of the fatty alkohols according to ii).

[13] Composition as described herein and especially as described in one or more of the paragraphs numbered [1] to [11] and/or preferably also as described in the paragraphs relating thereto for use in the methods according to the invention as described herein, wherein amphiphilic compounds and/or the fatty acid di- or polyesters of polyphosphatidyl-polyoles are selected from the group consisting of dioleoylphosphatidylglycerol, dimyristoylphosphatidylcholine, distearoylphosphatidylglycerol, dioleoylglycerophosphocholine, dipalmitoylglycerophosphoglycerol, distearoylglycerophosphoethanolamine, egg phosphatidylcholine and soy phosphatidylcholine,
and the pharmaceutically acceptable derivatives, salts and/or alcoholates thereof.

A Composition as described herein and especially as described in one or more of the paragraphs numbered [1] to [13] and/or preferably also as described in the paragraphs relating thereto for use in the methods according to the invention as described herein, wherein amphiphilic compounds and/or the fatty acid di- or polyesters of polyphosphatidyl-polyoles are selected from the group consisting of dioleoylphosphatidylglycerol, dimyristoylphosphatidylglycerol, dimyristoylphosphatidylcholine, distearoylphosphatidylglycerol, dioleoylglycerophosphocholine, dipalmitoylglycerophosphoglycerol,
distearoylglycerophosphoethanolamine, egg phosphatidylcholine and soy phosphatidylcholine, more preferably dioleoylphosphatidylglycerol and/or dimyristoylphosphatidylglycerol, and especially dimyristoylphosphatidylglycerol, and the pharmaceutically acceptable derivatives, salts and/or alcoholates thereof.

[14] A method as described herein and especially as described in one or more of the paragraphs numbered [1] to [13]] and/or preferably also as described in the paragraphs relating thereto, wherein in said composition the amphiphilic compounds and/or the fatty acid di- or polyesters of polyphosphatidyl-polyoles are selected from the group consisting of dioleoylphosphatidylglycerol and dimyristoylphosphatidylglycerol, and the pharmaceutically acceptable derivatives, salts and/or alcoholates thereof.

If the composition for use in the methods according to the invention as described herein comprises compounds and/or excipients other than a), b) and c), said compounds and/or excipients are preferably selected from further active ingredients, preferably further pharmaceutically active ingredients, and further excipients and/or auxilliaries, preferably pharmaceutically acceptable excipients and/or auxilliaries. Excipients and/or auxilliaries and especially pharmaceutically acceptable excipients and/or auxilliaries are known in the art, e.g. from Europäisches Arzneibuch, 6. Ausgabe, CD-ROM Official German Edition, US Pharmacopeia 29, European Pharmacopeia, and/or Deutsches Arzneimittelbuch, preferably in the respective current version or newer.

Preferably, the compositions for use in the methods according to the invention as described herein do not comprise active ingredients other than the oligopeptides as defined herein.

More preferably, the compositions for use in the methods according to the invention as described do not comprise further pharmaceutically active ingredients other than the oligopeptides as defined herein.

Preferred excipients include, but are not limited to tonicity agents and/or preservatives. Preservatives in this regard preferably are antimicrobial preservatives.

Examples of preservatives, preferably pharmaceutically acceptable preservatives are known in the art, e.g. from Swarbrick, Pharmaceutical Technology.

Examples of pharmaceutically acceptable preservatives are given in the table below:

TABLE 1

Commonly used preservatives and their preferred route of administration:

| Preservative | Preferred route of administration |
| --- | --- |
| Benzalkonium chloride | IM, inhalation, nasal, ophthalmic, otic, topical |
| Benzethonium chloride | IM, IV, ophthalmic, otic |
| Benzoic acid | IM, IV, irrigation, oral, rectal, topical, vaginal |
| Benzyl alcohol | Injections, oral, topical, vaginal |
| Bronopol | Topical |
| Butylparaben | Injections, oral, rectal, topical |
| Cetrimide | Topical, ophthalmic |
| Chlorhexidine | Topical, ophthalmic |
| Chlorobutanol | IM, IV, SC, inhalation, nasal, otic, ophthalmic, topical |
| Chlorocresol | Topical |
| Cresol | IM, intradermal, SC, topical |
| Ethylparaben | Oral, topical |
| Imidurea | Topical |
| Methylparaben | IM, IV, SC, ophthalmic, oral, otic, rectal, topical, vaginal |
| Phenol | Injections |
| Phenoxyethanol | Topical |
| Phenylethyl alcohol | Nasal, ophthalmic, otic |
| Phenylmercuric acetate/borate | Ophtalmic |
| Phenylmercuric nitrate | IM, ophthalmic, topical |
| Propylparaben | IM, IV, SC, inhalation, ophthalmic, oral, otic, rectal, topical, vaginal |
| Sodium benzoate | Dental, IM, IV, oral, rectal, topical |
| Sodium propionate | Oral |
| Sorbic acid | Oral, topical |
| Thimerosal | IM, IV, SC, ophthalmic, otic, topical |

Preferred preservatives, especially preferred preservatives for s.c. formulations, are selected from the group consisting of benzyl alcohol, phenol, cresol and cresol derivatives, e.g. chlorocresol, preferably selected from the group consisting of phenol, cresol and chlorocresol. Especially preferred is phenol.

Examples of tonicity agents, preferably pharmaceutically acceptable tonicity agents are known in the art, e.g. from Swarbrick, Pharmaceutical Technology.

Preferred tonicity agents are selected from the group consisting of alkali salts, preferably sodium chloride and/or potassium chloride, ammonium chloride, glycerol, sugars, preferably glucose and/or fructose, and urea.

However, suitable alternatives to the above given tonicity agents are known to the skilled artisan.

Especially preferred as tonicity agent is sodium chloride (NaCl).

Thus, in the context of the present invention, the water according to c) of the composition can optionally be substituted, partially or totally, by isotonic saline or physiologic saline, e.g. saline for infusion. In the context of the instant invention, the isotonic saline, physiologic saline or saline for infusion is preferably a solution of about 0.9 weight % of NaCl in water. More preferably, the composition is made using water (c)) and the tonicity is adjusted by addition of NaCl as a preferred excipient after the compounds according to a) and/or b) are added, if applicable.

Thus, tonicity agents and/or preservatives are preferred excipients according to d) and especially according to d2).

[15] Composition as described herein and especially as described in one or more of the paragraphs numbered [1] to [14] and/or preferably also as described in the paragraphs relating thereto, comprising
d) 0 to 50% of one or more compounds other than a), b) and c), selected from
d1) pharmaceutically active ingredients,
d2) pharmaceutically acceptable excipients;
preferably with the proviso that the sum of a), b), c) and d) makes up to 80% or more, preferably 90% or more, more preferably 95% or more, and especially 95 to 99.9% or 95 to 100% of the total composition.

[16] Composition as described herein and especially as described in one or more of the paragraphs numbered [1] to [15] and/or preferably also as described in the paragraphs relating thereto, comprising
d) 0 to 10% of one or more compounds other than a), b) and c), selected from pharmaceutically acceptable excipients (d2);
preferably with the proviso that the sum of a), b), c) and d2) and preferably a), b), c) and d) makes up to 80% or more, preferably 90% or more, more preferably 95% or more, and especially 95 to 99.9% or 95 to 100% of the total composition.

Thus, especially preferred is a composition as described herein, comprising
a) one or more oligopeptides as described herein in the amounts as described herein,
b) one or more amphiphilic compounds as described herein in the amounts as described herein,
c) water in the amounts as described herein, and
d) one or more compounds selected from
d1) 0 to 20%, preferably 0 to 10% and especially no or essentially no pharmaceutically active ingredients other than the oligopeptides according to a), and
d2) 0 to 20%, preferably 0.01 to 10%, more preferably 0.05 to 10%, even more preferably 0.1 to 10% and especially 0.1 to 5% of one or more, preferably two or more and especially 1, 2 or 3 pharmaceutically acceptable excipients,
preferably with the proviso that the sum of a), b), c) and d) makes up to 80 or more %, preferably 90 or more %, more preferably 95% or more, even more preferably 95 to 99.9%, even more preferably 98 to 99.9% and especially 99 to 100%, of the total composition.

Especially preferably, the above described compositions consists or essentially consists of a), b), c) and d).

Thus, also preferred for use in the methods according to the invention is a composition, comprising, preferably essentially consisting of and especially consisting of:
a) 7 to 50% or 12 to 60% of at least one oligopeptide as described herein, more preferably of at least cyclic oligopeptide as described herein and especially at least one cyclic oligo peptide, selected from the group consisting of cyclo-(Arg-Gly-Asp-DPhe-NMeVal), cyclo-(Arg-Gly-Asp-DPhe-Val),
and the pharmaceutically acceptable derivatives, solvates and/or salts thereof,
b) 0.01 to 30%, preferably 0.01 to 10% and especially 0.05 to 5% of one or more amphiphilic compounds, preferably amphiphilic compounds as described herein, more preferably selected from
b1) fatty acid di- or polyesters of phosphatidyl- or sulfatidyl-polyoles and
b2) fatty acid di- or polyethers of phosphatidyl- or sulfatidyl-polyoles, and derivatives, salts and/or alcoholates thereof,
c) 20 to 89.99% of water, and optionally
d) 0 to 50%, preferably 0 to 20%, more preferably 0.001 to 20%, even more preferably 0.01 to 10% and especially 0.1 to 5%, of one or more compounds other than a), b) and c), selected from
d1) pharmaceutically active ingredients,
d2) pharmaceutically acceptable excipients, more preferably selected from d2) pharmaceutically acceptable excipients.

Preferably, the composition for use in the methods according the invention contains at least a part or a portion of the one or more oligopeptides as solid particles, preferably suspended or suspendable solid particles.

More preferably, the composition for use in the methods according the invention contains at least a part or a portion of the one or more oligopeptides as solid micro particles, preferably suspended or suspendable solid micro particles.

Even more preferably, the composition for use in the methods according the invention contains at least a part or a portion of the one or more oligopeptides as solid particles having a particle size less than 250 µm, preferably less than 150 µm, more preferably less than 100 µm, even more preferably less than 50 µm.

Even more preferably, the composition for use in the methods according the invention contains at least a part or a portion of the one or more oligopeptides as suspended or suspendable solid micro particles having a particle size less than 250 µm, preferably less than 150 µm, more preferably less than 100 µm, even more preferably less than 50 µm.

Typically, the suspended or suspendable solid micro particles of the one or more oligopeptides contained in said compositions have a particle size of more than 0.001 µm, preferably more than 0.01 µm and especially more than 0.1 µm. However, even smaller particle sizes are preferably not critical for the compositions according to the invention. Preferably, the compositions as described herein preferably contain only minor amounts of suspended or suspendable solid micro particles of the one or more oligopeptides having a particle size of 0.01 µm or less, preferably 0.1 µm or less, and especially 1 µm or less. Minor amounts in this regard are preferably 10% or less, 5% or less, 1% or less, 0.1% or less, or 0.01% or less, based on the total amount of the one or more oligopeptides as described herein contained in said composition. Percentages in this regard are preferably % w/w. Preferably, the particle size distributions of the suspended or suspendable solid micro particles of the one or more oligopeptides contained in said compositions are characterised by d(10)=1-10 µm, d(50)=10-25 µm and/or d(90)= 25-60 µm, more preferably by d(10)=1-10 µm, d(50)=10-25 µm and d(90)=25-60 µm.

Alternatively preferably, the particle size distributions of the suspended or suspendable solid micro particles of the one or more oligopeptides contained in said compositions are characterised by d(10)=1-5 µm, d(50)=5-10 µm and/or d(90)=20-30 µm, more preferably by d(10)=1-5 µm, d(50)= 5-10 µm and d(90)=20-30 µm.

Thus, especially preferred are compositions as described herein for use in the methods according to the invention, wherein the effective average particle size of the one or more oligopeptides contained in said compositions is in the range of 5 µm to 250 µm, preferably 5 µm to 150 µm, more preferably 10 µm to 250 µm, even more preferably 10 µm to 150 µm, even more preferably 10 µm to 100 µm and even more preferably 15 µm to 100 µm, and especially 20 µm to 100 µm.

Thus, especially preferred are compositions as described herein for use in the methods according to the invention, preferably characterized or additionally characterized by a particle size of the one or more oligopeptides contained in said compositions having a d(90) value in the range of 5 µm to 150 µm, preferably 5 µm to 100 µm, more preferably 10 µm to 100 µm, even more preferably 15 µm to 100 µm, even more preferably 25 µm to 100 µm and even more preferably 20 µm to 50 µm, for example a d(90) of about 15 µm, a d(90) of about 20 µm, a d(90) of about 25 µm, a d(90) of about 30 µm, a d(90) of about 35 µm, a d(90) of about 40 µm or a d(90) of about 50 µm.

[17] Thus, preferred for use in the methods according to the invention are compositions as described herein or as described in one or more of the paragraphs numbered [1] to [16] and/or the paragraphs relating thereto, wherein 10% or more, preferably 20 percent or more, more preferably 40%, even more preferably 60% or more, even more preferably 80% or more and especially 90% or more of the contained oligopeptide according to a) is present in the composition in a suspended or suspendable solid form at a temperature of 20° C. or at a temperature of 25° C., preferably at a temperature of 20° C. Preferably, the oligopeptide according to a) that is present in the composition in a suspended or suspendable solid form has a particle size as given above and preferably a particle size in the range between 0.1 to 150 µm and especially a particle size in the range between 1 and 100 µm.

Thus, preferred for use in the methods according to the invention are compositions as described herein, wherein 20 to 99.9%, preferably 40 to 99.9%, more preferably 60 to 99.9%, even more preferably 80 to 99.9% and especially 85 to 99% of the contained oligopeptide according to a) is present in the composition in a suspended or suspendable solid form at a temperature of 20° C. or at a temperature of 25° C., preferably at a temperature of 20° C. Preferably, the oligopeptide according to a) that is present in the composition in a suspended or suspendable solid form has a particle size as given above and preferably a particle size in the range between 0.1 to 150 µm and especially a particle size in the range between 1 and 100 µm.

Thus, preferred for use in the methods according to the invention are compositions as described herein, wherein 70 to 99%, preferably 80 to 98%, more preferably 85 to 97%, even more preferably 90 to 98% and especially 95 to 98% of the contained oligopeptide according to a) is present in the composition in a suspended or suspendable solid form at a temperature of 20° C. or at a temperature of 25° C., preferably at a temperature of 20° C. Preferably, the oligopeptide according to a) that is present in the composition in a suspended or suspendable solid form has a particle size as given above and preferably a particle size in the range between 0.1 to 150 µm and especially a particle size in the range between 1 and 100 µm.

Thus, a preferred aspect of the instant invention relates to compositions as described herein for use in the methods according to the invention which are in the form of suspensions.

Suspensions in the context of the instant invention are preferably dispersed systems, comprising a disperse or dispersed phase, preferably as the discontinuous phase, which preferably consists of solid particles, and a liquid continuous phase, which acts as the dispersing agent. Typically, such suspensions comprise 0.5 to 90%, more preferably 0.5 to 60% and even more preferably 1 to 40% solid particles. Typically, the particle size of the solid particles in the said suspension is in the range between 0.1 and 200 µm, more preferably 0.1 and 150 µm and especially 1 to 100 µm. In the suspensions according to the invention, the continuous phase which acts as the dispersing agent is preferably liquid at about 20° C. or about 25° C., preferably at about 20° C. Even more preferably said continuous phase which acts as the dispersing agent is preferably liquid at a temperature of 10° C. and more preferably at a temperature of 0° C. Thus, the suspensions according to the invention are preferably liquid in a temperature range between 20° C. and 40° C., more preferably 10° C. and 40° C. and especially in the range of 0° C. and 40° C.

Preferably, the oligopeptide in suspended or suspendable solid form is present
a) partly, essentially totally or totally in the form of an amorphous solid, preferably partly, essentially totally or totally in the form of amorphous solid particles,
b) partly, essentially totally or totally in the form of a crystalline solid, preferably partly, essentially totally or totally in the form of crystalline particles,
c) partly, essentially totally or totally in the form of a mixture of amorphous and crystalline forms in one solid, preferably partly, essentially totally or totally in the form of a mixture of amorphous and crystalline solid in one particle,
and mixtures thereof.

Preferably, the (solid) particles of the oligopeptide is present:
a) partly, essentially totally or totally in the form amorphous solid particles,
b) party, essentially totally or totally in the form of crystalline particles,
c) partly, essentially totally or totally in the form of a mixture of amorphous and crystalline solid in one party,
and mixtures thereof.

Even more preferably, the oligopeptide in suspended or suspendable solid form and/or the (solid) particles of the oligopeptide, preferably the oligopeptide as described herein and especially cyclo-(Arg-Gly-Asp-DPhe-NMeVal), that are preferably present in the compositions according to the invention, are present
a) partly, essentially totally or totally in the form of a mixture of amorphous and crystalline solid in one particle,
b) party, essentially totally or totally in the form of crystalline particles, and mixtures thereof,
and especially preferably are present
partly, essentially totally or totally in the form of crystalline particles.

Especially preferably, the cyclo-(Arg-Gly-Asp-DPhe-NMeVal) that is preferably present in the compositions according to the invention in suspended or suspendable solid form and/or the (solid) particles, preferably suspended or suspendable (solid) particles, is present partly, essentially totally or totally in the form of crystalline particles.

Thus, especially preferably, the cyclo-(Arg-Gly-Asp-DPhe-NMeVal) that is preferably present in the compositions according to the invention in suspended or suspendable solid form and/or (solid) particles, preferably in the form of suspended or suspendable (solid) particles, is present partly, essentially totally or totally in the form the solid materials as described herein, even more preferably the solid materials as described herein comprising or containing the solid form A1.

Thus, especially preferred for use in the methods according to the invention are compositions that contain cyclo-(Arg-Gly-Asp-DPhe-NMeVal) in the form of suspended or suspendable (solid) particles comprising or essentially consisting of the solid materials described herein and even more preferably the solid materials as described herein comprising or essentially consisting of the solid form A1.

Thus, especially preferred for use in the methods according to the invention are compositions that contain cyclo-(Arg-Gly-Asp-DPhe-NMeVal) in the form of suspended or suspendable (solid) particles comprising or essentially consisting of a solid material having a melting/decomposition temperature of higher than 250° C. and/or a solubility in water, preferably determined as described herein, in the range between 6 and 12 mg/ml.

Thus, especially preferred for use in the methods according to the invention are compositions that contain the inner salt of cyclo-(Arg-Gly-Asp-DPhe-NMeVal) in the form of suspended or suspendable (solid) particles comprising or essentially consisting of a solid material having a melting/decomposition temperature of higher than 250° C. and/or a solubility in water, preferably determined as described herein, in the range between 6 and 12 mg/ml.

Thus, especially preferred for use in the methods according to the invention are compositions that contain the inner salt of cyclo-(Arg-Gly-Asp-DPhe-NMeVal) in the form of suspended or suspendable (solid) particles comprising or essentially consisting of a solid material described herein as A1, form A1, solid form A1, crystalline form A1 and/or polymorphic form A1.

The compositions that comprise such suspended or suspendable (solid) particles preferably show an advantageous sustained release profile.

The compositions that comprise such suspended or suspendable (solid) particles preferably also show an advantageous fast onset profile.

Physical principles and methods for producing or obtaining such solid materials or preferably such (solid) particles of the oligopeptides or cyclic oligopeptides are known in the art. As described herein, such particles preferably are formed spontaneously by contacting said oligopeptide or cyclic oligopeptide with the other components of the compositions according to the invention, preferably including the one or more lipophilic compounds or alternatively including the one or more amphiphilic compounds, the latter preferably in the presence of water. This spontaneous formation can preferably be improved and/or accelerated by exposure of the system to moderate mechanical energy, such as stirring or shaking. However, a plurality of alternative methods are known in the art. These alternative methods preferably include one or more methods, selected from the group consisting of milling, such as jet milling, pearl milling, ball milling, hammer milling, fluid energy milling, grinding, such as dry grinding or wet grinding, precipitation, such as micro-precipitation, emulsion precipitation, solvent/antisolvent precipitation, phase inversion precipitation, pH shift precipitation, temperature shift precipitation, solvent evaporation precipitation, solvent evaporation precipitation, and the like. Suitable such processes are described in the art, e.g., in WO 2004/103348.

In the compositions for use in the methods according to the invention, the weight ratio between the oligopeptides according to a) as defined herein and the lipophilic compounds b) as defined herein is preferably in the range between 1:8 and 2:3, more preferably in the range between 1:8 and 1:2, even more preferably in the range between 1:7 and 1:2 and especially in the range between 1:6 and 1:3 Especially preferably, said weight ratio is about 1:5, about 1:4 or about 1:3.

In the compositions for use in the methods according to the invention, the weight ratio between the oligopeptides according to a) as defined herein and the amphiphilic compounds b) as defined herein is preferably in the range between 3000:1 and 3:1, more preferably in the range between 1500:1 and 5:1, even more preferably in the range between 1000:1 and 10:1, even more preferably in the range between 500:1 and 15:1 and especially in the range between 400:1 and 15:1 Especially preferably, said weight ratio is about 300:1, about 200:1, about 100:1, about 75:1, about 50:1, about 30:1, about 20:1 or about 15:1.

In the compositions for use in the methods according to the invention that comprise the amphiphilic compounds b) as defined herein and especially in the compositions according to the invention that comprise the amphiphilic compounds b) as defined herein in the amounts given in the paragraph above and also comprise water according to c), the weight ratio between the oligopeptides according to a) and the water according to c) contained in said composition is preferably in the range between 1:8 and 2:3, more preferably in the range between 1:7 and 1:2 and especially in the range between 1:6 and 1:3. Especially preferably, said weight ratio is about 1:1, about 1:7, about 1:6, about 1:5, about 1:4, about 1:3 or about 3:6.

The composition for use in the methods according to the invention, preferably the pharmaceutical composition for use in the methods according to the invention, comprises at least one oligopeptide, preferably as the main ingredient or one of the main ingredients of said composition. In said compositions and especially said pharmaceutical compositions, said at least one oligopeptide is the active ingredient or one of the active ingredients of said compositions. Preferably, said compositions comprise at least 12%, more preferably at least 20%, of the one or more oligopeptides, based on the total composition. Generally, the content of the one or more oligopeptides in said composition is 80% or less, more preferably 50% or less and especially preferably 40% or less, based on the total composition.

If not explicitly stated otherwise, the percentages (%) given with respect to the instant invention and especially the percentages (%) given with respect to the compositions according to the invention are preferably selected from
i) percent by weight (% by weight or % w/w),
ii) percent by volume (% by volume or % v/v), and
iii) percent weight by volume (% weight by volume or % w/v, e.g. % mg/mL or % g/mL).

For ease of use, percent by weight and percent weight by volume are preferred and percent weight by volume is especially preferred, especially with respect to the compositions according to the invention.

Oligopeptides for use in the compositions for use in the methods according to the invention preferably comprise 3 to 20 amino acids, more preferably 4 to 15 and especially 3 to 10 amino acids. The amino acids are preferably selected from naturally occurring amino acids, synthetic amino acids and/or synthetically modified naturally occurring amino acids. Naturally occurring amino acids, synthetic amino acids and/or synthetically modified naturally occurring amino acids are known to the skilled artisan. Preferably, said naturally occurring amino acids, synthetic amino acids and/or synthetically modified naturally occurring amino acids are as defined herein.

Preferably, the oligopeptide for use in the compositions for use in the methods according to the invention is a cyclic oligopeptide, more preferably a homodetic cyclic oligopeptide.

More preferably, the oligopeptide for use in the compositions for use in the methods according to the invention is a cyclic oligopeptide, more preferably a cyclic homodetic oligopeptide, that comprises an Arg-Gly-Asp-motif, Arg-Gly-Asp-sequence or Arg-Gly-Asp-subsequence. The Arg-Gly-Asp-motif, Arg-Gly-Asp-sequence or Arg-Gly-Asp-subsequence is preferably also referred to as RGD-motif, RGD-sequence or RGD-subsequence. In the context of the present intervention, these terms are preferably regarded as equivalent or as synonyms.

More preferably, the oligopeptide, even more preferably the cyclic oligopeptide and especially preferably the homodetic cyclic oligopeptide for use in the compositions for use in the methods consists of 2 to 6 naturally occurring amino acids and 0 to 4 amino acids, selected from synthetic amino acids or synthetically modified naturally occurring amino acids. More preferably, said oligopeptide consists of 3 to 6 naturally occurring amino acids and 1 to 4 amino acids, selected from synthetic amino acids or synthetically modified naturally occurring amino acids. Even more preferably, said oligopeptide consists of 3 to 5 naturally occurring amino acids and 2 to 3 amino acids, selected from synthetic amino acids or synthetically modified naturally occurring amino acids. Especially preferably, said oligopeptide consists of 2 to 4 naturally occurring amino acids, 1 or 2 synthetic amino acids and 1 or 2 synthetically modified naturally occurring amino acids. Said oligopeptide, more preferably said cyclic oligopeptide and especially said homodetic cyclic oligopeptide is preferably also referred to as "one or more compounds a)", "compound a)" and or "a)", if not defined otherwise.

Generally, the term "non-naturally occurring amino acids" is preferably intended to include any small molecule having at least one carboxyl group and at least one primary or secondary amino group capable of forming a peptide bond. The term "peptide" is preferably intended to include any molecule having at least one peptide bond. The term "peptide" preferably also embraces structures as defined above having one or more linkers, spacers, terminal groups or side chain groups which are not amino acids.

According to the invention, the naturally occurring amino acids are preferably selected from the group consisting of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, and more preferably exclusively selected from the L forms thereof.

According to the invention, the non-naturally occurring amino acids or synthetically modified naturally occurring amino acids are preferably selected from the group consisting of:

i) the D forms of naturally occurring amino acids, i.e. the D forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, ii) the N-alkyl derivatives of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, preferably including both the D and L forms thereof, and iii) Lys(Ac), Lys(AcNH$_2$), Lys(AcSH), Tic, Asp(OR), Cha, Nal, 4-Hal-Phe, homo-Phe, Phg, Pya, Abu, Acha, Acpa, Aha, Ahds, Aib, Aos, N—Ac-Arg, Dab, Dap, Deg, hPro, Nhdg, homoPhe, 4-Hal-Phe, Phg, Sar, Tia, Tic and Tle, preferably including both the D and L forms thereof;

wherein

R is alkyl having 1-18 carbon atoms, preferably alkyl having 1-6 carbon atoms and especially alkyl having 1-4 carbon atoms, Hal is F, Cl, Br, I Ac is alkanoyl having 1-10 and more preferably 1-6 carbon atoms, aroyl having 7-11 carbon atoms or aralkanoyl having 8-12 carbon atoms.

With respect to the N-alkyl derivatives of said amino acids, alkyl is preferably selected from methyl, ethyl, isopropyl, n-butyl, sec-butyl and tert-butyl. However, alkyl is furthermore also preferably selected from n-pentyl, isopentyl, neopentyl, n-hexyl, n-heptyl, n-octyl, n-nonyl, n-decyl and n-hexadecyl.

According to the invention, the non-naturally occurring amino acids are preferably selected from the group consisting of the D forms of naturally occurring amino acids, i.e. the D forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val.

According to the invention, the synthetically modified naturally occurring amino acids are preferably selected from the group consisting of the N-alkyl derivatives of the L forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val, wherein the N-alkyl residues preferably consist of 1-18 carbon atoms, more preferably 1-6 carbon atoms and even more preferably 1-4 carbon atoms.

According to the invention, the synthetically modified naturally occurring amino acids are preferably selected from the group consisting of the N-methyl derivatives and/or N-ethyl derivatives of the L forms of Gly, Ala, β-Ala, Asn, Asp, Arg, Cys, Gln, Glu, His, Ile, Leu, Lys, Met, Nle, Orn, Phe, Pro, Ser, Thr, Trp, Tyr and Val. Especially preferably, the synthetically modified naturally occurring amino acids are selected from the group consisting of the L forms of N-Methyl-Gly, N-Methyl-Ala, N-Methyl-β-Ala, N-Methyl-Asn, N-Methyl-Asp, N-Methyl-Arg, N-Methyl-Cys, N-Methyl-Gln, N-Methyl-Glu, N-Methyl-His, N-Methyl-Ile, N-Methyl-Leu, N-Methyl-Lys, N-Methyl-Met, N-Methyl-Nle, N-Methyl-Orn, N-Methyl-Phe, N-Methyl-Pro, N-Methyl-Ser, N-Methyl-Thr, N-Methyl-Trp, N-Methyl-Tyr and N-Methyl-Val, which are preferably also referred to as NMeGly, NMeAla, NMeβ-Ala, NMeAsn, NMeAsp, NMeArg, NMeCys, NMeGln, NMeGlu, NMeHis, NMeIle, NMeLeu, NMeLys, NMeMet, NMeNle, NMeOrn, NMePhe, NMePro, NMeSer, NMeThr, NMeTrp, NMeTyr and NMeVal.

It is well within the skill in the art to prepare cyclic peptides, as well cyclic peptides being comprised of naturally occurring amino acids exclusively as cyclic peptides comprising non-natural amino acids.

According to the invention, said cyclic peptide or cyclic oligopeptide is preferably a homodetic cyclic peptide or homodetic cyclic oligopeptide. The meaning of the terms "homodetic", "homodetic cyclic peptide" and homodetic cyclic oligopeptide is known in the art. According to the invention, a homodetic cyclic peptide or homodetic cyclic oligopeptide preferably is a cyclic peptide in which the ring (or backbone of the cyclic peptide) consists solely of amino-acid residues in peptide linkage (or in eupeptide linkage according to the nomenclature of the IUPAC).

Especially preferably, said cyclic oligopeptide comprises the Arg-Gly-Asp sequence (or RGD sequence in the one letter code for amino acids). According to the invention, the Arg-Gly-Asp sequence is preferably comprised exclusively of the respective L-amino acids, i.e comprised of L-Arg, L-Gly and L-Asp.

According to the invention, the cyclic peptides that comprise the Arg-Gly-Asp sequence preferably comprise Arg, Gly and Asp in the natural L configuration.

Especially preferred with respect to the invention is the cyclic peptide according to formula Ic, cyclo-(Arg-Gly-Asp-DPhe-Val)　　　　　Ic, and/or the derivatives, salts and solvates thereof, preferably the pharmaceutically acceptable derivatives, salts and/or solvates thereof, and especially the pharmaceutically acceptable salts and/or solvates thereof.

Even more preferred with respect to the invention is the cyclic peptide according to formula Id, cyclo-(Arg-Gly-Asp-DPhe-NMeVal)　　　Id, and/or the derivatives, salts and solvates thereof, preferably the pharmaceutically acceptable derivatives, salts and/or solvates thereof, and especially the pharmaceutically acceptable salts and/or solvates thereof.

The cyclic peptides according the invention and especially the cyclic peptides according to Ic and/or Id, and also the starting materials for their preparation are preferably prepared by known methods, preferably as described in the literature (for example in the standard works such as Houben-Weyl, Methoden der organischen Chemie [Methods of Organic Chemistry], Georg-Thieme-Verlag, Stuttgart), in particular under reaction conditions which are known and appropriate for the said reactions. In this context, use can also be made of known variants which are not mentioned in any greater detail here.

A base of a cyclic peptide according to the invention and especially the days of a cyclic peptide according to formula Ic and/or Id can be converted into the associated acid addition salt using an acid. Suitable acids for this reaction are, in particular, those which yield physiologically acceptable salts. Thus inorganic acids can be used, examples being sulfuric acid, nitric acid, hydrohalic acids such as hydrochloric acid or hydrobromic acid, phosphoric acid such as orthophosphoric acid, sulfamic acid, and also organic acids, especially aliphatic, alicyclic, araliphatic, aromatic or heterocyclic mono- or polybasic carboxylic, sulfonic or sulfuric acids, for example formic acid, acetic acid, propionic acid, pivalic acid, diethyl-acetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, laurylsulfuric acid. Salts with physiologically unacceptable acids, for example picrates, can be used for isolating and/or purifying the compounds of the formula I.

Alternatively, an acid of a cyclic peptide according to the invention and especially an acid of a cyclic peptide according to formula Ic and/or Id can be converted into one of its physiologically acceptable metal or ammonium salts by reaction with a base. Particularly suitable salts in this context are the sodium, potassium, magnesium, calcium and ammonium salts, and also substituted ammonium salts, for example the dimethyl-, diethyl- or diisopropylammonium salts, monoethanol-, diethanol- or triethanolammonium salts, cyclohexylammonium salts, dicyclohexylammonium salts, dibenzylethylenediammonium salts, and also, for example, salts with N-methyl-D-glucamine or with arginine or lysine.

According to the invention, the at least one cyclopeptide preferably comprises cyclo-(Arg-Gly-Asp-DPhe-NMeVal) and/or cyclo-(Arg-Gly-Asp-DPhe-Val),
and/or a salt or solvate thereof.

According to the invention, the at least one cyclopeptide is especially preferably selected from cyclo-(Arg-Gly-Asp-DPhe-NMeVal) and cyclo-(Arg-Gly-Asp-DPhe-Val), and/or a salt or solvate thereof.

Especially preferably, the at least one cyclopeptide preferably is cyclo-(Arg-Gly-Asp-DPhe-NMeVal) and/or a salt or solvate thereof.

The peptide of the formula Cyclo-(Arg-Gly-Asp-DPhe-NMeVal) is preferably employed as a pharmaceutically acceptable salt, more preferably the pharmacologically acceptable hydrochloride salt, and especially preferably applied as the inner (or internal) salt, which is the compound cyclo-(Arg-Gly-Asp-DPhe-NMeVal) as such.

With regard to the peptide of the formula cyclo-(Arg-Gly-Asp-DPhe-NMeVal), the following kinds of writing the name are preferably to be regarded as equivalent: Cyclo-(Arg-Gly-Asp-DPhe-NMeVal)=cyclo-(Arg-Gly-Asp-DPhe-NMeVal)=cyclo-(Arg-Gly-Asp-DPhe-[NMe]Val)=cyclo-(Arg-Gly-Asp-DPhe-[NMe]-Val)=cyclo-(Arg-Gly-Asp-DPhe-NMeVal)=cyclo-(Arg-Gly-Asp-DPhe-NMe-Val)= cyclo(Arg-Gly-Asp-DPhe-NMeVal)=cyclo(Arg-Gly-Asp-DPhe-NMe-Val)=cRGDfNMeV=c(RGDfNMeV).

The peptide of the formula cyclo-(Arg-Gly-Asp-DPhe-NMeVal) is preferably also referred to as Cilengitide, which is the INN (International Non-propriety Name) of said compound.

The peptide of the formula cyclo-(Arg-Gly-Asp-DPhe-NMeVal) is also described in EP 0 770 622 A, U.S. Pat. No. 6,001,961, WO 00/15244 and PCT/US07/01446 of the same applicant, the disclosure of which is explicitly incorporated into the instant application by reference.

The oligopeptides, preferably the cyclic oligopeptides for use in the compositions for use according to the invention and especially the cyclic oligopeptides according to formula I, Ia, Ib, Ic and/or Id possess very valuable properties. In particular, they act as integrin inhibitors, in which context they preferably modulate and especially preferably inhibit the interactions of $\beta_3$- or $\beta_5$-integrin receptors with ligands. The compounds are preferably particularly active in the case of the integrins $a_V\beta_3$, $a_V\beta_5$ and/or $a_{II}\beta_3$, and more preferably particularly active in the case of the integrins $a_V\beta_3$ and/or $a_V\beta_5$, but preferably also relative to $a_V\beta_1$-, $a_V\beta_6$- and/or $\alpha_V\beta_8$ receptors. These actions can be demonstrated, for example, according to the method described by J. W. Smith et al. in J. Biol. Chem. 265, 12267-12271 (1990).

[18] Thus, preferred for use in the methods according to the invention are compositions as described herein or as described in one or more of the paragraphs numbered [1] to [17] and/or the paragraphs relating thereto, wherein the oligopeptide comprises the Arg-Gly-Asp-subsequence.

Preferred for use in the methods according to the invention are compositions as described herein or as described in one or more of the paragraphs numbered [1] to [18] and/or the paragraphs relating thereto, wherein the oligopeptide is a cyclic oligopeptide.

[19] Preferred for use in the methods according to the invention are compositions as described herein or as described in one or more of the paragraphs numbered [1] to [18] and/or the paragraphs relating thereto, wherein the oligopeptide or cyclic oligopeptide is selected from the group consisting of cyclo-(Arg-Gly-Asp-DPhe-NMeVal), cyclo-(Arg-Gly-Asp-DPhe-Val), and the pharmaceutically acceptable derivatives, solvates and/or salts thereof.

[20] Preferred for use in the methods according to the invention are compositions as described herein or as described in one or more of the paragraphs numbered [1] to [19] and/or the paragraphs relating thereto, wherein the oligopeptide or cyclic oligopeptide is selected from the group consisting of cyclo-(Arg-Gly-Asp-DPhe-NMeVal) and the pharmaceutically acceptable derivatives, solvates and/or salts thereof having a solubility in water at 20° C. or at 25° C., preferably at 20° C., between 1 mg/mL and 15 mg/mL, more preferably between 2 mg/mL and 12 mg/mL, even more preferably between 3 mg/mL and 10 mg/mL and especially between 4 mg/mL and 9 mg/mL.

According to the invention, the at least one cyclopeptide is especially preferably selected from cyclo-(Arg-Gly-Asp-DPhe-NMeVal), and/or a salt or solvate thereof.

Especially preferred are solid materials comprising solid forms, more preferably solid amorphous and/or crystalline forms, of cyclo-(Arg-Gly-Asp-DPhe-NMeVal) and/or a salt or solvate thereof. Especially preferred are solid materials comprising solid forms, more preferably amorphous and/or crystalline solid forms, of cyclo-(Arg-Gly-Asp-DPhe-NMe-Val) and/or a salt or solvate thereof, which have a solubility in water at 20° C. between 1 mg/ml and 25 mg/ml. Preferably, the solubility in water at 20° C. is 20 mg/ml or lower, more preferably 18 mg/ml or lower, even more preferably 15 mg/ml or lower, even more preferably 12 mg/ml and especially 10 mg/ml or lower. Preferably, the solubility in water at 20° C. is 1 mg/ml or higher, more preferably 2 mg/ml or higher, even more preferably 3 mg/ml or higher, even more preferably 4 mg/ml or higher and especially 6 mg/ml or higher, but preferably not higher than the above given upper limits given for the solubility. Accordingly, the solubility in water at 20° C. is preferably in the range between 2 mg/ml and 15 mg/ml, even more preferably between 3 mg/ml and 12 mg/ml and especially between 4 mg/ml and 10 mg/ml, e.g. about 4 mg/ml, about 6 mg/ml, about 8 mg/ml, about 10 mg/ml or about 13 mg/ml.

Methods for determining the solubility of said cyclic oligopeptide(s) in water are known in the art. Preferably, the solubility in water at 20° C. or at 25° C., preferably at 20° C., is determined at an about neutral pH of the solution of said cyclic oligopeptide(s) in water. Even more preferably, the solubility in water at 20° C. or at 25° C., preferably at 20° C., is determined at a pH=7+/−0.5 of the solution of said cyclic oligopeptide(s) in water. Accordingly, the solubility is preferably determined in water at 20° C. or at 25° C., preferably at 20° C., at a pH in the range of 6.5 to 7.5, more preferably in the range of 6.5 to 7.0, such as at a pH value of about 6.8, about 7.0 or about 7.4.

The solubility of the inner (or internal) salt of the peptide of the formula cyclo-(Arg-Gly-Asp-DPhe-NMeVal) in water at 20° C. or at 25° C., preferably at 20° C., is preferably determined at the isoelectric point, which preferably corresponds to a pH value of about 6.8 and especially preferably corresponds to a pH value in the range of 6.7 to 6.9.

Preferred in this regard are amorphous solid forms and crystalline solid forms, more preferably crystalline solid forms, of cyclo-(Arg-Gly-Asp-DPhe-NMeVal) and/or the salts thereof, and preferably the solid materials containing them. Especially preferred in this regard amorphous solid forms and crystalline solid forms, more preferably crystalline solid forms of the inner salt of cyclo-(Arg-Gly-Asp-DPhe-NMeVal), and preferably the solid materials containing them or consisting of them.

Preferred in this regard are crystalline solid forms, more preferably crystalline solid forms of cyclo-(Arg-Gly-Asp-DPhe-NMeVal) and/or the salts thereof which are solvates or anhydrates, and preferably the solid materials containing them or consisting of them.

The salts and especially the inner salt of cyclo-(Arg-Gly-Asp-DPhe-NMeVal) can be present as a solvate or anhydrate. The solvates and anhydrates, more preferably the anhydrates, of the inner salt of cyclo-(Arg-Gly-Asp-DPhe-NMeVal) are especially preferred, especially the crystalline form of the anhydrate, and preferably the solid materials containing them or consisting of them.

Preferred solid materials comprising crystalline forms of cyclo-(Arg-Gly-Asp-DPhe-NMeVal) and especially comprising crystalline forms of the inner salt of cyclo-(Arg-Gly-Asp-DPhe-NMeVal) are described in detail below:

Cyclo-(Arg-Gly-Asp-DPhe-NMe-Val) or {[(2S,5R,8S,11S)-5-Benzyl-11-(3-guanidino-propyl)-8-isopropyl-7-methyl-3,6,9,12,15-pentaoxo-1,4,7,10,13-pentaaza-cyclopentadec-2-yl]-acetic acid} was first described in the patents/patent applications U.S. Pat. No. 6,001,961 and EP 0 770 622, which were first published in 1997. In said patents, various salt forms of said compound were described, e.g. the hydrochloride, the acetate and the methansulfonate. Later, an improved method of manufacture that led to the inner salt of cyclo-(Arg-Gly-Asp-DPhe-NMe-Val) was described in WO 00/53627. However, the solids obtained according to the described procedures appeared to be amorphous material.

Described hereinafter are novel solid materials that comprise cyclo-(Arg-Gly-Asp-DPhe-NMe-Val) in one or more crystalline form.

Preferred solid materials are described below:

A solid material of a compound according to formula Id,

cyclo-(Arg-Gly-Asp-DPhe-NMeVal)　　　　(Id)

wherein said solid material comprises one or more crystalline forms of the compound of formula Id, characterised by a unit cell with the lattice parameters a=9.5±0.5 Å,
b=23.0±5.0 Å, and
c=14.7±1.0 Å.

Said unit cell is preferably a crystallographic unit cell or a crystallographically determined unit cell.

In said unit cell, the angle α preferably is 90°±2°, the angle β preferably is 900±2° and/or the angle γ preferably is 900±2°.

Preferably, said solid material comprises at least 10% by weight, more preferably at least 30% by weight, even more preferably 60% by weight and especially at least 90% by weight or at least 95% by weight, of one or more crystalline forms of the compound of formula Id as defined above and/or below. For example, said solid material comprises about 25, about 50, about 75, about 95 or about 99% by weight of one or more crystalline forms of the compound of formula Id as defined above and/or below.

Especially preferably, the solid material comprises at least 10% by weight, more preferably at least 30 mole %, even more preferably 60 mole % and especially at least 90 mole % or at least 95 mole %, of one or more crystalline forms of the compound of formula Id as defined above and/or below. For example, the solid material comprises about 25, about 50, about 75, about 95 or about 99 mole % of one or more crystalline forms of the compound of formula Id as defined above and/or below.

The percentages by weight given for the solid material as described herein preferably relate to the ratio between the weight of the one or more crystalline forms as defined above/below contained in said solid material and the total amount by weight of the compound of formula Id contained in said solid material. In other words, the percentages by weight given preferably are the weight percentages of the sum of the one or more crystalline forms as defined above and/or below based on the total amount by weight of the compound of formula Id. Thus, the weight percentages given for the content of the one or more crystalline forms with in the solid material as described herein are preferably independent of the amount or content of compounds or impurities other than the compound according to formula Id contained in said solid material.

One or more crystalline forms in regard to said solid material preferably means that the solid material comprises at least one or more crystalline form or modification of the compound of formula Id having a unit cell within the lattice parameters as defined above and/or below, or that the solid material comprises mixtures of two or more, for example two or three, crystalline forms or modifications of the compound of formula Id, each having a unit cell within the lattice parameters as defined above and/or below.

Preferably, the solid material comprises one, two, three or four crystalline forms of the compound of formula Id as defined above and/or below.

More preferably, the solid material comprises one or more, preferably one, two, three or four, even more preferably one or two, crystalline forms of the compound of formula Id, each having a unit cell with lattice parameters (ULP) selected from a group consisting of
ULP1: a1=9.5±0.5 Å,
  b1=26.0±1.5 Å, and
  c1=14.3±0.7 Å,
and
ULP2: a2=9.8±0.5 Å,
  b2=20.0±1.5 Å, and
  c2=15.4±0.7 Å.

More preferably, the solid material comprises one or more, preferably one, two, three or four, even more preferably one or two, crystalline forms of the compound of formula Id, each having a unit cell with lattice parameters (ULP) selected from a group consisting of
ULP1: a1=9.5±0.3 Å,
  b1=26.0±1.0 Å, and
  c1=14.3±0.5 Å,
and
ULP2: a2=9.8±0.3 Å,
  b2=20.0±1.0 Å, and
  c2=15.4±0.5 Å.

In the unit cell with lattice parameters ULP1 and/or ULP2, the angle $\alpha$ preferably is 90°±2°, the angle $\beta$ preferably is 90°±2° and/or the angle $\gamma$ preferably is 90°±2°.

Preferably, the unit cell with lattice parameters ULP1 can be characterised, alternatively or additionally, preferably additionally, by a content of about 4 molecules of the compound of formula Id within said unit cell.

In the unit cell with lattice parameters ULP2, the angle $\alpha$ preferably is 90°±0.5°, the angle $\beta$ preferably is 90°±0.5° and/or the angle $\gamma$ preferably is 900±0.5°. In the unit cell with lattice parameters ULP2, the angles $\alpha$, $\beta$ and $\gamma$ more preferably are 90°±0.1.

Preferably, the unit cell with lattice parameters ULP2 can be characterised, alternatively or additionally, preferably additionally, by a content of about 4 molecules of the compound of formula Id within said unit cell.

More preferably, the solid material comprises one or more, preferably one, two, three or four, even more preferably one or two, crystalline forms of the compound of formula Id, selected from
crystalline form A1, characterised by a unit cell with the lattice parameters a=9.8±0.1 Å, b=19.5±0.5 Å, and c=15.4±0.1 Å,
crystalline form S1, characterised by a unit cell with the lattice parameters a=9.4±0.1 Å, b=25.9±0.5 Å, and c=14.1±0.1 Å,
crystalline form S2, characterised by a unit cell with the lattice parameters a=9.3±0.1 Å, b=26.6±0.5 Å, and c=14.7±0.1 Å, and
crystalline form S3, characterised by a unit cell with the lattice parameters a=9.6±0.1 Å, b=25.9±0.5 Å, and c=13.9±0.1 Å.

More preferably, the solid material comprises one or more, preferably one, two, three or four, even more preferably one or two, crystalline forms of the compound of formula Id, selected from
crystalline form A1, characterised by a unit cell with the lattice parameters a=9.8±0.1 Å, b=19.5±0.5 Å, and c=15.4±0.1 Å, preferably with a=$\beta$=$\gamma$=90°±1° and especially with $\alpha$=$\beta$=$\gamma$=90°;
crystalline form S1, characterised by a unit cell with the lattice parameters a=9.4±0.1 Å, b=25.9±0.5 Å, and c=14.1±0.1 Å, preferably with a=$\beta$=$\gamma$=90°2°, and especially with $\alpha$=90°±1°, $\beta$=91°1, $\gamma$=90°±1° and especially with $\alpha$=90°, $\beta$=91.2°, $\gamma$=90°;
crystalline form S2, characterised by a unit cell with the lattice parameters a=9.3±0.1 Å, b=26.6±0.5 Å, and c=14.7±0.1 Å, preferably with a=$\beta$=$\gamma$=90°±1° and especially with $\alpha$=$\beta$=$\gamma$=90°; and
crystalline form S3, characterised by a unit cell with the lattice parameters a=9.6±0.1 Å, b=25.9±0.5 Å, and c=13.9±0.1 Å, preferably with $\alpha$=$\beta$=$\gamma$=90°±1° and especially with $\alpha$=$\beta$=$\gamma$=90°.

The crystalline forms S1, S2 and S3 are preferably further characterised as solvates.

Preferably, the crystalline forms S1, S2 and S3 can be characterised, alternatively or additionally, preferably additionally, by a content of about 4 molecules of the compound of formula Id within said unit cells.

The crystalline forms A1, S2 and/or S3 are preferably further characterised by orthorhombic unit cell.

The crystalline form S1 is preferably further characterised by a monoclinic in unit cell.

The unit cell and the lattice parameters, preferably including, but not limited to a, b, c, $\alpha$, $\beta$ and/or $\gamma$, are crystallographic parameters known to the ones skilled in the art. Hence, they can be determined according to methods known in the art. The same preferably holds true for the orthorhombic and/or monoclinic form of the unit cell.

The above given unit cells and the lattice parameters relating thereto are preferably determined by X-Ray Diffraction, more preferably Single Crystal X-Ray Diffraction and/or Powder X-Ray Diffraction, according to standard methods, for example methods or techniques as described in the European Pharmacopeia 6$^{th}$ Edition chapter 2.9.33, and/or as described in Rolf Hilfiker, 'Polymorphism in the Pharmaceutical Industry', Wiley-VCH. Weinheim 2006 (Chapter 6: X-Ray Diffraction), and/or H. G. Brittain, 'Polymorphism in Pharmaceutical Solids, Vol. 95, Marcel Dekker Inc., New York 1999 (Chapter 6 and references therein).

Alternatively preferably, the above given unit cells and the lattice parameters relating thereto can be obtained by single crystal X-Ray, optionally together with additional structure data, preferably conducted on a XCalibur diffractometer from Oxford Diffraction equipped with graphite monochromator and CCD Detector using Mo K$_\alpha$ radiation, preferably at a temperature of 298 K±5 K; and/or
on a CAD4 four circle diffractometer from Nonius equipped with graphite monochromator and scintillation counter using Mo K$_\alpha$ radiation, preferably at a temperature of 298 K±5 K.

The above given unit cells and the lattice parameters relating thereto are preferably determined by X-Ray Diffraction, more preferably Powder X-Ray Diffraction, according to standard methods, for example methods or techniques as described in the European Pharmacopeia 6$^{th}$ Edition chapter 2.9.33, and/or as described in Rolf Hilfiker, 'Polymorphism in the Pharmaceutical Industry', Wiley-VCH. Weinheim 2006 (Chapter 6: X-Ray Diffraction), and/or H. G. Brittain, 'Polymorphism in Pharmaceutical Solids, Vol. 95, Marcel Dekker Inc., New York 1999 (Chapter 6 and references therein).

Higher contents of the one or more crystalline forms as defined above and/or below in the solid material as described above and/or below are generally preferred.

Preferred solid materials for use in the compositions according to the invention are described in PCT/EP2010/003100, titled "Novel solid materials of {[(2S,5R,8S,11S)-5-Benzyl-11-(3-guanidino-propyl)-8-isopropyl-7-methyl-3,6,9,12,15-pentaoxo-1,4,7,10,13-pentaaza-cyclopentadec-2-yl]-acetic acid} and methods for obtaining them", of the same applicant, the disclosure of which is incorporated into this application by reference in its entirety.

A solid material as described above and/or below, essentially consisting of one or more crystalline forms of the compound of formula Id, characterised by a unit cell with the lattice parameters
a=9.5±0.5 Å,
b=23.0±5.0 Å, and
c=14.7±1.0 Å,
and especially characterised as described above and/or below. Essentially consisting of one or more crystalline forms of the compound of formula Id preferably means that the compound of formula Id contained in said solid material is essentially selected from said one or more crystalline forms of the compound of formula Id, or in other words, that the one or more crystalline forms in said solid form provide for the essential amount of compound of formula Id in said solid form. More specifically, essentially in this regard preferably means that the one or more crystalline forms in said solid form provide for 90% or more, preferably 95% or more, even more preferably 99% or more and especially 99.9% or more, of the amount of compound of formula Id in said solid form. In this regard, the given percentages (%) are preferably selected from mole % and % by weight and especially preferably are mole %.

Said amounts can be provided by one single crystalline form as described herein, or by mixtures of two or more crystalline form as described herein. Preferably, said amounts are provided by one single crystalline form as described herein. More preferably, said amounts are provided by one single crystalline form, selected from crystalline form A1, crystalline form S1, crystalline form S2 and crystalline form S3 as described herein.

The crystalline form A1, crystalline form S1, crystalline form S2 and crystalline form S3 is further described in PCT/EP2010/003100 of the same applicant, the disclosure of which is incorporated into this application by reference in its entirety.

If the solid material comprises two or more of the crystalline forms as described herein, one of these crystalline forms is preferably the major crystalline form and the one or more further crystalline forms present are present in minor amounts. The major crystalline form preferably provides for 60% by weight or more, more preferably 75% or more, even more preferably 90% or more and especially 95 or 99% or more, of the total amount of the crystalline forms present. In this regard, the given percentages (%) are preferably selected from mole % and % by weight and especially preferably are mole %.

If not specified otherwise, percentages (or %) given herein for compounds and/or solvents are preferably either percentages by weight or mole percent, preferably mole percent. Since the content of the one or more crystalline forms in the solid material as described herein, and, if applicable, the ratio of two or more crystalline forms in the solid material as described herein, can advantageously be determined via methods including, but not limited to, Powder X-Ray-Diffraction, Raman-spectroscopy and infrared spectroscopy, and more preferably are determined by Powder X-Ray-Diffraction, Raman-spectroscopy and/or infrared spectroscopy, percent values related thereto are especially preferably mole percent values, if not explicitly stated otherwise.

Preferably, if not specified otherwise, percentages (or %) given herein
i) for spectral data, such as transmission, especially IR transmission, Raman intensity;
ii) Powder X-Ray diffraction intensities (PXRD intensitiel); and/or
iii) or analytical parameters, such as relative humidity (rh or r.h.), and the like,
are preferably relative percentages (i.e. percent of the respective maximum value).

A preferred subject of the invention are the one or more crystalline forms of the compound of formula Id as described herein and especially as described above and/or below.

Preferably, the one or more crystalline forms of the compound of formula Id are selected from the crystalline forms as described above and/or below having a monoclinic unit cell or a orthorhombic unit cell.

Preferably, the one or more crystalline forms of the compound of formula Id are selected from anhydrates and solvates.

Preferably, the anhydrates as described herein and especially the crystalline form A1 can be characterised, alternatively or additionally, by a melting/decomposition temperature of >282° C., more preferably 288±5° C. or higher, and especially 288±5° C.

The melting/decomposition temperatures and/or thermal behaviors described herein are preferably determined by DSC (Differential Scanning Calorimetry) and TGA ((ThermoGravimetric Analysis). DSC and/or TGA methods or generally thermoanalytic methods and suitable devices for determining them are known in the art, for examples from European Pharmacopeia 6$^{th}$ Edition chapter 2.02.34, wherein suitable standard techniques are described. More preferably, for the melting/decomposition temperatures or behaviors and/or the thermoanalysis in generally, a Mettler Toledo DSC 821 and/or Mettler Toledo TGA 851 are used, preferably as described in the European Pharmacopeia 6$^{th}$ Edition chapter 2.02.34.

Figure 2:
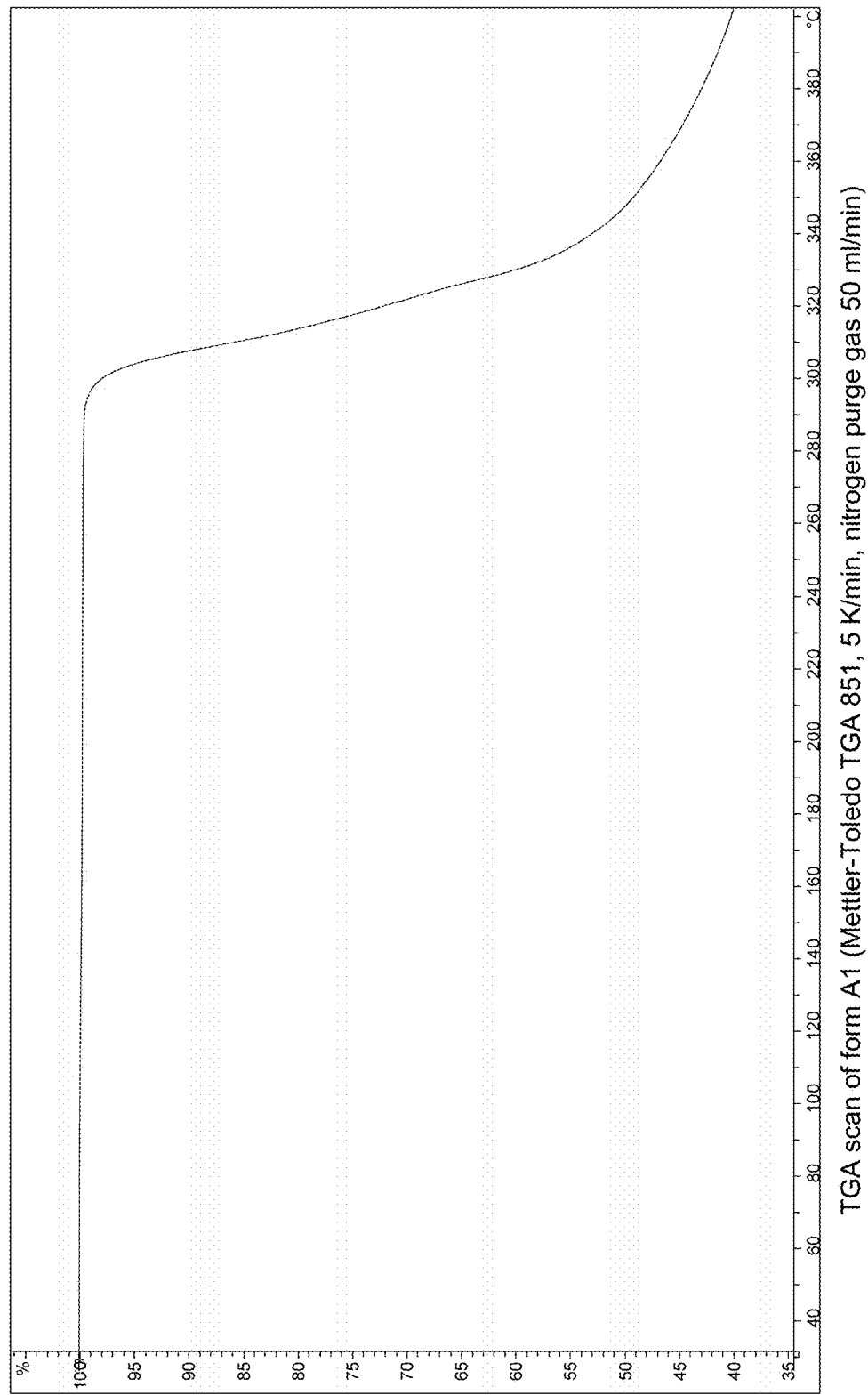
FIG. 2 shows the scan of form A1 (Mettler-Toledo TGA 851, 5 K/min, nitrogen purge gas 50 ml/min).

The DSC and TGA measurements showing the thermal analysis (Mettler-Toledo DSC 821, 5 K/min, nitrogen purge gas 50 ml/min; Mettler-Toledo TGA 851, 5 K/min, nitrogen purge gas 50 ml/min) and the melting/decomposition temperature given above is shown in FIG. 1 and FIG. 2.

Preferably, the anhydrates as described herein and especially the crystalline form A1 can be characterised, alternatively or additionally, by Powder X-Ray Diffraction and more preferably by the Powder X-Ray Diffraction pattern comprising one or more of the Powder X-ray peaks given below, more preferably comprising 6 or more of the Powder X-ray peaks given below, even more preferably 8 or more of the Powder X-ray peaks given below, and especially comprising all of the of the Powder X-ray peaks given below:

a)

| No. | D ± 0.1 [Å] | °2 θ (Cu-Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably b)

| No. | D ± 0.1 [Å] | °2 θ (Cu-Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

Preferably, the anhydrates as described herein and especially the crystalline form A1 can be characterised, alternatively or additionally, by Powder X-Ray Diffraction and more preferably by the Powder X-Ray Diffraction pattern comprising the Powder X-ray peaks given below:

a)

| No. | D [Å] | °2 θ (Cu-Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably b)

| No. | D [Å] | °2 θ (Cu-Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 4 | 8.24 | 10.7 | 1 | 1 | 0 |
| 7 | 6.91 | 12.8 | 1 | 0 | 2 |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

Preferably, the anhydrates as described herein and especially the crystalline form A1 can be characterised, alternatively or additionally, by Powder X-Ray Diffraction and more preferably by the Powder X-Ray Diffraction pattern comprising one or more of the Powder X-ray peaks given below, more preferably comprising 10 or more of the Powder X-ray peaks given below, even more preferably 12 or more of the Powder X-ray peaks given below, and especially comprising all of the of the Powder X-ray peaks given below:

a)

| No. | D ± 0.1 [Å] | °2 θ (Cu-Kα$_1$ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 3 | 8.75 | 10.1 | 1 | 0 | 1 |
| 4 | 8.24 | 10.7 | 1 | 1 | 0 |
| 5 | 7.69 | 11.5 | 0 | 2 | 0 |
| 6 | 7.16 | 12.4 | 0 | 2 | 1 |
| 7 | 6.91 | 12.8 | 1 | 0 | 2 |
| 8 | 6.05 | 14.6 | 1 | 2 | 0 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.2 | 2 | 0 | 2 |

-continued

| No. | D ± 0.1 [Å] | °2 θ (Cu-Kα₁ radiation) ± 0.1° | Miller indizes h | k | l |
|---|---|---|---|---|---|
| 13 | 4.21 | 21.1 | 2 | 1 | 2 |
| 14 | 4.12 | 21.2 | 2 | 2 | 0 |
| 15 | 3.79 | 23.4 | 2 | 1 | 3 | or more preferably
b)

| No. | D ± 0.1 [Å] | °2 θ (Cu-Kα₁ radiation) ± 0.1° | Miller indizes h | k | l |
|---|---|---|---|---|---|
| 1 | 12.08 | 7.3 | 0 | 1 | 1 |
| 2 | 9.75 | 9.1 | 0 | 0 | 2 |
| 3 | 8.75 | 10.1 | 1 | 0 | 1 |
| 4 | 8.24 | 10.7 | 1 | 1 | 0 |
| 5 | 7.69 | 11.5 | 0 | 2 | 0 |
| 6 | 7.16 | 12.4 | 0 | 2 | 1 |
| 7 | 6.91 | 12.8 | 1 | 0 | 2 |
| 8 | 6.05 | 14.7 | 0 | 2 | 2 |
| 9 | 4.88 | 18.2 | 0 | 0 | 4 |
| 10 | 4.54 | 19.5 | 2 | 1 | 1 |
| 11 | 4.43 | 20.0 | 1 | 3 | 1 |
| 12 | 4.37 | 20.3 | 2 | 0 | 2 |
| 13 | 4.21 | 21.1 | 2 | 1 | 2 |
| 14 | 4.12 | 21.5 | 2 | 2 | 0 |
| 15 | 3.79 | 23.4 | 2 | 1 | 3 |

The Powder X-Ray Diffraction and more preferably the Powder X-Ray Diffraction pattern is preferably performed or determined as described herein and especially performed or determined by standard techniques as described in the European Pharmacopeia 6$^{th}$ Edition chapter 2.9.33, and is even more preferably obtained with the parameters Cu-Kα₁ radiation and/or λ=1.5406 Å, preferably on a Stoe StadiP 611 KL diffractometer.

Figure 3:
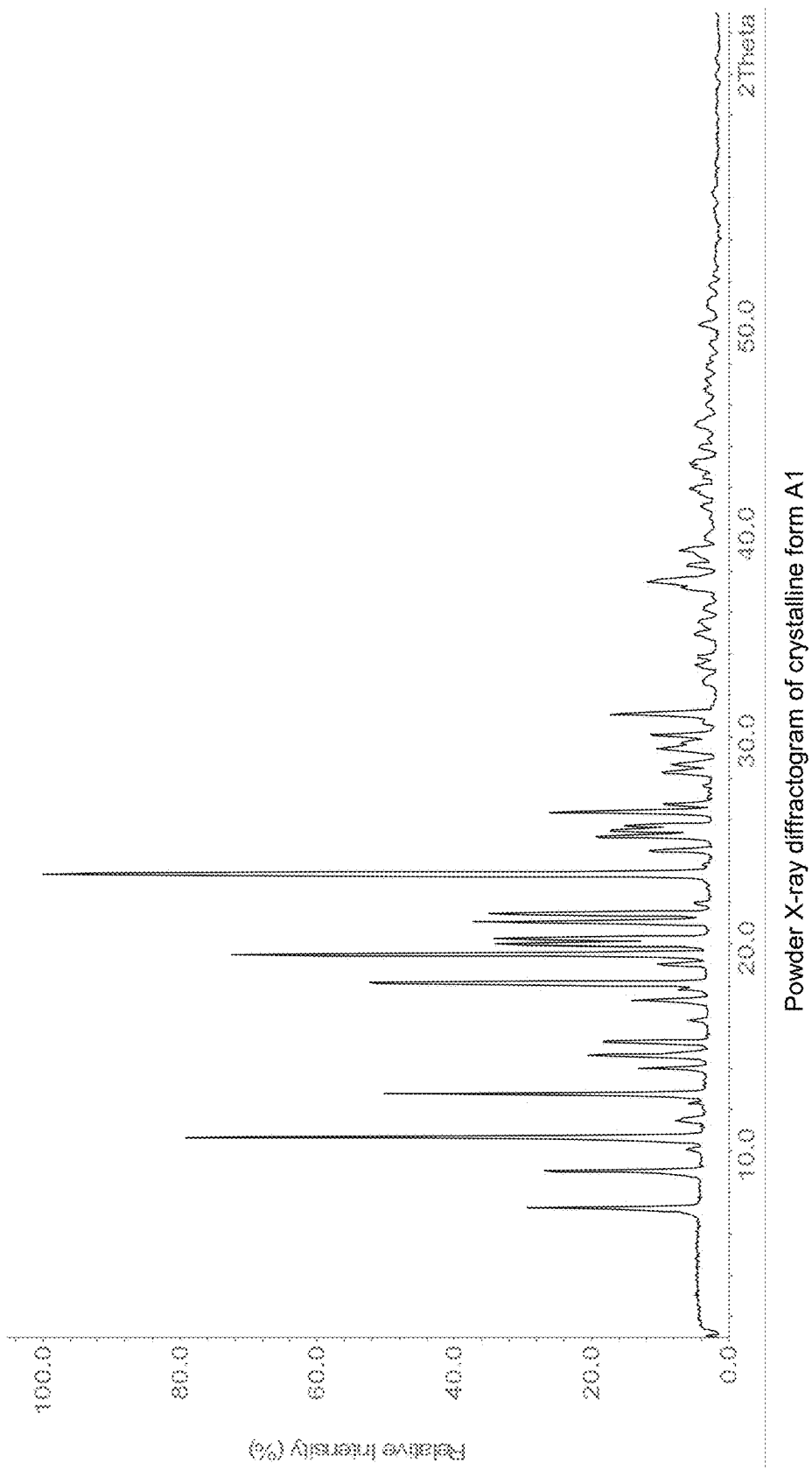
FIG. 3 shows the Powder X-ray diffractogram of crystalline form A1.

FIG. 3 shows the Powder X-ray diffractogram of crystalline form A1

Preferably, the anhydrates as described herein and especially the crystalline form A1 can be characterised, alternatively or additionally, by Single Crystal X-Ray Structure Data, for example Single Crystal X-Ray Structure Data obtained on a diffractometer preferably equipped with a graphite monochromator and CCD Detector, preferably using Mo K$_α$ radiation, preferably at a temperature of 298 K±5 K, and even more preferably on a XCalibur diffractometer from Oxford Diffraction equipped with graphite monochromator and CCD Detector using Mo K$_α$ radiation at about 298 K.

According to the Single Crystal X-Ray Structure Data obtained, the anhydrate of the compound of formula Id and especially crystalline form A1 crystallises in the orthorhombic space group P 2₁ 2₁ 2₁ with the lattice parameters a=9.8 Å, b=15.4 Å, c=19.5 Å (±0.1 Å) and the unit cell volume is preferably 2940 (±10) Å$^3$ From the single crystal structure it is obvious that form A1 represents an anhydrate or ansolvate.

Figure 4:
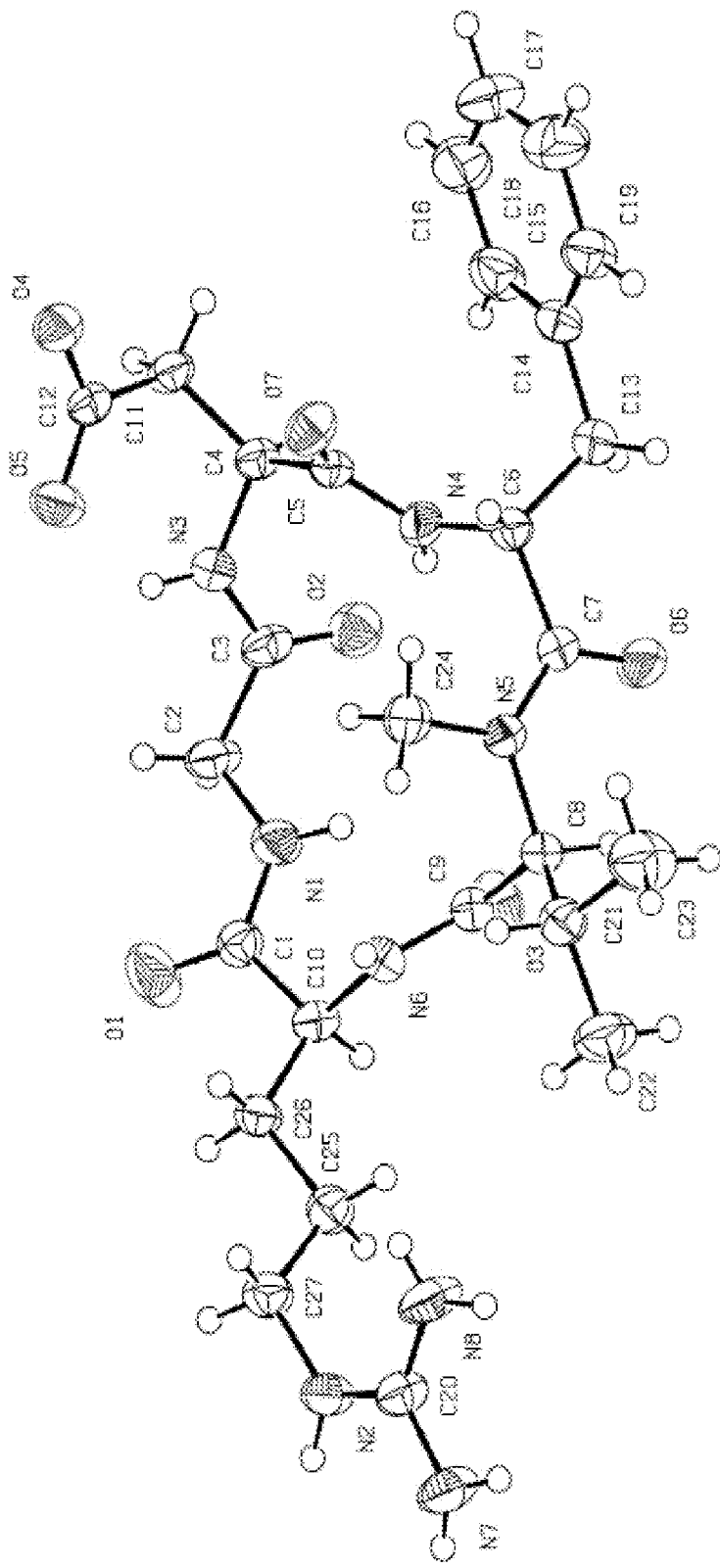
FIG. 4 shows the single crystal structure of form A1.

The Single Crystal X-Ray Structure is depicted in FIG. 4.

Preferably, the anhydrates as described herein and especially the crystalline form A1 can be characterised, alternatively or additionally, by the infrared-spectroscopy data comprising one or more of the
band positions (±2 cm$^{-1}$) given below, more preferably comprising 6 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:

3431 cm$^{-1}$(s), 3339 cm$^{-1}$(s), 3189 cm$^{-1}$(s), 2962 cm$^{-1}$(m), 2872 cm$^{-1}$(m), 1676 cm$^{-1}$(s), 1660 cm$^{-1}$(s), 1617 cm$^{-1}$(s), 1407 cm$^{-1}$(s), 1316 cm$^{-1}$(m), 1224 cm$^{-1}$(m), 1186 cm$^{-1}$(m), 711 cm$^{-1}$(m).

More preferably, the anhydrates as described herein and especially the crystalline form A1 can be characterised, alternatively or additionally, by the infrared-spectroscopy data comprising one or more of the
band positions (±2 cm$^{-1}$) given below, more preferably comprising 9 or more of the band positions (±2 cm$^{-1}$) given below, even more preferably comprising 12 or more of the band positions (±2 cm$^{-1}$) given below, and especially comprising all the band positions (±2 cm$^{-1}$) given below, preferably together with the relative intensities given in brackets:

3431 cm$^{-1}$(s), 3339 cm$^{-1}$(s), 3189 cm$^{-1}$(s), 3031 cm$^{-1}$(m), 2962 cm$^{-1}$(m), 2872 cm$^{-1}$(m), 1676 cm$^{-1}$(s), 1660 cm$^{-1}$(s), 1617 cm$^{-1}$(s), 1539 cm$^{-1}$(s), 1493 cm$^{-1}$(s), 1407 cm$^{-1}$(s), 1358 cm$^{-1}$(m), 1316 cm$^{-1}$(m), 1247 cm$^{-1}$(m), 1224 cm$^{-1}$(m), 1186 cm$^{-1}$(m), 994 cm$^{-1}$(w), 921 cm$^{-1}$(w), 711 cm$^{-1}$(m), 599 cm$^{-1}$(m).

The relative intensities given in brackets are preferably defined as follows: *"s"=strong (transmittance preferably ≤50%), "m"=medium (preferably 50% <transmittance ≤70%), "w"=weak (transmittance preferably >70%)

The IR or FT-IR spectrum is preferably obtained using a KBr pellet as sample preparation technique.

The IR-spectroscopy data is preferably obtained by FT-IR-spectroscopy, The IR-spectroscopy data or FT-IR-spectroscopy data is preferably obtained by standard techniques as described in the European Pharmacopeia 6$^{th}$ Edition chapter 2.02.24. For the measurement of the FT-IR-spectra, preferably a Bruker Vector 22 spectrometer is used. FT-IR spectra are preferably base-line corrected, preferably using Bruker OPUS software.

Figure 5:
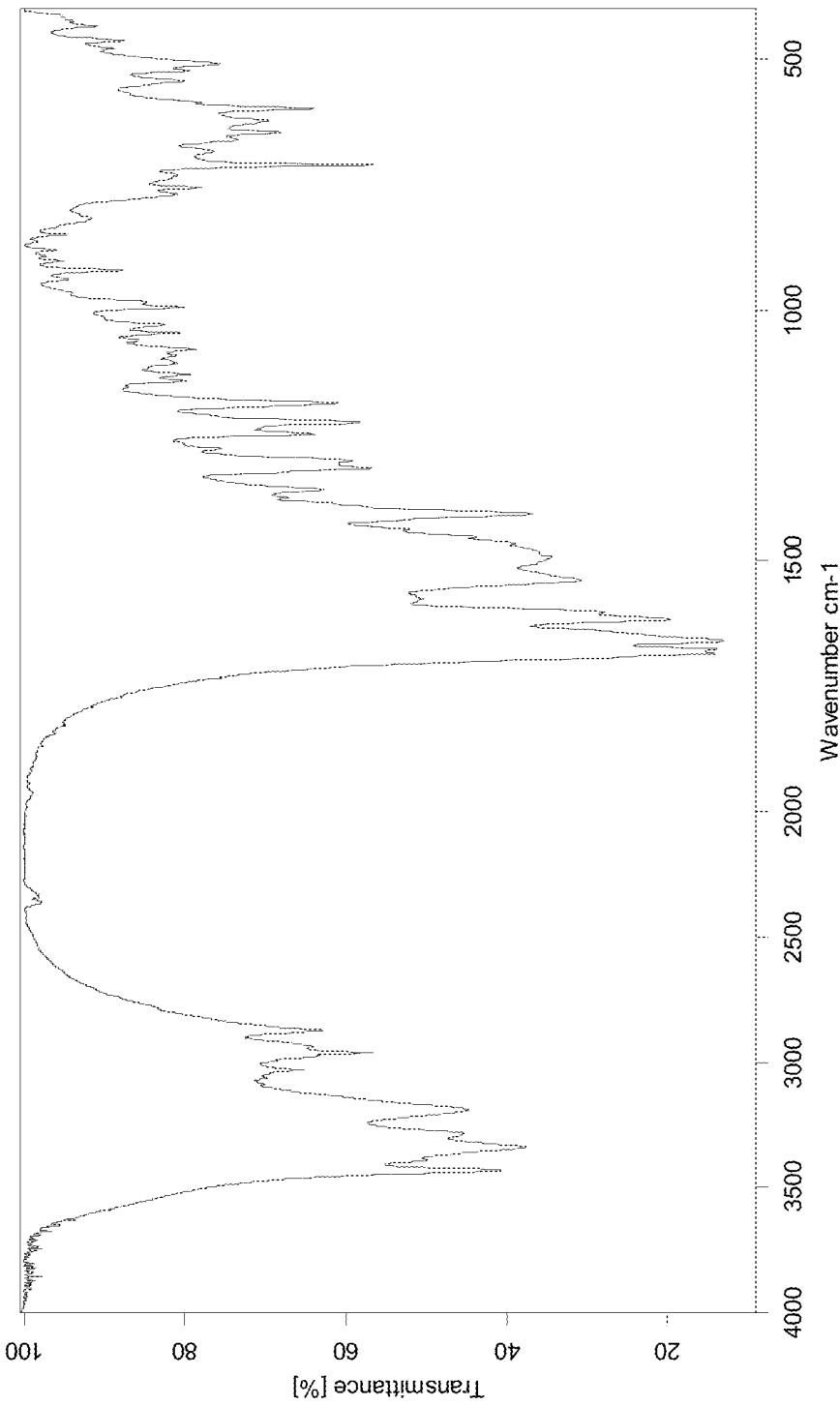
FIG. 5 shows the FTIR spectrum of form A1.

The FT-IR spectra of the anhydrates as described herein and especially the crystalline form A1 is given in FIG. 5.

Preferably, the anhydrates as described herein and especially the crystalline form A1 can be characterised, alternatively or additionally, by the Raman-spectroscopy data comprising one or more of the
band positions (±2 cm$^{-1}$) given below, more preferably comprising 9 or more of the band positions (±2 cm$^{-1}$) given below, even more preferably comprising 9 or more of the band positions (±2 cm$^{-1}$) given below, and especially comprising all the band positions (±2 cm$^{-1}$) given below, preferably together with the relative intensities given in brackets:

3064 cm$^{-1}$(w), 2976 cm$^{-1}$(m), 2934 cm$^{-1}$(m), 2912 cm$^{-1}$(m), 2881 cm$^{-1}$(m), 1603 cm$^{-1}$(w), 1209 cm$^{-1}$(w), 1029 cm$^{-1}$(w), 1003 cm$^{-1}$(m), 852 cm$^{-1}$(w).

More preferably, the anhydrates as described herein and especially the crystalline form A1 can be characterised, alternatively or additionally, by the Raman-spectroscopy data comprising one or more of the
band positions (±2 cm$^{-1}$) given below, more preferably comprising 12 or more of the band positions (±2 cm$^{-1}$) given below, even more preferably comprising 18 or more of the band positions (±2 cm$^{-1}$) given below, and especially comprising all the band positions (±2 cm$^{-1}$) given below, preferably together with the relative intensities given in brackets:
3064 cm$^{-1}$(w), 2976 cm$^{-1}$(m), 2934 cm$^{-1}$(m), 2912 cm$^{-1}$(m), 2881 cm$^{-1}$(m), 1677 cm$^{-1}$(w), 1648 cm$^{-1}$(w), 1603 cm$^{-1}$(w), 1584 cm$^{-1}$(w), 1465 cm$^{-1}$(w), 1407 cm$^{-1}$(w), 1314 cm$^{-1}$(w), 1242 cm$^{-1}$(w), 1209 cm$^{-1}$(w), 1129 cm$^{-1}$(w), 1029 cm$^{-1}$(w), 1003 cm$^{-1}$(m), 943 cm$^{-1}$(w), 901 cm$^{-1}$(w), 852 cm$^{-1}$(w), 623 cm$^{-1}$(w), 589 cm$^{-1}$(w).

The relative intensities given in brackets are preferably defined as follows: "s"=strong (relative Raman intensity preferably ≥0.04), "m"=medium (preferably 0.04 >relative Raman intensity ≥0.02), "w"=weak (relative Raman intensity preferably <0.02)

The Raman or FT-Raman spectrum is preferably obtained using Aluminium-cups as sample holders for the respective solid material.

The Raman-spectroscopy data is preferably obtained by FT-Raman-spectroscopy, The Raman-spectroscopy data or FT-Raman-spectroscopy data is preferably obtained by standard techniques as described in the European Pharmacopeia 6$^{th}$ Edition chapter 2.02.48. For the measurement of the FT-Raman-spectra, preferably a Bruker RFS 100 spectrometer is used. FT-Raman spectra are preferably base-line corrected, preferably using Bruker OPUS software.

Figure 6:
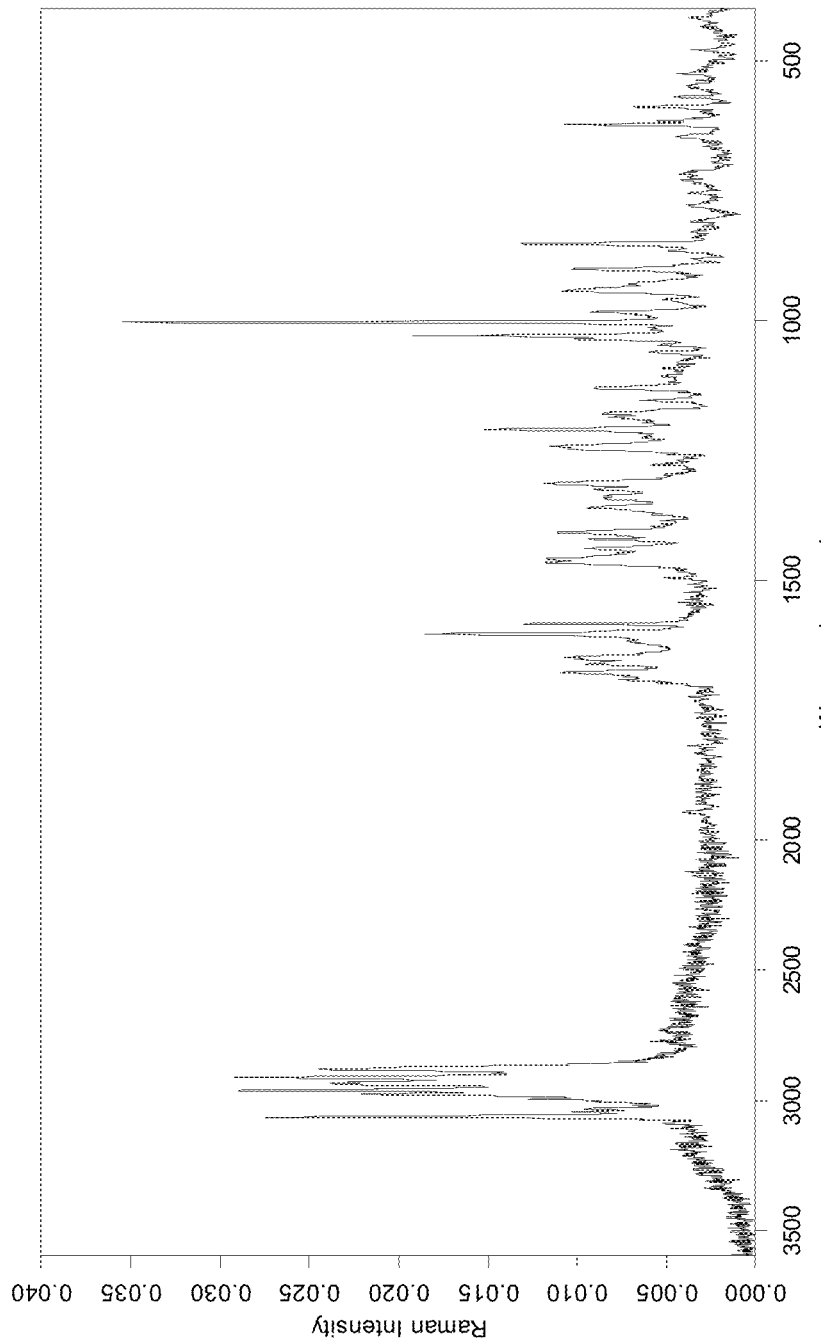
FIG. 6 shows the FT Raman spectrum of form A1.

The FT-Raman spectra of the anhydrates as described herein and especially the crystalline form A1 is given in FIG. 6.

Preferably, the anhydrates as described herein and especially the crystalline form A1 can be characterised, alternatively or additionally, by a solubility in water at 20° C. or 25° C., preferably at 20° C., in the range between 5 and 9 mg/mL, preferably in the range between 6 and 8 mg/mL and especially by a solubility in water at 20° C. or 25° C., preferably at 20° C., of about 7 mg/mL.

Figure 7:
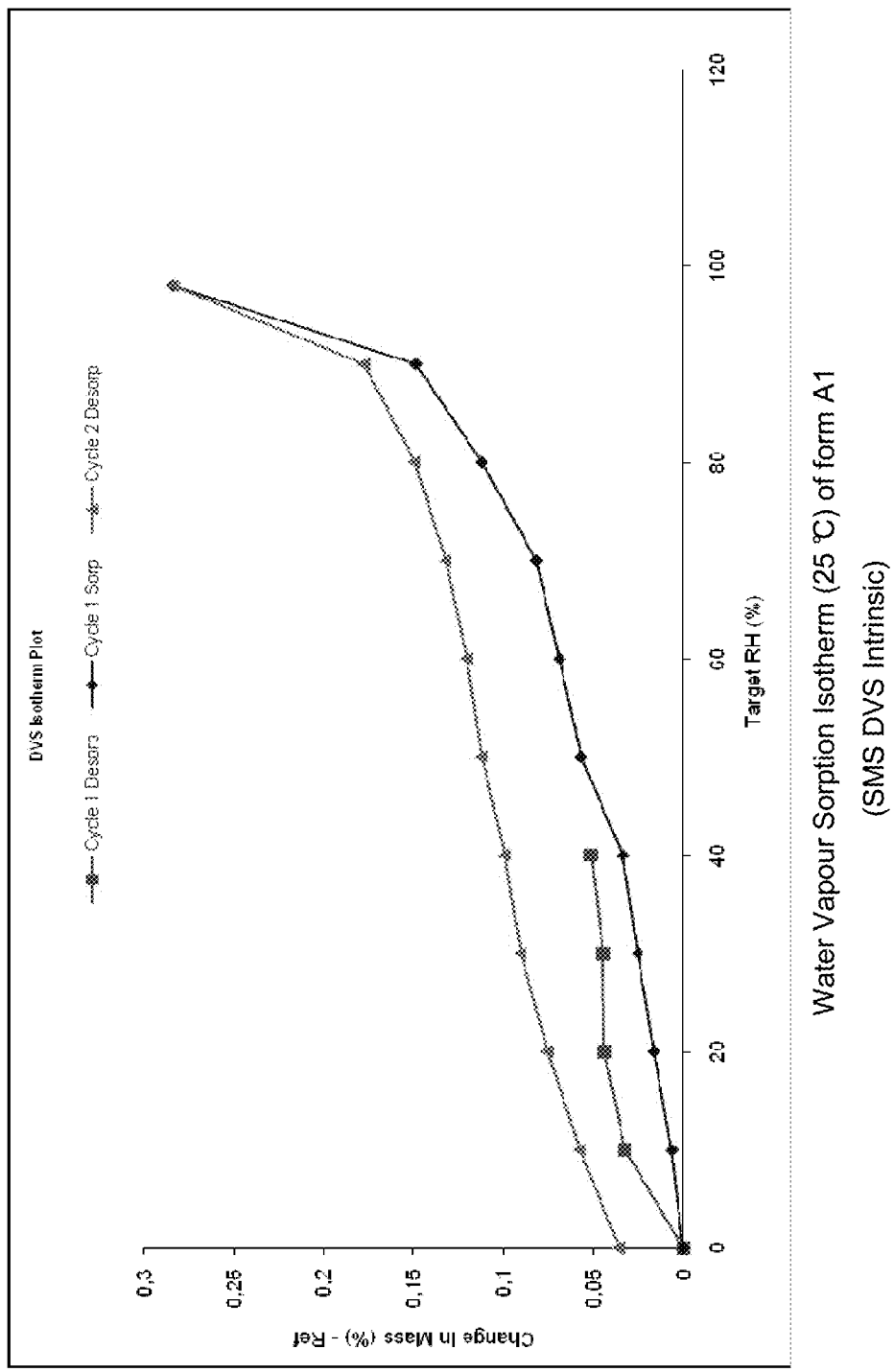
FIG. 7 shows the Water Vapour Sorption Isotherm (25° C.) of form A1 (SMS DVS Intrinsic).

Preferably, the anhydrates as described herein and especially the crystalline form A1 can be characterised, alternatively or additionally, by dynamic vapour experiments. The results can be obtained by standard techniques as described in Rolf Hilfiker, 'Polymorphism in the Pharmaceutical Industry', Wiley-VCH. Weinheim 2006 (Chapter 9: Water Vapour Sorption, and references therein). The Water Vapour Sorption behaviour shows small water uptake levels up to 98% relative humidity (rh or r.h.), and the anhydrates as described herein and especially the crystalline form A1 can be classified as non-hygroscopic acc. to Ph. Eur. criteria. No formation or conversion to a hydrate is observed. Water Vapor Sorption isotherm (25° C.) of crystalline form A1 (SMS DVS Intrinsic) is given in FIG. 7.

The crystalline form A1 preferably can be characterised as an anhydrate or ansolvate.

In this regard, anhydrate or ansolvate preferably means that the unit cell is free or essentially free of about stoichiometric amounts of solvent molecules of one or more solvents. In this regard, anhydrate or ansolvate more preferably means that the unit cell is essentially free of water and solvent molecules. Essentially free of solvent molecules in this regard preferably means that the amount of solvent molecules in the unit cell is lower than 0.5, more preferably lower than 0.1, even more preferably lower than 0.01 and especially lower than 0.001.

Since both ansolvates and an anhydrates are characterised by the absence of the respective solvents and thus characterised by the absence of any solvent, the terms anhydrate and ansolvate are preferably to be regarded as synonyms in the context of the present invention.

The amount of molecules in the unit cell is preferably determined by crystallographic methods, more preferably by single crystal X-ray diffraction and/or powder X-ray diffraction.

Alternatively, the amount of solvent in said crystalline forms, said solvates and/or in the respective unit cell can be determined or estimated by elemental analysis, gas chromatography or Karl-Fischer titration. In this context, essentially free of solvent molecules preferably means a solvent content of less than 5%, even more preferably less than 2%, even more preferably less than 1% and especially less than 0.1%, for example 5% to 0.1% or 2% to 0.01%. In this regard, the given percentages (%) are preferably selected from mole % and % by weight and especially preferably are % by weight.

The anhydrates as described herein and especially the crystalline form A1 shows one or more properties selected from the advantageous properties discussed above. More specifically, the anhydrates as described herein and especially the crystalline form A1 can shown to be the thermodynamically stable ansolvated form and/or thermodynamic stable form and surprisingly the thermodynamically stable form in the presence of aqueous based solvents, preferably including, but not limited to, suspensions and wetted material, and especially in essentially aqueous systems, such as water saline and the like, such as, but not limited to, suspensions and wetted material, and especially in such aqueous systems in the absence of methanol and/or ethanol. Wetted material in this regard is preferably a mixture of the respective anhydrate with at least 5% by weight, more preferably at least 10% by weight and especially 20% by weight, of the respective aqueous system. Furthermore, the anhydrates as described herein and especially the crystalline form A1 shows superior properties in terms of hygroscopicity behaviour, with physical stability of the crystal form throughout the entire relative humidity range (0-98%) and/or the crystallinity and thermal behaviour are excellent.

This results in excellent properties for processing (e.g. phase separation by filtration, drying, milling, micronisation) and storage, thus being i.a. superior for the formulation of suspensions. The anhydrates as described herein and especially the crystalline form A1 exhibit superior properties for the purification of the compound of formula Id, since a reduction of structurally related impurities, ionic compounds and residual solvent can be easily achieved. Thus, purification can be achieved in one step, where the solid forms, e.g. amorphous forms according to the conventional, prior known processes, and/or other, non-anhydrate polymorphic crystalline forms require significantly higher effort for a purity in line with GMP standards, e.g. three or more subsequent purification procedures.

The compound of formula Id also forms a class of pseudopolymorphs which incorporate different solvents in variable amounts and/or ratios, preferably ratios, and thus are solvates. These solvates are structurally closely related as shown, e.g. by Powder X-Ray Diffraction data, including Indexing of these forms, which leads to similar unit cells. Also, selected examples for the structures will be discussed based on single-crystal structure and structure solutions based on powder data. Finally a discussion on the specific beneficial properties of this pseudopolymorphic class will be given.

Said class of pseudopolymorphs is fully described in detail in WO 2010/133367, the disclosure of which is incorporated by reference into this application in its entirety.

The combination of reduced hygroscopicity, good solubility and good crystallinity leads to superior properties compared to the amorphous phase. In comparison, the purification, the handling and the processing of the amorphous material is very difficult, due to, e.g. the very high hygroscopicity and the low stability of the amorphous solid material.

Further, the pseudopolymorphic forms and/or the anhydrates according the invention show improved physical and/or chemical stability compared to the amorphous phase, preferably leading to a reduced formation of degradation products during storage, for example by hydrolysis. This improved hydrolytic stability of the solid material as described herein and especially of the crystalline forms as described herein is believed to be caused by the reduction of trace amounts of ionic impurities that are normally present in the amorphous material of prior art.

As a result, all those factors discussed herein are believed to account for the advantageously improved solid state stability of the solid material as described herein, the crystalline forms as described herein and especially of the solvates and/or anhydrates as described herein.

The solid material as described herein and especially the one or more crystalline forms as described herein can be prepared by contacting the compound according to formula Id with a solvent or solvent mixture, preferably a polar and/or protic solvent or solvent mixture.

Especially preferred processes for the manufacture, processes for the transformation or conversion and additionally preferred temperatures, solvents, solvent mixtures, reaction times, starting materials and/or additional process parameters are given in the examples. Thus, the examples provide sufficient guidance, together with the description of the instant invention and/or the claims, to carry out the invention in its full breadth. However, processes and especially process parameters can be taken out of the examples, as well individually as in combinations of one or more of those processes and/or parameters, and used together with the disclosure in the description and/or claims.

Thus, preferred is a composition as described herein, wherein the oligopeptide or cyclic oligopeptide comprises or is solid cyclo-(Arg-Gly-Asp-DPhe-NMeVal) in a polymorphic form having crystallographic unit cell with the lattice parameters
a=9.8±0.5 Å, b=19.5±1.0 Å, and c=15.4±0.5 Å.

[21] Thus, preferred is a composition as described herein or as described in one or more of the paragraphs numbered [1] to [20] and/or the paragraphs relating thereto for use in the methods according to the invention, wherein the oligopeptide or cyclic oligopeptide comprises or is solid cyclo-(Arg-Gly-Asp-DPhe-NMeVal) in a polymorphic form having crystallographic unit cell with the lattice parameters
a=9.8±0.1 Å, b=19.5±0.5 Å, and c=15.4±0.1 Å.

Preferably, said composition comprises 5% or more, preferably 10% or more, more preferably 20% or more, even more preferably 40%, even more preferably 60% or more, even more preferably 80% or more and especially 90% or more of the contained solid cyclo-(Arg-Gly-Asp-DPhe-NMeVal) in a polymorphic form having crystallographic unit cell with the lattice parameters a=9.8±0.5 Å, b=19.5±1.0 Å, and c=15.4±0.5 Å.

Preferably, said composition comprises 5% or more, preferably 10% or more, more preferably 20% or more, even more preferably 40%, even more preferably 60% or more, even more preferably 80% or more and especially 90% or more of the contained solid cyclo-(Arg-Gly-Asp-DPhe-NMeVal) in a polymorphic form having crystallographic unit cell with the lattice parameters a=9.8±0.1 Å, b=19.5±0.5 Å, and c=15.4±0.1 Å.

Said solid cyclo-(Arg-Gly-Asp-DPhe-NMeVal) in a polymorphic form having a crystallographic unit cell with the lattice parameters as described in one or more of the four paragraphs above is preferably also referred to as A1, form A1, solid form A1, crystalline form A1 and/or polymorphic form A1.

[22] Preferred are compositions as described herein or as described in one or more of the paragraphs numbered [1] to [21] and/or the paragraphs relating thereto for use in the methods according to the invention, comprising
a) 20 to 40% of cyclo-(Arg-Gly-Asp-DPhe-Val) or cyclo-(Arg-Gly-Asp-DPhe-NMeVal), the pharmaceutically acceptable derivatives, solvates and/or salts thereof,
b) 0.01 to 10% of one or more amphiphilic compounds as described herein and especially as described in one or more of the paragraphs numbered [1] to [14] and preferably also as described in the paragraphs relating thereto,
c) water, and optionally
d1) 0 to 20% of one or more pharmaceutically active ingredients other than the compound according to a), and/or.
d2) 0 to 20 of one or more pharmaceutically acceptable excipients other than the compounds according to b) and c),
with the proviso that the sum of a), b), c), d1) and d2) makes up to 99%, 99.9% or 100% of the composition.

[23] More preferred for use in the methods according to the invention are compositions as described herein, comprising
a) 20 to 40% of cyclo-(Arg-Gly-Asp-DPhe-Val) or cyclo-(Arg-Gly-Asp-DPhe-NMeVal), the pharmaceutically acceptable derivatives, solvates and/or salts thereof,
b) 0.01 to 10% of one or more amphiphilic compounds, selected from dioleoylphosphatidylglycerol, distearoylphosphatidylglycerol, dipalmitoylglycerophosphoglycerol and mixtures thereof, and the alkali salts thereof,
c) water, and optionally
d1) 0 to 20%, preferably 0 to 10% and especially 0.01 to 5%, of one or more pharmaceutically active ingredients other than the compound according to a), and/or.
d2) 0 to 20%, preferably 0.01 to 20%, more preferably 0.1 to 10%, even more preferably 0.1 to 5%, of one or more pharmaceutically acceptable excipients other than the compounds according to b) and c),
with the proviso that the sum of a), b), c), d1) and d2) makes up to 99%, 99.9% or 100% of the composition,
and preferably with
the further proviso that 50 to 100% of the cyclo-(Arg-Gly-Asp-DPhe-NMeVal), the pharmaceutically acceptable derivatives, solvates and/or salts thereof is present in the composition as solid particles of solid form A1.

Preferably, said compositions are free or essentially free of pharmaceutically active ingredients other than the compounds according to a).

Preferably in said compositions, the pharmaceutically acceptable excipients other than the compounds according to b) and c) selected from tonicity agents and preservatives, preferably tonicity agents and preservatives as described herein.

[24] Also preferred for use in the methods according to the invention are compositions as described herein or as described in one or more of the paragraphs numbered [1] to [23] and/or the paragraphs relating thereto, comprising,
a) 8 to 60% of solid cyclo-(Arg-Gly-Asp-DPhe-Val) or cyclo-(Arg-Gly-Asp-DPhe-NMeVal),
the pharmaceutically acceptable derivatives, solvates and/or salts thereof, in suspended or suspendable form, b) 0.01 to 60% of one or more lipophilic and/or amphiphilic compounds as described herein and especially as described in one or more of the paragraphs numbered [1] to [14] and preferably also as described in the paragraphs relating thereto, and c) 0 to 89.99% of water, with the proviso that the sum of a), b) and c) makes up to 80 or more %, preferably 90% or more and especially 90 to 100% of the total composition.

[25] Preferred for use in the methods according to the invention are compositions as described herein or as described in one or more of the paragraphs numbered [1] to [24] and/or the paragraphs relating thereto, wherein the molar ratio between the one or more amphiphilic compounds and the one or more oligopeptides is in the range between 0.0001 and 1, more preferably in a range between 0.001 and 0.5 and especially in the range between 0.002 and 0.1, for example about 0.001, about 0.002, about 0.0025, about 0.005, about 0.01, about 0.05, about 0.1 or about 0.5.

Thus, especially preferred for use in the methods according to the invention are compositions as described herein, wherein the molar ratio between the one or more amphiphilic compounds and the one or more oligopeptides is in the range between 0.0001 and 0.05, preferably in the range between 0.0005 and 0.05 and especially in the range between 0.001 and 0.05.

Especially preferred for use in the methods according to the invention is a composition containing cyclo-(Arg-Gly-Asp-DPhe-NMeVal), preferably in the form of a suspension, said composition comprising or essentially consisting of:

a) 15 to 40%, preferably 25 to 35%, of cyclo-(Arg-Gly-Asp-DPhe-NMeVal) having a solubility in water at 20° C. between 6 and 10 mg/ml, more preferably cyclo-(Arg-Gly-Asp-DPhe-NMeVal) in the polymorphic form A1 as described herein, b) 0.01 to 3%, preferably 0.05 to 1% and especially 0.1 to 1% of dimyristoylphosphatidylglycerol (DMPG), more preferably dimyristoylphosphatidylglycerol (DMPG) sodium salt, c) 0.1 to 3%, preferably 0.5 to 2% and especially 0.5 to 1.5% of one or more tonicity agents as described herein, preferably NaCl, d) 0 to 5%, preferably 0 to 2%, more preferably 0 to 1% and especially 0.001 to 1% of one or more pharmaceutically acceptable preservatives as described herein and more preferably one pharmaceutically acceptable preservative as described herein, e) 0 to 5%, preferably 0 to 2%, more preferably 0 to 1% and especially 0.001 to 1% of one or more further pharmaceutically acceptable excipients, and f) 44 to 84.89% of water, more preferably water add 100%, preferably with the proviso that the sum of a), b), c), d), e) and f) sum up to 99% and even more preferably sum up to 100%. The percentages in this regard are preferably selected from % w/v and % w/w and more preferably are % w/w. In this regard, the one or more further pharmaceutically acceptable excipients are preferably other than lipophilic and/or amphiphilic compounds as described herein. In this regard, the one or more pharmaceutically acceptable preservative is preferably selected from Benzyl alcohol, Benzalkonium chloride, Benzethonium chloride, Benzoic acid, Chlorobutanol, Cresol, Methylparaben, Phenol, Propylparaben, Butylparaben, Thimerosal, Sodium benzoate and Phenylmercuric nitrate, more preferably from Benzyl alcohol, Chlorobutanol, Cresol, Methylparaben, Phenol, Propylparaben, Butylparaben and Thimerosal and even more preferably from Phenol, Chlorobutanol, Cresol, Methylparaben, Propylparaben and Thimerosal.

Alternatively preferred for use in the methods according to the invention is a composition, preferably a pharmaceutical composition, comprising a) 5 to 15% of at least one oligopeptide, preferably at least one cyclic oligopeptide, said oligopeptide or cyclic oligopeptide having a solubility in water at 20° C. between 1 mg/ml and 15 mg/ml, preferably between 3 mg/ml and 15 mg/ml, more preferably between 5 mg/ml and 15 mg/ml, more preferably between 2 mg/ml and 10 mg/ml, more preferably between 5 mg/ml and 10 mg/ml, even more preferably between 6 mg/ml and 10 mg/ml, and especially between 5 mg/ml and 9 mg/ml, in the form of solid particles, b) 0.001 to 50%, preferably 0.005 to 40% more preferably, 0.01 to 30% and especially 0.01 to 10%, of one or more lipophilic and/or amphiphilic compounds having a molar weight in the range of 200 g/mol to 2000 g/mol, preferably 300 g/mol to 1500 g/mol, more preferably 500 g/mol to 1000 g/mol, and especially 700 g/mol to 900 g/mol, and optionally c) 0 to 94.999% of water, with the proviso that the sum of a), b) and c) makes up to 40 or more %, preferably 50 or more percent, more preferably 70 or more percent, even more preferably 90 percent or more and especially 95 percent or more, of the total composition.

More preferred for use in the methods according to the invention is a composition as described herein and especially as described in the paragraph above, comprising a) 5 to 15%, preferably 6 to 12%, preferably 8 to 12%, and especially 10 to 12% of at least one oligopeptide, preferably at least one cyclic oligopeptide, more preferably at least one oligopeptide or cyclic oligopeptide as described herein, said oligopeptide or cyclic oligopeptide having a solubility in water at 20° C. between 1 mg/ml and 15 mg/ml, preferably between 3 mg/ml and 15 mg/ml, more preferably between 5 mg/ml and 15 mg/ml, more preferably between 2 mg/ml and 10 mg/ml, more preferably between 5 mg/ml and 10 mg/ml, even more preferably between 6 mg/ml and 10 mg/ml, and especially between 5 mg/ml and 9 mg/ml, in the form of solid particles, b) 0.001 to 25%, preferably 0.005 to 15% more preferably, 0.01 to 10% and especially 0.01 to 5%, of one or more amphiphilic compounds, c) 40 to 94.999%, preferably 50 to 94.999%, more preferably 60 to 94.99%, even more preferably 84.999 to 94.999%, of water, with the proviso that the sum of a), b) and c) makes up to 70 or more %, preferably 80 or more %, more preferably 90 or more %, even more preferably 95 or more % and especially 95 to 99.9% of the total composition.

Even more preferred for use in the methods according to the invention is a composition as described in one or more of the two paragraphs above, wherein the one or more amphiphilic compounds are selected from b1) fatty acid mono-, di- or polyesters of phosphatidyl- or sulfatidyl-polyoles, and derivatives, salts and/or alcoholates thereof, and b2) fatty alcohol mono-, di- or polyethers of phosphatidyl- or sulfatidyl-polyoles, and derivatives, salts and/or alcoholates thereof.

Even more preferred for use in the methods according to the invention is a composition as described in one or more of the three paragraphs above, wherein amphiphilic compounds and/or the fatty acid di- or polyesters of polyphosphatidyl-polyoles are selected from the group consisting of dioleoylphosphatidylglycerol, dimyristoylphosphatidylglycerol, dimyristoylphosphatidylcholine, distearoylphosphatidylglycerol, dioleoylglycerophosphocholine, dipalmitoylglycerophosphoglycerol, distearoylglycerophosphoethanolamine, egg phosphatidylcholine and soy phosphatidylcholine, more preferably dioleoylphosphatidylglycerol and/or dimyristoylphosphatidylglycerol, and especially dimyristoylphosphatidylglycerol, and the pharmaceutically acceptable derivatives, salts and/or alcoholates thereof.

Even more preferred for use in the methods according to the invention is a composition as described in one or more of the four paragraphs above, wherein said oligopeptide or cyclic oligopeptide is selected from cyclo-(Arg-Gly-Asp-DPhe-NMeVal), an anhydrate of the inner salt of cyclo-(Arg-Gly-Asp-DPhe-NMeVal) and the crystalline form A1 of the inner salt of cyclo-(Arg-Gly-Asp-DPhe-NMeVal), said oligopeptide or cyclic oligopeptide preferably having a solubility in water at 20° C. between 1 mg/ml and 15 mg/ml, preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml.

Thus, said oligopeptide or cyclic oligopeptide having a solubility in water at 20° C. between 1 mg/ml and 25 mg/ml, preferably between 2 mg/ml and 20 mg/ml, more preferably between 5 mg/ml and 20 mg/ml, more preferably between 2 mg/ml and 15 mg/ml, more preferably between 5 mg/ml and 15 mg/ml, even more preferably between 3 mg/ml and 10 mg/ml, even more preferably between 6 mg/ml and 10 mg/ml, and especially between 5 mg/ml and 9 mg/ml, is preferably selected from cyclo-(Arg-Gly-Asp-DPhe-NMeVal), an anhydrate of the inner salt of cyclo-(Arg-Gly-Asp-DPhe-NMeVal), a crystalline anhydrate of the inner salt of cyclo-(Arg-Gly-Asp-DPhe-NMeVal), and the crystalline form A1 of the inner salt of cyclo-(Arg-Gly-Asp-DPhe-NMeVal) an. Thus, said oligopeptide or cyclic oligopeptide preferably comprises, essentially consists or consists of crystalline form A1.

Thus, also preferred for use in the methods according to the invention is a composition containing cyclo-(Arg-Gly-Asp-DPhe-NMeVal) in the form of a suspension, said composition comprising or essentially consisting of:
a) 5 to 15%, preferably 6 to 12%, preferably 8 to 12%, and especially 10 to 12%, of cyclo-(Arg-Gly-Asp-DPhe-NMeVal) having a solubility in water at 20° C. between 6 and 10 mg/ml, more preferably cyclo-(Arg-Gly-Asp-DPhe-NMeVal) in the polymorphic form A1 as described herein,
b) 0.005 to 2%, preferably 0.001 to 1% and especially 0.05 to 1% of dimyristoylphosphatidylglycerol (DMPG), more preferably dimyristoylphosphatidylglycerol (DMPG) sodium salt,
c) 0.1 to 3%, preferably 0.5 to 2% and especially 0.5 to 1.5% of one or more tonicity agents s described herein, preferably NaCl,
d) 0 to 5%, preferably 0 to 2%, more preferably 0 to 1% and especially 0.001 to 1% of one or more pharmaceutically acceptable preservatives as described herein and more preferably one pharmaceutically acceptable preservative as described herein,
e) 0 to 5%, preferably 0 to 2%, more preferably 0 to 1% and especially 0.001 to 1% of one or more further pharmaceutically acceptable excipients, and
f) 70 to 94.895% of water, more preferably water add 100%, preferably with the proviso that the sum of a), b), c), d), e) and f) sum up to 99% and even more preferably sum up to 100%. The percentages in this regard are preferably selected from % w/v and % w/w and more preferably are % w/w. In this regard, the one or more further pharmaceutically acceptable excipients are preferably other than lipophilic and/or amphiphilic compounds as described herein. In this regard, the one or more pharmaceutically acceptable preservative is preferably selected from Benzyl alcohol, Benzalkonium chloride, Benzethonium chloride, Benzoic acid, Chlorobutanol, Cresol, Methylparaben, Phenol, Propylparaben, Butylparaben, Thimerosal, Sodium benzoate and Phenylmercuric nitrate, more preferably from Benzyl alcohol, Chlorobutanol, Cresol, Methylparaben, Phenol, Propylparaben, Butylparaben and Thimerosal and even more preferably from Phenol, Chlorobutanol, Cresol, Methylparaben, Propylparaben and Thimerosal.

If the compositions contain more than one amphiphilic compound and/or one or more oligopeptides, the molar ratio is preferably the one between the molar amount of all contained oligopeptides and/or the amount of all contained amphiphilic compounds, respectively.

If the compositions contain more than one compound of a respective class of compound, e.g. more than one amphiphilic compound and/or one or more oligopeptide, the percentages given herein preferably relate to the total amount of the respective class of compound, i.e. the total amount of all contained oligopeptides and the total amount of all contained amphiphilic compounds, respectively. The same holds preferably true for the other classes of compounds contained in the compositions according to the invention.

Preferably, the compositions for use in the methods according to the invention and especially the pharmaceutical compositions for use in the methods according to the invention are compositions for subcutaneous (s.c.) administration and/or intramuscular (i.m.) administration. Administration in this regard preferably relates to the administration of said compositions to a mammal, preferably a human mammal, even more preferably to a patient and especially to a human patient. In this regard, subcutaneous administration or subcutaneous is preferably also abbreviated as s.c. administration or s.c., respectively; also in this regard, intramuscular administration or intramuscular is preferably abbreviated as i.m. administration or i.m.

Compositions for use in the methods according to the invention which comprise lipophilic compounds according to b) as defined herein and especially compositions which comprise predominantly or exclusively lipophilic compounds according to b) as defined herein, but which preferably contain no or only minor amounts of amphiphilic compounds according to b) as defined herein, are preferred as pharmaceutical compositions for intramuscular administration.

Compositions for use in the methods according to the invention which comprise amphiphilic compounds according to b) as defined herein and especially compositions which comprise predominantly or exclusively amphiphilic compounds according to b) as defined herein, but which preferably contain no or only minor amounts of lipophilic compounds according to b) as defined herein, are preferred as pharmaceutical compositions for subcutaneous administration.

In the method according to the invention as described herein and especially as described in one or more of the paragraphs numbered [1] to [41] and/or the paragraphs relating thereto, the composition as described herein and especially as described in one or more of the paragraphs numbered 1] to [41] and/or the paragraphs relating thereto is preferably administered to the subject, preferably the mammalian subject and especially to the human subject in a manner that the amount of oligopeptide, cyclic oligopeptide or cyclic RGD-containing oligopeptide administered to said subject is 0.5 mg to 3000 mg per subject and day, more preferably 10 to 2500 mg per subject and per day, and especially 50 to 1000 mg per patient and per day, or, per kilogram body weight, preferably about 0.1 to 100 mg/kg, and
more preferably 1 mg to 50 mg/kg, preferably per dosage unit and more preferably per day, or, per square meter of the body surface, preferably 0.5 mg to 2000 mg/m$^2$, more preferably 5 to 1500 mg/m$^2$, and especially 50 to 1000 mg/m$^2$, preferably per dosage unit and more preferably per day. Said amounts preferably relate on everyday on which the formulation is administered to said subject. Said formulation is preferably suitable to be administered to said subject daily, i.e. once every day, or even two or three times daily, i.e. two times every day or three times every day, for a prolonged time period, i.e. several weeks to several years and more preferably 1 week to 2 or 3 years. Due to the advantageous pharmacokinetic profile of said formulation, said formulation is preferably also suitable to be administered to said subject less frequent, i.e. to times weekly, once weekly or every second week.

In the method according to the invention as described herein and especially as described in one or more of the paragraphs numbered [1] to [41] and/or the paragraphs relating thereto, the composition as described herein and especially as described in one or more of the paragraphs numbered 1] to [41] and/or the paragraphs relating thereto is preferably administered to the subject, preferably the mammalian subject and especially to the human subject in a manner that the amount of oligopeptide, cyclic oligopeptide or cyclic RGD-containing oligopeptide administered to said subject is 2 mg to 9000 mg per subject and per week (weekly dose), more preferably 30 to 7500 mg per subject and per week (weekly dose), and especially 150 to 4500 mg per subject and per week (weekly dose), or, per kilogram body weight, preferably about 0.5 to 200 mg/kg per subject and per week (weekly dose), and more preferably 1 mg to 150 mg/kg per subject and per week (weekly dose), or, per square meter of the body surface, preferably 20 mg to 6000 mg/m$^2$ per subject and per week (weekly dose), more preferably 100 to 3000 mg/m$^2$, and especially 200 to 2000 mg/m$^2$ per subject and per week (weekly dose).

Generally, the Peptide of the formula Cyclo-(Arg-Gly-Asp-DPhe-NMe-Val) and/or the pharmaceutically acceptable derivatives, solvates and/or salts thereof and/or the one or more cancer cotherapeutic agents or further cancer cotherapeutic agents, more preferably the one or more cancer chemotherapeutic agents, can be administered in an amount and/or a regimen as it is known in the art for the respective compound.

In the method according to the invention as described herein and especially as described in one or more of the paragraphs numbered [1] to [41] and/or the paragraphs relating thereto, the composition as described herein and especially as described in one or more of the paragraphs numbered 1] to [41] and/or the paragraphs relating thereto is preferably administered to the human subject in a manner that the amount of cyclo-(Arg-Gly-Asp-DPhe-NMeVal) and the pharmaceutically acceptable derivatives, solvates and/or salts thereof, preferably cyclo-(Arg-Gly-Asp-DPhe-NMe-Val), administered to said subject is 50 mg to 3000 mg per subject and day, more preferably 100 to 2000 mg per subject and per day, even more preferably 100 to 1000 mg per subject and per day and especially 150 to 700 mg per patient and per day, or, per kilogram body weight, preferably about 1 to 30 mg/kg, and more preferably 1 mg to 15 mg/kg, preferably per dosage unit and more preferably per day, or, per square meter of the body surface, preferably 50 mg to 1000 mg/m$^2$, more preferably 50 to 500 mg/m$^2$, and especially 75 to 350 mg/m$^2$, preferably per dosage unit and more preferably per day. Said amounts preferably relate on everyday on which the formulation is administered to said subject. Said formulation is preferably suitable to be administered to said subject daily, i.e. once every day, or even two or three times daily, i.e. two times every day or three times every day, for a prolonged time period, i.e. several weeks to several years and more preferably 1 week to 2 or 3 years. Due to the advantageous pharmacokinetic profile of said formulation, said formulation is preferably also suitable to be administered to said subject less frequent, i.e. to times weekly, once weekly or every second week.

In the method according to the invention as described herein and especially as described in one or more of the paragraphs numbered [1] to [41] and/or the paragraphs relating thereto, the composition as described herein and especially as described in one or more of the paragraphs numbered 1] to [41] and/or the paragraphs relating thereto is preferably administered to the human subject in a manner that the amount of cyclo-(Arg-Gly-Asp-DPhe-NMeVal) and the pharmaceutically acceptable derivatives, solvates and/or salts thereof, preferably cyclo-(Arg-Gly-Asp-DPhe-NMe-Val), administered to said subject is 75 mg to 9000 mg per subject and per week (weekly dose), more preferably 150 to 5000 mg per subject and per week (weekly dose), even more preferably 300 to 4500 mg per subject and per week (weekly dose) and especially 600 to 2500 mg per subject and per week (weekly dose).

Said weekly dose is preferably administered to said subject for at least one week, preferably at least two weeks, more preferably at least four weeks and especially at least eight weeks, preferably without preferably without a pause or substantially without a pause. Preferably, due to the advantageous properties of said composition, the duration of said weekly administration is in principle not limited. Thus, said weekly dose is preferably administered to said subject for a time period 1 to 208 weeks, more preferably 2 to 156 weeks, even more preferably 4 to 156 weeks and especially 4 to 104 weeks or 4 to 52 weeks, preferably without a pause or substantially without a pause.

Especially preferred is a method for treating disorders, especially disorder selected from cancer and/or metastases thereof, preferably cancer and/or metastases thereof as described herein, wherein a composition as described herein comprising cyclo-(Arg-Gly-Asp-DPhe-NMeVal) and the pharmaceutically acceptable derivatives, solvates and/or salts thereof, preferably cyclo-(Arg-Gly-Asp-DPhe-NMe-Val), in an amount of 75 to 500 mg (preferably corresponding to about 7.5 to 50% cyclo-(Arg-Gly-Asp-DPhe-NMe-Valand the pharmaceutically acceptable derivatives, solvates and/or salts thereof, preferably cyclo-(Arg-Gly-Asp-DPhe-NMeVal), respectively) is administered to a human subject, preferably from once weekly to 3 times daily, more preferably from two times weekly to two times daily and especially from five times weekly to once or twice every day.

Especially preferred is a method for treating disorders, especially disorder selected from cancer and/or metastases thereof, preferably cancer and/or metastases thereof as described herein, wherein a composition as described herein comprising cyclo-(Arg-Gly-Asp-DPhe-NMeVal) and the pharmaceutically acceptable derivatives, solvates and/or salts thereof, preferably cyclo-(Arg-Gly-Asp-DPhe-NMeVal), in an amount of 100 to 400 mg (preferably corresponding to about 10 to 40% cyclo-(Arg-Gly-Asp-DPhe-NMeValand the pharmaceutically acceptable derivatives, solvates and/or salts thereof, preferably cyclo-(Arg-Gly-Asp-DPhe-NMeVal), respectively) is administered to a human subject, preferably from once weekly to 3 times daily, more preferably from two times weekly to two times daily and especially from five times weekly to once or twice every day.

Especially preferred is a method for treating disorders, especially disorder selected from cancer and/or metastases thereof, preferably cancer and/or metastases thereof as described herein, wherein a composition as described herein comprising cyclo-(Arg-Gly-Asp-DPhe-NMeVal) and the pharmaceutically acceptable derivatives, solvates and/or salts thereof, preferably cyclo-(Arg-Gly-Asp-DPhe-NMeVal), in an amount of 100 to 400 mg (preferably corresponding to about 10 to 40% cyclo-(Arg-Gly-Asp-DPhe-NMeValand the pharmaceutically acceptable derivatives, solvates and/or salts thereof, preferably cyclo-(Arg-Gly-Asp-DPhe-NMeVal), respectively) is administered to a human subject, preferably from once weekly to 3 times daily, more preferably from two times weekly to two times daily and especially from five times weekly to once or twice every day. Especially preferred is a method for treating disorders, especially disorder selected from cancer and/or metastases thereof, preferably cancer and/or metastases thereof as described herein, wherein a composition as described herein comprising cyclo-(Arg-Gly-Asp-DPhe-NMeVal) and the pharmaceutically acceptable derivatives, solvates and/or salts thereof, preferably cyclo-(Arg-Gly-Asp-DPhe-NMeVal), in an amount of 150 to 300 mg (preferably corresponding to about 15 to 30% cyclo-(Arg-Gly-Asp-DPhe-NMeValand the pharmaceutically acceptable derivatives, solvates and/or salts thereof, preferably cyclo-(Arg-Gly-Asp-DPhe-NMeVal), respectively) is administered to a human subject, preferably from once weekly to 3 times daily, more preferably from two times weekly to two times daily and especially from five times weekly to once or twice every day.

Suitable routes, manners and devices for administering the compositions for use in the method according to the invention are known and described in the art.

Preferably, the compositions for use in the method according to the invention are administered to the subject parenterally.

Even more preferably, the compositions for use in the method according to invention are administered to the subject via an injection.

Even more preferably, the compositions for use in the method according to the invention are administered to the subject subcutaneously and/or intramuscular.

Especially preferably, the compositions for use in the method according to the invention are administered to the subject by subcutaneous and/or intramuscular injection, even more preferably by subcutaneous injection.

Suitable devices for administering said compositions to the subject are known in the art. Preferred according to the invention are syringes and/or other devices for injection of fluid compositions into the body of the subject. Suitable such devices are known and described in the art.

Especially preferred syringes and devices for administering said compositions a the subject, preferably a human subject, are syringes and devices that allow a self administration by said subject. Suitable such devices are known and described in the art.

A further preferred subject of the instant invention is a process for the manufacture of a composition as described herein.

[26] Preferably, the process for the manufacture of a composition as described herein, or as described in one or more of the paragraphs numbered [1] to [25] and/or the paragraphs relating thereto, comprises one or more of the following steps, preferably two or more and more preferably comprises all the given steps:
i) solubilising the one or more amphiphilic compounds in water,
ii) adding or preferably suspending the one or more oligopeptides in the mixture or solution, preferably solution, obtained according to i), and optionally
iii) adding the of one or more pharmaceutically active ingredients other than the compound according to a), and/or the one or more pharmaceutically acceptable excipients other than the water and the one or more amphiphilic compounds.

Even more preferably, the process for the manufacture of a composition as described herein comprises one or more of the following steps, preferably two or more and more preferably comprises all the given steps:
i) solubilising the one or more amphiphilic compounds in water,
ii) adding or preferably suspending the one or more oligopeptides in the mixture or solution, preferably solution, obtained according to i), and optionally
iii) adding the one or more pharmaceutically acceptable excipients, selected from the group consisting of tonicity agents and preservatives, optionally followed by
iv) adding the of one or more pharmaceutically active ingredients other than the compound according to a).

Preferably, the mixture obtained according to steps ii), iii) and/or iv) is mixed, stirred and/or agitated until a stable particle size and/or particle size distribution is obtained.

Preferably, the two or more of the steps of the above given processes are performed in the above given order.

Preferably, an alternative process for the manufacture of a composition as described herein comprises one or more of the following steps, preferably two or more and more preferably comprises all the given steps:
i) contacting the one or more oligopeptides with the one or more lipophilic compounds; and optionally
ii) mixing, stirring and/or agitating the mixture according to step i), preferably until a stable particle size and/or particle size distribution is obtained, and/or
iii) adding the of one or more pharmaceutically active ingredients other than the compound according to a), and/or the one or more pharmaceutically acceptable excipients other than the water and the one or more amphiphilic compounds.

Even more preferably, the process for the manufacture of a composition as described herein comprises one or more of the following steps, preferably two or more and more preferably comprises all the given steps:
i) contacting the one or more oligopeptides with the one or more lipophilic compounds; and optionally
ii) mixing, stirring and/or agitating the mixture according to step i), preferably until a stable particle size and/or particle size distribution is obtained, and optionally
iii) adding the one or more pharmaceutically acceptable excipients, selected from the group consisting of tonicity agents and preservatives, optionally followed by
iv) adding the of one or more pharmaceutically active ingredients other than the compound according to a).

Preferably, the two or more of the steps of the above given processes are performed in the above given order.

Advantageously, the oligopeptide, preferably the solid oligopeptide and especially the particulate solid oligopeptide preferably undergoes degradation (preferably spontaneous degradation or self-degradation) or even preferably micronization (preferably spontaneous micronization or self-micronization) to yield suspended or suspendable particles on contacting it with the lipophilic compound or the amphiphilic compound, the latter preferably in the presence of water. Generally, mixing, stirring and/or agitating accelerates this process.

Means for solubilising the one or more amphiphilic compounds in water in step i), the adding or preferably suspending of the one or more oligopeptides in step ii) and/or the addition of the further compounds in step iii) can advantageously be performed by mixing, stirring and/or agitating the respective compounds in the respective step.

Preferably, the mixing, stirring and/or agitating is continued after the completion of the one or more reaction steps, preferably after the completion of all reaction steps. Generally, the mixing, stirring and/or agitating is continued until a stable suspension and/or stable particle size distribution in the suspension is obtained. The mixing, stirring and/or agitating time is mainly dependent from the respective particle size of the solid oligopeptide. Thus, starting with coarse particles of the oligopeptide generally leads to longer processing times and/or mixing, stirring and/or agitating times, whereas starting with fine particles of the oligopeptides or micronized oligopeptide will lead to shorter processing times and/or shorter mixing, stirring and/or agitating times or generally a reduced need for mixing, stirring and/or agitating.

Thus, the mixing, stirring and/or agitating is then continued 1 to 96 hours, preferably 1 to 72 hours, more preferably 1 to 48 hours, even more preferably 2 to 72 hours and especially 2 to 48 hours. Even more preferably, the mixing, stirring and/or agitating is then continued 2 to 96 hours, preferably 2 to 72 hours, more preferably 2 to 48 hours, even more preferably 3 to 72 hours and especially 3 to 48 hours.

Generally, the process for the manufacture of the compositions according to the invention, preferably including the mixing, stirring and/or agitating time after the completion of the one or more reaction steps, takes a processing time of 1 to 100 hours, preferably 1 to 80 hours, more preferably 1 to 56 hours, even more preferably 2 to 78 hours and especially 2 to 56 hours.

Thus, on starting with already micronized oligopeptide, processing times and especially mixing, stirring and/or agitating times will be in the range of 1 to 24 hours, more preferably 1 to 12 hours, more preferably 2 to 12 hours, even more preferably 2 to 8 hours and especially 3 to 6 hours, for example about 3 hours, about 4 hours, about 5 hours or about 6 hours.

Thus, on starting with coarse particles of the oligopeptide, processing times and especially mixing, stirring and/or agitating times will be in the range of 3 to 96 hours, more preferably 4 to 72 hours, more preferably 6 to 48 hours, even more preferably 8 to 48 hours and especially 10 to 48 hours, for example about 3 hours, about 4 hours, about 5 hours or about 6 hours.

Thus, preferred is a process as described herein and especially as described in the paragraph numbered [24] and preferably also the paragraphs relating thereto, wherein one or more, preferably two or more and especially three or four of these steps comprise mixing, stirring and/or agitating the respective compounds in the respective step.

Preferably, the oligopeptide is employed in the process in a solid form, preferably a solid particulate form an even more preferably in a solid crystalline particulate form. Even more preferably the oligopeptide is employed in the process in a milled or even more preferably micronized form.

Generally, the process according to the invention is performed at normal temperatures, such as room temperature (20° C. or 25° C., preferably 20° C.), or at elevated temperatures, preferably normal temperatures or moderately elevated temperatures. Moderately elevated temperatures according to the invention preferably are the range between 25° C. and 80° C., more preferably 30° C. and 60° C. and especially between 30° C. and 50° C., for example at about 30° C., about 40° C. or about 50° C.

Preferably, only one, or only one or two, of the process steps are performed at elevated temperatures and even more preferably moderately elevated temperatures.

Depending on the physical properties of the amphiphilic compound used in the instant process, it can be advantageous to perform the solubilising the one or more amphiphilic compounds in water at elevated temperatures and more preferably at moderately elevated temperatures as described herein. Even more preferably, only this step is performed at moderately elevated temperatures.

[27] A preferred subject of the instant invention is a composition for use in the method of treatment as described herein, obtainable by the process as described herein and especially as described in the paragraph numbered [26] and preferably also the paragraphs relating thereto and especially as described in one or more of the examples 1 to 9 or 1 to 15.

Thus, a preferred subject of the instant invention is a composition for use in the method of treatment as described herein, obtainable by the process according to one or more of the examples 1 to 9 or 1 to 15.

Means for adding, mixing, stirring and/or agitating the compounds in the respective steps are known in the art.

The process for the manufacture according to the invention is described in more detail in the examples.

Another preferred subject of the invention are powders, preferably free-flowing and/or reconstitutable powders for use in the method of treatment as described herein, which correspond to the compositions as described herein but are free of or essentially free of water or other solvents. Preferably, such powders are obtainable from the compositions as described herein that contain water and/or are obtainable by the process for the manufacture of the compositions as described herein, by suitable steps that are known in the art for reducing the amount of water and/or other solvents from said compositions, or that are known in the art for removing the water and/or the other solvents. Preferred suitable steps are selected from drying, vacuum drying, fluid-drying, spray-drying, evaporation and lyophilisation, and combinations thereof. These steps can be optionally performed in the presence of suitable pharmaceutically acceptable excipients that facilitate the drying step and/or the reconstitution or resuspension of said powders into injectable formulations or compositions. Suitable pharmaceutically acceptable excipients for that purpose are known in the art. Preferably, pharmaceutically acceptable excipients for that purpose preferably include carbohydrates or sugars, e.g. mannitol, dispersing aids, binders, and the like.

Thus, a preferred subject of the invention is a composition for use in the method of treatment as described herein, preferably in the form a powder, more preferably a free-flowing and/or reconstitutable powder, comprising a) 80 to 99.99% of at least one oligopeptide, said oligopeptide having a solubility in water at 20° C. between 5 mg/ml and 20 mg/ml,
b) 0.01 to 20% of one or more lipophilic and/or amphiphilic compounds having a molar weight in the range of 200 g/mol to 2000 g/mol, and
c) 0 to 20% of water,
with the proviso that the sum of a), b) and c) sums up to 80 or more %, preferably to 90 or more %, more preferably to 95 or more % and especially to 99-100% of the total composition.

Thus, a more preferred subject of the invention is a composition, preferably in the form a powder, more preferably a free-flowing and/or reconstitutable powder for use in the method of treatment as described herein, comprising
a) 80 to 99.99% of cyclo-(Arg-Gly-Asp-DPhe-NMeVal), the pharmaceutically acceptable derivatives, solvates and/or salts thereof, preferably having a solubility in water at 20° C. between 5 mg/ml and 20 mg/ml,
b) 0.01 to 20% of one or more lipophilic and/or amphiphilic compounds as described herein and more preferably selected from dioleoylphosphatidylglycerol and dimyristoylphosphatidylglycerol, and
c) 0 to 20% of water,
with the proviso that the sum of a), b) and c) sums up to 80 or more %, more preferably to 90 or more % and especially to 95-100%, of the total composition.

Thus, and even more preferred subject of the invention is a composition, preferably in the form a powder, more preferably a free-flowing and/or reconstitutable powder for use in the method of treatment according to the invention, comprising
a) 80 to 99.99% of cyclo-(Arg-Gly-Asp-DPhe-NMeVal), the pharmaceutically acceptable derivatives, solvates and/or salts thereof, preferably having a solubility in water at 20° C. between 5 mg/ml and 20 mg/ml,
b) 0.01 to 20% of one or more lipophilic and/or amphiphilic compounds as described herein and more preferably selected from dioleoylphosphatidylglycerol and dimyristoylphosphatidylglycerol, and optionally
c) 0 to 20% of one or more pharmaceutically acceptable excipients,
with the proviso that the sum of a), b) and c) sums up to 90% or more, preferably 95% or more and especially 99 to 100% of the total composition, and with the further proviso that the water content of said composition is in the range between 0.001 and 10%, more preferably 0.01 and 5% and especially 0.01 to 1%.

[28a] Thus, preferred is a composition in the form of a free-flowing or reconstitutable powder for use in the method of treatment according to the invention, which corresponds to a composition as described herein and more preferably water-based compositions as described herein, wherein the water-content is reduced to residual water content in the range of 0 to 20% or 0.001 to 10%, preferably based on the total (dried) composition or (dried) powder and more preferably based on the total weight of the (dried) composition or (dried) powder. Water-based compositions in this regard are preferably compositions that that contain 20% more, preferably 30% or more, more preferably 40% more and especially 60% or more of water, preferably based on the total composition. Preferably, such water based compositions contain 30 to 90%, more preferably 40 to 80% and especially 50 to 75% of water, preferably based on the total composition.

[28b] Thus, preferred is a composition form of a free-flowing or reconstitutable powder, obtainable from a composition as described herein and more preferably a water-based composition as described herein by reducing the water content until a residual water content of 0 to 20% or 0.001 to 10 percent is achieved, preferably based on the total (dried) composition or (dried) powder and more preferably based on the total weight of the (dried) composition or (dried) powder.

Thus, the compositions for use in the method of treatment according to the invention are preferably either
a) in the form of suspensions, preferably a suspension of the contained oligopeptide in an aqueous medium, such as water, water for injection, buffered water, phosphate-buffered saline or other pharmaceutically acceptable aqueous media, or
b) in the form of dried powders, preferably powders which are substantially free or free of water, which are obtainable from the (aqueous) compositions as described herein, and which can preferably be resuspended in such an equation medium as described before.

Preferably, both the compositions in the form of (aqueous) suspensions as well as the compositions in the form of (dried) powders are suitable for injection into a patient or subject, preferably suitable for a subcutaneous injection into a patient or subject, the suspensions preferably directly and the powders obviously after resuspension or re-constitution in an aqueous medium as described before.

[29a] Preferably, the compositions for use in the method of treatment according to the invention comprise 10% or more, preferably 30% or more, more preferably 50% or more, even more preferably 70% or more and especially 70 to 99%, 70 to 99.9% or 80 to 99.99, of the contained one or more oligopeptides, cyclic oligopeptides or cyclo-(Arg-Gly-Asp-DPhe-NMeVal) in the form of solid particles and/or solid crystalline particles.

[29b] Preferably, the solid compositions for use in the method of treatment according to the invention comprise 50% or more, preferably 70% or more, more preferably 90% or more, even more preferably 95% or more and especially 80 to 99%, 80 to 99.9% or 90 to 99.99, of the contained one or more oligopeptides, cyclic oligopeptides or cyclo-(Arg-Gly-Asp-DPhe-NMeVal) in the form of solid particles and/or solid crystalline particles.

[30] Thus, preferred are compositions as described herein for use in the method of treatment according to the invention, wherein the one or more oligopeptides, cyclic oligopeptides or cyclo-(Arg-Gly-Asp-DPhe-NMeVal) are at least partly present in the form of solid particles and/or solid crystalline particles, said particles having an average particle size or an effective average particle size in the range of 5 µm to 250 µm, 8 µm to 150 µm, 10 µm to 100 µm, 10 µm to 80 µm, and especially 15 µm to 60 µm. In this regard, the average particle size or effective average particle size is volume-weighted or number-weighted, preferably volume-weighted. Preferably, it is determined as described herein. At least partly present in this regard preferably means 10% or more, preferably 30% or more, more preferably 50% or more, even more preferably 70% or more and especially 70 to 99%, 70 to 99.9% or 80 to 99.99. Percentages in this regard are preferably given as described herein and more preferably are % w/w.

Preferably, said cyclo-(Arg-Gly-Asp-DPhe-NMeVal) in the form of solid particles and/or solid crystalline particles is preferably selected from an anhydrate of the inner salt of cyclo-(Arg-Gly-Asp-DPhe-NMeVal), a crystalline anhydrate of the inner salt of cyclo-(Arg-Gly-Asp-DPhe-NMeVal), and the crystalline form A1 of the inner salt of cyclo-(Arg-Gly-Asp-DPhe-NMeVal) an. Thus, said solid particles and/or solid crystalline particles preferably comprise crystalline form A1 and more preferably essentially consist of crystalline form A1 or consist of crystalline form A1.

A preferred subject of the instant invention is the use of cyclo-(Arg-Gly-Asp-DPhe-NMeVal), the pharmaceutically acceptable derivatives, solvates and/or salts thereof and especially the use of the inner salt of cyclo-(Arg-Gly-Asp-DPhe-NMeVal), a crystalline anhydrate of the inner salt of cyclo-(Arg-Gly-Asp-DPhe-NMeVal), and/or the crystalline form A1 of the inner salt of cyclo-(Arg-Gly-Asp-DPhe-NMeVal), for the manufacture of a composition as described herein and especially for a pharmaceutical composition as described herein for use in the method according to the invention. Thus, a preferred subject of the instant invention is the use of crystalline form A1 for the manufacture of a composition as described herein and especially for a pharmaceutical composition as described herein for use in the method according to the invention.

Thus, a preferred subject of the instant invention are compositions, preferably pharmaceutical compositions and especially compositions or pharmaceutical compositions as described herein for use in the method according to the invention, that comprise crystalline form A1. Preferably, said compositions comprise 5 to 100%, more preferably 5 to 99%, even more preferably 10 to 70%, even more preferably 12 to 60%, even more preferably 15 to 50% and especially 20 to 40%, of crystalline form A1, e.g. about 10%, about 15%, about 20%, about 25%, about 30% or about 35% of crystalline form A1. Said percentages are preferably based on the total composition. Percentages in this regard are preferably given as described herein and more preferably are % w/w or % w/v, and especially are % w/w.

A preferred subject of the instant invention is the use of the compositions as described herein and/or the use of the solid compositions as described herein as a pharmaceutical, preferably as a pharmaceutical in the treatment of disorders as described herein. A preferred subject of the instant invention is the use of the compositions as described in this specification, as described in the claims and/or as described or essentially described in the Examples as a pharmaceutical, preferably as a pharmaceutical in the treatment of disorders as described herein. Preferred Examples in this regard are one or more of Examples 1 to 17 and/or Example 18.

If not explicitly stated otherwise, the terms "solid material(s) as described herein", "solid form(s) as described herein", "crystalline form(s) as described herein", "solvate(s) as described herein", "hydrate(s) as described herein", "tetrasolvate(s) as described herein", "tetrahydrate(s) as described herein", "anhydrate(s) as described herein", "alcoholate(s) as described herein", "methanolate(s) as described herein", "ethanolate(s) as described herein", "tetraalcoholate(s) as described herein", "tetramethanolate(s) as described herein" and/or "tetraethanolate(s) as described herein" preferably refer to the "solid material(s)", "solid form(s)", "crystalline form(s)", "solvate(s)", "hydrate(s)", "tetrasolvate(s)", "tetrahydrate(s)", "anhydrate(s)", "alcoholate(s)", "methanolate(s)", "ethanolate(s)", "tetraalcoholate(s)", "tetramethanolate(s)" and/or "tetraethanolate(s)" of the compound of formula Id.

Methods and means for determining the solubilities of the compounds described herein are known in the art. Preferably, the solubilities of the compounds described herein are determined by methods and means accepted by the FDA and/or EMEA.

Solubility in this regard is preferably refers to the saturation solubility, which is preferably the maximum mass of the respective compound, which can be solubilised or dissolved in a solvent at a respective temperature and at a specific pressure, preferably atmospheric pressure.

With regard to the present invention, the solubilities in water given herein for the respective compound preferably refer to the saturation solubility of the respective compound in water, which is preferably the maximum mass of the respective compound which can be solubilised or dissolved in water at the respective given temperature and at the respective pressure, preferably atmospheric pressure, and even more preferably the maximum mass of the respective compound which can be solubilised or dissolved in water at the respective temperatures given herein, i.e. 20° C. and/or 25° C., preferably 20° C., a and at the respective pressure, preferably atmospheric pressure, which is here preferably normal atmospheric pressure and especially the standardised "normal" atmospheric pressure, i.e. 1 atm=1,01325 bar.

Even more preferably, they can be determined by the method described below:

10 mL of solvent is placed in an amber glass ampul and sufficient substance is added to yield a distinct sediment that remains on the bottom after mixing thoroughly. After standing for 15 minutes and mixing again the ampuls are sealed and shaken in a thermostatically controlled water bath (20° C./16 hours or 25° C./16 hours, preferably 20° C./16 hours). Afterwards the ampuls are opened and the supernatant solution is filtered until the filtrate is clear. The content of the substance is determined photometrically in an aliquot by means of the specific adsorption coefficient. The respective dilution of the solvent without substance serves as blank. The solubility is expressed in the dimension of g substance in 100 mL or mg substance in 1 mL, preferably in mg substance in 1 mL. Preferably, this method is performed at normal atmospheric pressure and especially at the standardised "normal" atmospheric pressure, i.e. 1 atm= 1,01325 bar.

The term "particle size" as used herein is known and understood in the art. Preferably, the particle size is determined on the basis of the weight average particle size, preferably as measured by conventional particle size measuring techniques well known to those skilled in the art. Such techniques preferably include, for example, sedimentation field flow fractionation, photon correlation spectroscopy, light scattering, and disk centrifugation.

The term "average particle size" as used herein is known and understood in the art. Preferably, the average particle size is selected from the weight-average particle size, the volume-weighted average particle size and the number-weighted average particle size.

Preferably, the particle size and/or the average particle size is measured by light-scattering methods, microscopy or other appropriate methods known in the art. Appropriate methods in this regard preferably include, but are not limited to sedimentation field flow fractionation, photon correlation spectroscopy, light scattering, laser dynamic light scattering, and disk centrifugation. Furthermore, dynamic light scattering methods (e.g., photocorrelation spectroscopy, laser diffraction, low angle laser light scattering (LALLS), medium-angle laser light scattering (MALLS), light obscuration methods (Courter method, for example), rheology, or microscopy (light or electron) can be used.

The determination of the particle size distribution is especially preferably performed by laser diffraction, preferably on a Malvern Mastersizer 2000, preferably using the wet module Hydro 2000 SM. The evaluation model is preferably Universal (normal sensitivity), the dispersion medium is preferably saturated placebo solution, the stirrer speed is preferably about 2000 rpm, the obscuration is preferably 10-15%, the background measuring time is preferably about 7500 ms (milliseconds), and/or the measuring time is preferably about 7500 ms.

[31] A preferred subject of the instant invention is the use of cyclo-(Arg-Gly-Asp-DPhe-NMeVal), the pharmaceutically acceptable derivatives, solvates and/or salts thereof, preferably cyclo-(Arg-Gly-Asp-DPhe-NMeVal), for the manufacture of a composition as described herein and especially as described in one or more of the paragraphs numbered [1] to [32] and/or the paragraphs relating thereto that is administered to a subject in a method for treating disorders, preferably disorders as described herein and especially disorders as described in one or more of the paragraphs numbered [1] to [3], [33] to [41] and and/or the paragraphs relating thereto.

An especially preferred subject of the instant invention is the use of cyclo-(Arg-Gly-Asp-DPhe-NMeVal), the pharmaceutically acceptable derivatives, solvates and/or salts thereof, preferably cyclo-(Arg-Gly-Asp-DPhe-NMeVal), for the manufacture of a composition for the treatment of disorders, wherein the composition is as described herein and especially as described in one or more of the paragraphs numbered [1] to [32] and/or the paragraphs relating thereto, and preferably wherein disorders to be treated are as described herein and especially preferably are as described in one or more of the paragraphs numbered [1] to [3], [33] to [41] and and/or the paragraphs relating thereto.

[32] Another preferred subject of the invention relates to the use of
i) the composition as described herein and especially as described in one or more of the paragraphs numbered [1] to [32] and/or the paragraphs relating thereto,
and/or
ii) the solid composition as described herein and especially as described in one or more of the paragraphs numbered [1] to [29] and/or the paragraphs relating thereto, and especially as described in the paragraphs numbered [1] and [29]
as a pharmaceutical for treating disorders, preferably disorders as described herein and especially disorders as described in one or more of the paragraphs numbered [1] to [3], [33] to [41] and/or the paragraphs relating thereto.

The term "disorders" is known and understood in the art. Preferably, the disorders to be treated with the composition according to the invention are hyperproliferative disorders, more preferably oncologic disorders and especially cancerous disorders.

[33] Preferably, the disorders to be treated are selected from cancer and metastases thereof.

Preferably, the cancers to be treated are selected from solid tumours and/or metastases thereof.

The terms "hyperproliferative disorders", "oncologic disorders", "cancer", "solid tumours" and "metastases" are known and understood in the art.

The terms "cancer" and/or "tumor" preferably refer to or describe the physiological condition in subjects, preferably mammalian subjects and even more preferably humans, that is typically characterized by upregulated or preferably unregulated cell growth, even more preferably benign and/or malignant cell growth and especially malignant cell growth. Especially preferably, the term "cancer" as used herein includes malignant neoplasms or consists of malignant neoplasms.

Typically, the terms "cancer" or "malignant neoplasms" describe a class of diseases in which a group of cells display uncontrolled growth, invasion that intrudes upon and destroys adjacent tissues, and sometimes metastasis, or spreading to other locations in the body via lymph or blood.

The term "metastases" (singular: metastasis) is known and understood in the art.

In the context of the present invention metastasis or metastatic disease (sometimes abbreviated mets), preferably refers to the spread of a cancerous disease from one organ or part to another organ or part, preferably a non-adjacent organ or part. The word metastasis means "displacement" in Greek. The plural is metastases.

According to an established theory, cancer occurs after a single cell in a tissue is progressively genetically damaged to produce a cancer stem cell possessing a malignant phenotype. These cancer stem cells are thought to be able to undergo uncontrolled abnormal mitosis, which would then serve to increase the total number of cancer cells at that location. When the area of cancer cells at the originating site become clinically detectable, it is preferably called primary tumor. Some cancer cells also are also thought to acquire the ability to penetrate and infiltrate surrounding normal tissues in the local area, forming a new tumor. The newly formed "daughter" tumor in the adjacent site within the tissue is preferably called a local metastasis.

Some cancer cells are thought to be able to acquire the ability to penetrate the walls of lymphatic and/or blood vessels, after which they would then be able to circulate through the bloodstream (circulating tumor cells) to other sites and tissues in the body. This process is preferably known as lymphatic or hematogeneous spread, respectively.

After the tumor cells come to rest at another site, they seem to be able to re-penetrate through the vessel or walls, continue to multiply, and eventually another clinically detectable tumor is formed. This new tumor is known as a metastatic (or secondary) tumor. Metastasis is one of three hallmarks of malignancy (contrast benign tumors). Most tumors or malignant neoplasms can metastasize, although in varying degrees.

When tumor cells metastasize, the new tumor is preferably called a secondary or metastatic tumor, and its cells are like those in the original tumor. This means, for example, that, if breast cancer metastasizes to the lungs, the secondary tumor is made up of abnormal breast cells, not of abnormal lung cells. The tumor in the lung is then called metastatic breast cancer, not lung cancer.

Cancer cells may spread to lymph nodes (regional lymph nodes) near the primary tumor. This is called nodal involvement, positive nodes, or regional disease. ("Positive nodes" is a term that would be used by medical specialists to describe a patient's condition, meaning that the patient's lymph nodes near the primary tumor tested positive for malignancy. It is common medical practice to test by biopsy at least two lymph nodes near a tumor site when doing surgery to examine or remove a tumor.) Localized spread to regional lymph nodes near the primary tumor is preferably not counted as metastasis, although this is a sign of worse prognosis. Transport through lymphatics is the most common pathway for the initial dissemination of cancers or carcinomas.

There is a propensity for certain tumors to seed in particular organs. For example, prostate cancer usually metastasizes to the bones. In a similar manner, colon cancer has a tendency to metastasize to the liver. It is believed that it is difficult for cancer cells to survive outside their region of origin, so in order to metastasize they must find a location with similar characteristics. For example, breast tumor cells, which gather calcium ions from breast milk, metastasize to bone tissue, where they can gather calcium ions from bone. Malignant melanoma spreads to the brain, presumably because neural tissue and melanocytes arise from the same cell line in the embryo.

It is theorized that metastasis always coincides with a primary cancer, and, as such, is a tumor that started from a cancer cell or cells in another part of the body. However, over 10% of patients presenting to oncology units will have metastases without a primary tumor found. In these cases, doctors refer to the primary tumor as "unknown" or "occult," and the patient is said to have cancer of unknown primary origin (CUP) or Unknown Primary Tumors (UPT). However, the use of immunohistochemistry has permitted pathologists to give an identity to many of these metastases. However, imaging of the indicated area only occasionally reveals a primary. In rare cases (e.g., of melanoma), no primary tumor is found, even on autopsy. It is therefore thought that some primary tumors can regress completely, but leave their metastases behind. Despite the use of various techniques, in some cases the primary tumor remains unidentified.

The formation of metastasis or metastases (via the metastatic process) is deemed to be a multistep event and represents the most dreadful aspect of cancer. At the moment of diagnosis, cancers are frequently far advanced in their natural history, and the presence of metastases is a common event. In fact, approximately 30% of patients have detectable metastases at the moment of clinical diagnosis and a further 30% of patients have occult metastases. Metastases can be disseminated and they can infest different organs at the same time, or localize to a specific organ. In the case of localized disease, surgery is the treatment of choice; however recurrence and prognosis depend on many criteria such as: resectability, patient's clinical situation, and number of metastases.

After resection, recurrence is common, suggesting that micrometastatic foci are present at the moment of diagnosis. Systemic chemotherapy is an ideal setting but only few patients are cured by it, and in the majority systemic chemotherapy fails. Many physiological barriers and pharmacokinetic parameters contribute to decrease its efficacy.

Liver, lungs and lymph nodes are filtration organs and therefore inclined to metastasization. The poor chemosensitivity of metastases, peculiarly those of colorectal origin has forced many researchers to use methods for increasing the time and the concentration of drugs. The need for decreasing or limiting the side effects for this important and delicate organ led to the development of the technique of liver isolation for perfusion of antineoplastic agents. (K. R. Aigner, Isolated liver perfusion. In: Morris D L, McArdle C S, Onik G M, eds. Hepatic Metastases. Oxford: Butterworth Heinemann, 1996. 101-107). Since 1981, modifications and technical improvements have been continuously introduced. Liver metastases may be of different origin and their chemosensitivity may vary according to the histological type and their response in presence of heat.

The terms cancer, breast cancer, lung cancer, head and neck cancer, prostate cancer, brain cancer, colorectal cancer, liver cancer and malignant melanoma are known and understood in the art.

Prostate cancer is a form of cancer that develops in the prostate, a gland in the male reproductive system. Most prostate cancers are slow growing; however, there are cases of aggressive prostate cancers. The cancer cells may metastasize from the prostate to other parts of the body, particularly the bones and lymph nodes. The term prostate cancer preferably includes non-metastatic or metastatic prostate cancer. Even more preferably, the term prostate cancer includes androgen independent prostate cancer (AIPCa), androgen dependent prostate cancer (ADPCa), metastatic metastatic androgen independent prostate cancer and/or metastatic androgen dependent prostate cancer.

Colorectal cancer, less formally known as bowel cancer, is a cancer characterized by neoplasia in the colon, rectum, or vermiform appendix.

Liver cancer or hepatic cancer is properly considered to be a cancer which starts in the liver, as opposed to a cancer which originates in another organ and migrates to the liver, known as a liver metastasis. There are many forms of liver cancer, although many cancers found in the liver are metastases from other tumors, frequently of the GI tract (like colon cancer, carcinoid tumors mainly of the appendix, etc.), but also from breast cancer, ovarian cancer, lung cancer, renal cancer, prostate cancer, etc. The most frequent liver cancer is hepatocellular carcinoma (HCC). This tumor also has a variant type that consists of both HCC and cholangiocarcinoma components. The cells of the bile duct coexist next to the bile ducts that drain the bile produced by the hepatocytes of the liver. Cancers which arise from the blood vessel cells in the liver are known has hemangioendotheliomas.

Malignant melanoma is a malignant tumor of melanocytes. Melanocytes are cells that produce the dark pigment, melanin, which is responsible for the color of skin. They predominantly occur in skin, but are also found in other parts of the body, including the bowel and the eye (see uveal melanoma). Melanoma can occur in any part of the body that contains melanocytes. Melanoma is less common than other skin cancers. However, it is much more dangerous and causes the majority (75%) of deaths related to skin cancer. Worldwide, doctors diagnose about 160,000 new cases of melanoma yearly.

A preferred subject of the instant invention is a method of disorders as described herein, wherein the disorders are selected from cancer and/or metastatic cancer. Preferably, the metastatic cancer is selected from the group consisting of metastatic breast cancer, metastatic lung cancer, metastatic head and neck cancer, metastatic prostate cancer, metastatic colorectal cancer, metastatic liver cancer and metastatic malignant melanoma.

In the context of the instant invention the metastases are preferably qualified or named by the organ they metastasized to.

[34] According to the instant invention, the metastases are preferably selected from the group consisting of bone metastases, lung metastases, liver metastases and brain metastases, more preferably selected from group consisting of bone metastases, lung metastases and brain metastases and especially preferably selected from group consisting of bone metastases and brain metastases.

According to the invention, the metastases preferably include lymph node metastases, even more preferably distant lymph node metastases. Thus, a preferred subject of the instant invention relates to a method of treating disorders as described above and/or below and especially as described in one or more of the paragraphs [1] to [34] and/or the paragraphs relating thereto, wherein the disorder to be treated are lymph node metastases.

[35] According to the instant invention, the cancer is preferably selected from the group consisting of breast cancer, lung cancer, head and neck cancer, prostate cancer, brain cancer, colorectal cancer, liver cancer and malignant melanoma, more preferably selected from the group consisting of breast cancer, lung cancer, head and neck cancer, prostate cancer, brain cancer and colorectal cancer, even more preferably selected from the group consisting of breast cancer, lung cancer, head and neck cancer, prostate cancer and colorectal cancer and especially preferably is selected from the group consisting of breast cancer, lung cancer, head and neck cancer. Alternatively preferably, the cancer is selected from the group consisting of prostate cancer, colorectal cancer and liver cancer. Alternatively preferably, the cancer is selected from the group consisting of brain cancer, liver cancer and malignant melanoma.

The term "breast cancer" as used in the context of the present invention preferably includes:
hormone receptor negative breast cancer,
hormone receptor positive breast cancer,
HER2 negative breast cancer,
HER2 positive breast cancer,
hormone receptor negative, HER2 negative breast cancer,
hormone receptor positive, HER2 negative breast cancer,
hormone receptor negative, HER2 positive breast cancer, and/or
hormone receptor positive, HER2 positive breast cancer.

The term "breast cancer" as used in the context of the present invention preferably includes "normal" breast cancer" or "non-metastatic breast cancer", and/or "metastatic breast cancer".

The term "non-metastatic breast cancer" preferably includes:
non-metastatic hormone receptor negative breast cancer,
non-metastatic hormone receptor positive breast cancer,
non-metastatic HER2 negative breast cancer,
non-metastatic HER2 positive breast cancer,
non-metastatic hormone receptor negative, HER2 negative breast cancer,
non-metastatic hormone receptor positive, HER2 negative breast cancer,
non-metastatic hormone receptor negative, HER2 positive breast cancer, and/or
nonmetastatic hormone receptor positive, HER2 positive breast cancer.

The term "metastatic breast cancer" is preferably selected from:
metastatic hormone receptor negative breast cancer,
metastatic hormone receptor positive breast cancer,
metastatic HER2 negative breast cancer,
metastatic HER2 positive breast cancer,
metastatic hormone receptor negative, HER2 negative breast cancer,
metastatic hormone receptor positive, HER2 negative breast cancer,
metastatic hormone receptor negative, HER2 positive breast cancer, and/or
metastatic hormone receptor positive, HER2 positive breast cancer.

Those terms are known and understood in the art.

[36] Thus, a preferred subject of the instant invention relates to a method of treatment as described herein and especially as described in one or more of the paragraphs numbered [1] to [35] and/or the paragraphs relating thereto, wherein the disorders to be treated are one or more disorders, selected from the groups consisting of
i) bone, brain, lung and/or liver metastases of breast cancer,
ii) brain, bone, lung and/or liver metastases of lung cancer,
iii) brain metastases of malignant melanoma,
iv) bone and/or liver metastases of colorectal cancer,
v) bone metastases of prostate cancer, and
vi) lung, liver and/or bone metastases of head and neck cancer. More preferably, the disorders to be treated are one or more disorders, selected from the group consisting of brain metastases of lung cancer, brain metastases of malignant melanoma, brain metastases of breast cancer, bone metastases of breast cancer, bone metastases of prostate cancer, bone metastases of colorectal cancer and liver metastases of colorectal cancer. Even more preferably, the disorders to be treated are one or more disorders selected from the group consisting of bone metastases of breast cancer, bone metastases of colorectal cancer and/or bone metastasis of prostate cancer. Alternatively preferably, the disorders to be treated are selected from the group consisting of brain metastases, preferably brain metastases of breast cancer, brain metastases of lung cancer and/or brain metastases of malignant melanoma, and especially preferably brain metastases of lung cancer.

[37] Thus, a preferred subject of the instant invention relates to a method of treatment as described herein and especially as described in one or more of the paragraphs numbered [1] to [36] and/or the paragraphs relating thereto, wherein the lung cancer is selected from non-small cell carcinoma (NSCLC) and small cell carcinoma (NSCLC), the head and neck cancer is squamous cell carcinoma of the head and neck (SCCHN), the liver cancer is hepatocellular carcinoma (HCC) and/or the brain cancer is selected from astrocytoma, glioblastoma and glioblastoma multiforme.

Thus, a preferred subject of the instant invention relates to a method of treatment as described herein and especially as described in one or more of the paragraphs numbered [1] to [37] and/or the paragraphs relating thereto, wherein the disorder to be treated is selected from non-small cell carcinoma (NSCLC) and/or metastases thereof, and especially preferably selected from non-small cell carcinoma (NSCLC) and/or brain metastases thereof.

Thus, a preferred subject of the instant invention relates to a method of treatment as described herein and especially as described in one or more of the paragraphs numbered [1] to [37] and/or the paragraphs relating thereto, wherein the disorder to be treated is selected from brain metastases of non-small cell carcinoma (NSCLC).

Thus, a preferred subject of the instant invention relates to a method of treatment as described herein and especially as described in one or more of the paragraphs numbered [1] to [37] and/or the paragraphs relating thereto, wherein the disorder to be treated is selected from small cell carcinoma (SCLC) and/or metastases thereof, and especially preferably selected from small cell carcinoma (SCLC) and/or brain metastases thereof.

Thus, a preferred subject of the instant invention relates to a method of treatment as described herein and especially as described in one or more of the paragraphs numbered [1] to [37] and/or the paragraphs relating thereto, wherein the disorder to be treated is selected from brain metastases of small cell carcinoma (SCLC).

Thus, a preferred subject of the instant invention relates to a method of treatment as described herein and especially as described in one or more of the paragraphs numbered [1] to [37] and/or the paragraphs relating thereto, wherein the disorder to be treated is selected from squamous cell carcinoma of the head and neck (SCCHN) and/or metastases thereof, and especially preferably selected from squamous cell carcinoma of the head and neck (SCCHN) and/or metastases thereof in the lung, liver and/or bone.

Thus, a preferred subject of the instant invention relates to a method of treatment as described herein and especially as described in one or more of the paragraphs numbered [1] to

[37] and/or the paragraphs relating thereto, wherein the disorder to be treated is selected from lung, liver and/or bone metastases of squamous cell carcinoma of the head and neck (SCCHN).

Thus, a preferred subject of the instant invention relates to a method of treatment as described herein and especially as described in one or more of the paragraphs numbered [1] to [37] and/or the paragraphs relating thereto, wherein the disorder to be treated is selected from hepatocellular carcinoma (HCC) and/or metastases thereof, and especially preferably selected from hepatocellular carcinoma (HCC).

Thus, a preferred subject of the instant invention relates to a method of treatment as described herein and especially as described in one or more of the paragraphs numbered [1] to [37] and/or the paragraphs relating thereto, wherein the disorder to be treated is selected from colorectal cancer and/or metastases thereof, and especially preferably selected from colorectal cancer and/or liver or bone metastases thereof.

Thus, a preferred subject of the instant invention relates to a method of treatment as described herein and especially as described in one or more of the paragraphs numbered [1] to [37] and/or the paragraphs relating thereto, wherein the disorder to be treated is selected from liver metastases of colorectal cancer.

Thus, a preferred subject of the instant invention relates to a method of treatment as described herein and especially as described in one or more of the paragraphs numbered [1] to [37] and/or the paragraphs relating thereto, wherein the disorder to be treated is selected from malignant melanoma and/or metastases thereof, and especially preferably selected from malignant melanoma and/or brain metastases thereof.

Thus, a preferred subject of the instant invention relates to a method of treatment as described herein and especially as described in one or more of the paragraphs numbered [1] to [37] and/or the paragraphs relating thereto, wherein the disorder to be treated is selected from brain metastases of malignant melanoma.

Thus, a preferred subject of the instant invention relates to a method of treatment as described herein and especially as described in one or more of the paragraphs numbered [1] to [37] and/or the paragraphs relating thereto, wherein the disorder to be treated is selected from breast cancer and/or metastases thereof, and especially preferably selected from breast cancer and/or bone or brain metastases thereof.

Thus, a preferred subject of the instant invention relates to a method of treatment as described herein and especially as described in one or more of the paragraphs numbered [1] to [37] and/or the paragraphs relating thereto, wherein the disorder to be treated is selected from bone metastases of breast cancer.

Thus, a preferred subject of the instant invention relates to a method of treatment as described herein and especially as described in one or more of the paragraphs numbered [1] to [37] and/or the paragraphs relating thereto, wherein the disorder to be treated is selected from prostate cancer and/or metastases thereof, and especially preferably selected from prostate cancer and/or bone metastases thereof.

Thus, a preferred subject of the instant invention relates to a method of treatment as described herein and especially as described in one or more of the paragraphs numbered [1] to [37] and/or the paragraphs relating thereto, wherein the disorder to be treated is selected from bone metastases of prostate cancer.

Preferably, the method of treating disorders as described herein and preferably as described in one or more of the paragraphs numbered [1] to [37] and/or the paragraphs relating thereto, can be advantageously combined with radiotherapy. Even more preferably, the method of treating disorders, selected from cancer and/or metastases thereof as described herein and preferably as described in one or more of the paragraphs numbered 1] to [37] and/or the paragraphs relating thereto, can be advantageously combined with radiotherapy. Said methods can be even more preferably combined with concurrently or consecutively administered radiotherapy. Radiotherapy in this regard is preferably selected from radioimmunotherapy and external beam radiation, and more preferably is external beam radiation.

Thus, a preferred subject of the instant invention relates to a method of treating a subject as described herein and especially as described in one or more of the paragraphs numbered [1] to [37] and/or the paragraphs relating thereto, wherein said subject also receives or received, preferably receives radiotherapy, preferably radiotherapy as described herein.

Thus, even more preferred is a method of treating a subject as described herein and especially as described in one or more of the paragraphs numbered [1] to [37] and/or the paragraphs relating thereto, wherein said methods (additionally) comprises administering radiotherapy to said subject. Especially preferred is a method of treating a subject as described herein and especially as described in one or more of the paragraphs numbered [1] to [37] and/or the paragraphs relating thereto, wherein said methods (additionally) comprises administering radiotherapy concurrently or consecutively to said subject. Radiotherapy in this regard is preferably external beam radiation.

According to the instant invention, radiotherapy is preferably external beam radiation. The terms "radiotherapy" and "external beam radiation" in this regard are known and understood in the art. Preferably, external beam radiation includes, but is not limited to, single dose external beam radiation or single dose radiation, fractionated external beam radiation or fractionated radiation, focal radiation and whole organ irradiation, such as whole brain radiation. Radiation in this regard is preferably also referred to as irradiation.

Typically, the external beam radiation is photon radiation and/or gamma radiation.

The amount of radiation used in external beam radiation and/or photon radiation therapy is measured in gray (Gy), and varies depending on the type and stage of cancer being treated. For curative cases, the typical dose for a solid tumor ranges from 60 to 80 Gy. Preventative and/or adjuvant doses are typically around 45-60 Gy in 1.8-2 Gy fractions (e.g. for Breast, Head, and Neck cancers.) Suitable doses and dosing schedules are known to the skilled artisan.

In some embodiments, the treatment of the bone metastases comprises or induces
a) reduced bone resorption, preferably reduced osteoclast-mediated bone resorption,
b) new bone formation, preferably new bone formation in the osteolytic lesions,
c) regulation or normalisation of the osteoclast activity,
d) resumption of bone formation,
e) regrowth of bone or partial regrowth of the bone, in said subject.

The term "at least one" preferably comprises the terms "at least two" and/or "at least three", and preferably the like. The term "at least one" thus preferably includes "one", "two", "three" and preferably also higher numbers.

The term "one or more" preferably has the same meaning as "at least one", and thus preferably also includes the meanings "two or more" and/or "three or more", and preferably the like. The term "one or more" thus preferably also includes "one", "two", "three" and preferably also higher numbers.

If not explicitly stated otherwise, the term "solid composition" or "solid compositions" preferably exclusively refers to such compositions that are free of water or essentially free of water. Essentially free of water with regard to said solid compositions means a residual water content of less than 10%, more preferably less than 5%, even more preferably less than 2% and especially preferably less than 1%, e.g. 0.001 to 5% or 0.01 to 2%, preferably based on the total weight of the (dried) composition If not explicitly stated otherwise, the term "composition" or "compositions" in the absence of the term "solid" preferably refers to both
a) "non-solid compositions", i.e. compositions that preferably have a water content of more than 1%, more preferably a water content of more than 2%, even more preferably a water content of more than 5% and especially a water content of more than 10%, preferably based on the total weight of the respective composition, and
b) "solid compositions", preferably as defined above.

However, if not explicitly stated otherwise, the amounts given herein for the respective ingredients in the compositions in the absence of the term "solid" preferably refer to the amounts in "non-solid compositions", preferably water-based compositions as described herein, and even more preferably refer to suspensions and especially preferably aqueous suspensions as described herein.

Preferably, the compositions of the present invention are surprisingly stable to storage, preferably including both the chemical stability of the components and especially the chemical stability of the cyclic oligopeptide and/or the physical stability, preferably including the physical stability of the solid particles thereof. In particular, the solutions of the invention are generally stable to storage at ambient temperature (e.g. 25° C./60% rel. hum.) for a period of no less than 4 weeks (e.g. 4 weeks to 3 years), preferably no less than three months, more preferably no less than 6 months.

Chemical stability in this regard preferably refers to the absence of significant degradation of one or more of the contained components and especially refers to the absence of significant degradation of the contained cyclic oligopeptide(s).

Physical stability in this regard preferably refers to
a) the absence of significant precipitation, segregation and/or exsolution of originally dissolved components, and/or
b) the absence of significant changes in particle sizes, average particle size and/or particle size distribution of originally contained solid (particulate) components.

Physical stability in this regard more preferably refers to the absence of significant changes in particle sizes, average particle size and/or particle size distribution of originally contained solid particles of the cyclic oligopeptide(s).

Physical stability in this regard even more preferably refers to the absence of significant "Ostwald ripening" of the contained solid particles of the cyclic oligopeptide(s).

Said chemical and/or physical stability of the compositions described herein is preferably found even on prolonged storage at typical storage conditions for pharmaceutical products.

Typical storage conditions for pharmaceutical products are preferably selected from storage at 2-8° C. and storage at 25° C./60% relative humidity. For liquid pharmaceutical products, storage at 2-8° C. is especially preferred.

Preferably, the compositions according to the invention show an at least suitable or preferably good syringeability.

Preferably, the particle size in the composition and/or the viscosity of the composition enables convenient administration to a patient using syringes or other devices for injection equipped with up to 23 gauge needless, up to 24 gauge needles, up to 25 gauge needles, up to 26 gauge needles, up to 27 gauge needles or up to 28 gauge needles.

Preferably, the compositions according to the invention show both a fast onset and a sustained release characteristic for the contained cyclic oligopeptide(s). The term "fast onset" is known and understood in the art. Fast onset in this regard more preferably means that generally 3 to 15% and preferably 5 to 15% of the cyclic oligopeptide(s) contained in said compositions is released within the first 1 to 5 hours and more preferably the first 1 to 3 hours after injection, preferably subcutaneous injection, into the patient or subject. The term "sustained-release" is known and understood in the art. Sustained release in this regard more preferably means that generally 85 to 95% of the cyclic oligopeptide(s) contained in said compositions is released over a period of 8 hours or more, preferably 16 hours or more, even more preferably 24 hours or more, even more preferably 36 hours or more, even more preferably 48 hours or more and especially preferably 72 hours or more after injection, preferably subcutaneous injection, into the patient or subject.

Preferably, the compositions according to the invention show, after administration to a patient or subject, preferably after subcutaneous administration to a patient or subject, an about linear release characteristics over one or more prolonged time periods. A prolonged time period in this regard preferably means 8 or more hours, preferably 16 or more hours, more preferably 32 hours or more and especially 48 hours or more. Thus, if administered to a patient or subject, the compositions according to the invention preferably show at least one prolonged time period, preferably at least one prolonged time period in the range between 8 to 48 hours and especially in the range of 16 to 32 hours, wherein the contained cyclic oligopeptide(s) is released from said composition in an about linear release characteristic and/or concentration. Thus, if administered to a patient or subject, the compositions according to the invention preferably show an about linear pharmacokinetic profile for the contained cyclic oligopeptide(s) over at least one prolonged time period as described above, preferably based on the plasma level of said cyclic oligopeptide(s) in said patient or subject.

Preferably, the compositions according to the invention are free or essentially free of water insoluble compounds. Preferably, the compositions according to the invention are free or essentially free of water insoluble pharmaceutically active ingredients. Preferably, the compositions according to the invention are free or essentially free of water insoluble oligopeptides or cyclic oligopeptides. Water insoluble in this regard preferably means that the compounds and/or pharmaceutically active ingredients have a solubility in water that is 0.1 mg/ml or less, more preferably 1 mg/ml or less and especially 5 mg/ml or less. Preferably, the water solubility in this regard can be determined as it is known in the art or as is described herein. More preferably, the water solubility in this regard is determined at physiological pH (6.5-7.4), preferably according to methods known in the art or according to methods as described herein.

Preferably, the compositions according to the invention do not contain one or more antigens. More preferably, the compositions according to the invention are free or essentially free of antigens or compounds that act as antigens.

Preferably, the composition according to the invention provides a dosageform, especially a dosageform for injection and more preferably subcutaneous injection that enables a high drug load or high concentration of API based on the total composition. For example the concentration of the contained oligopeptide drug or API can preferably be 20% or more, more preferably 30% or more and especially 40% or more, based on the total composition. Percentages in this regard are preferably % v/v, % w/v or % w/w. Preferably, the compositions according to the invention with high concentrations nevertheless show an at least suitable or preferably good syringeability.

Preferably, the oligopeptide(s) contained in the compositions according to the invention do not act as an antigen.

Preferably, the compositions according to the invention do not contain one or more anticonvulsant agent. More preferably, the compositions according to the invention are free or essentially free of antigens or compounds that act as an anticonvulsant agent.

Preferably, the oligopeptide(s) contained in the compositions according to the invention do not act as an anticonvulsant agent.

Preferably, the compositions according to the invention do not contain one or more anti-retroviral agents. More preferably, the compositions according to the invention are free or essentially free of anti-retroviral agents or compounds that act as an anti-retroviral agent.

Preferably, the compositions according to the invention contain one or more lipophilic and/or amphiphilic compounds as described herein.

More preferably, the compositions according to the invention contain either
a) one or more lipophilic compounds as described herein, or
b) one or more amphiphilic compounds as described herein.

Even more preferably, the compositions according to the invention contain one or more amphiphilic compounds as described herein, but contain only minor amounts of lipophilic compounds as described herein, or are free or essentially free of lipophilic compounds as described herein. Minor amounts in this regard are 10% or less, 5% or less, 1% or less, 0.1% or less, or 0.01% or less, based on the amount of the one or more amphiphilic compounds as described herein contained in said composition. Percentages in this regard are preferably mole-% or % w/w, more preferably % w/w.

Preferably, the one or more amphiphilic compounds as described herein are selected from
a) anionic amphiphilic compounds as described herein,
b) non-ionic amphiphilic compounds as described herein,
c) cationic amphiphilic compounds as described herein, and/or
d) amphoteric or zwitterionic amphiphilic compounds as described herein.

Preferably, the one or more amphiphilic compounds as described herein are selected from
a) anionic amphiphilic compounds as described herein, and/or
b) non-ionic amphiphilic compounds as described herein.

Thus, the compositions according to the invention that contain one or more anionic amphiphilic compounds as described herein preferably contain only minor amounts of or are free or essentially free of non-ionic amphiphilic compounds, cationic amphiphilic compounds and amphoteric (or zwitterionic) amphiphilic compounds. Minor amounts in this regard are 10% or less, 5% or less, 1% or less, 0.1% or less, or 0.01% or less, based on the amount of the one or more anionic amphiphilic compounds as described herein contained in said composition. Percentages in this regard are preferably mole-% or % w/w, more preferably % w/w.

Preferably, the one or more amphiphilic compounds as described herein are exclusively selected from anionic amphiphilic compounds as described herein.

Generally, it is preferred to have a small number of different components in the compositions that are suitable for use as pharmaceutical compositions, e.g. to avoid unwanted chemical or physical interactions between the different compounds in that compositions, but also to avoid unwanted physiological or toxicological into action in the patient or subject that the composition is applied or administered to. Furthermore, pharmaceutical compositions containing an as little as number of components as possible have a lower risk of unwanted adverse effects and thus are also preferred from regulatory point of view with regard to the approval by the health authorities.

Thus, the compositions according to the invention preferably contain only one amphiphilic compound as described herein, preferably one anionic amphiphilic compounds as described herein. Preferably they contain only minor amounts of or are especially preferably free or essentially free of further amphiphilic compounds, preferably amphiphilic compounds as described herein. Thus, they preferably contain no second or third amphiphilic compound, especially no second or third amphiphilic compounds selected from non-ionic amphiphilic compounds, cationic amphiphilic compounds and amphoteric (or zwitterionic) amphiphilic compounds. Minor amounts in this regard are 10% or less, 5% or less, 1% or less, 0.1% or less, or 0.01% or less, based on the amount of the one anionic amphiphilic compound as described herein contained in said composition. Percentages in this regard are preferably mole-% or % w/w, more preferably % w/w.

Preferably, the amphiphilic compounds for use in the compositions according to the invention are selected from natural amphiphilic compounds and naturally derived amphiphilic compounds, preferably purified naturally derived amphiphilic compounds, and synthetic amphiphilic compounds, more preferably synthetically derived amphiphilic compounds. Especially preferred for use in the compositions according to the invention are synthetic amphiphilic compounds and/or synthetically derived amphiphilic compounds.

Thus, the compositions according to the invention preferably contain only minor amounts of or are especially preferably free or essentially free of natural amphiphilic compounds and/or naturally derived amphiphilic compounds. Such natural amphiphilic compounds or naturally derived amphiphilic compounds include, but are preferably not limited to natural cholines, such as egg phosphatidylcholine, soy phosphatidylcholine, lecthine and the like. Minor amounts in this regard are preferably 0.5% or less, 0.1% or less, 0.01% or less, 0.001% or less, or 0.0001% or less, based on the amount of the one or more oligopeptides or cyclic oligopeptides as described herein contained in said composition. Percentages in this regard are preferably mole-% or % w/w, more preferably % w/w.

The term "ad. 100%", "add 100%" and/or "add. 100%" with respect to a component of a composition is known in the art. Preferably, it means that this component is added to the other given components until 100% of the composition or total composition is achieved. Accordingly, the term "ad. 100 v %" preferably means that this component is added to the other given components until 100 v % of the composition or total composition is achieved, and the like.

A preferred subject of the instant invention is a method or a use as described herein, wherein the medicament is to be used in the treatment of recurrent cancer, for example in a second line or subsequent treatment setting.

A more preferred subject of the instant invention is a method or a use as described herein, wherein the medicament is to be used in the treatment of recurrent cancer, for example in a second line or subsequent treatment setting, wherein the cancer is as defined herein.

A method or a use according to one of the preceding claims, wherein the medicament is to be used in the treatment of newly diagnosed cancer, preferably in a first line chemotherapy setting.

Anther preferred subject of the instant invention is a method or a use as described herein, wherein the medicament is to be used in the treatment of newly diagnosed cancer, preferably in a first line treatment setting, wherein the cancer is selected from the group consisting of astrocytoma, more preferably astrocytoma grade II, III and/or IV, and especially consisting of glioblastoma or glioblastoma multiforme.

A further subject of the instant invention is a method of treatment of a subject, preferably a human subject, or a use as described herein regarding the Peptide according to formula cyclo-(Arg-Gly-Asp-DPhe-NMeVal) and/or the pharmaceutically acceptable salts thereof, preferably cyclo-(Arg-Gly-Asp-DPhe-NMeVal), wherein the treatment or use concerns newly diagnosed cancer, preferably in a first line chemotherapy setting.

Preferably, a reference to "the Peptide of the formula Cyclo-(Arg-Gly-Asp-DPhe-NMe-Val)" or the reference to "Cyclo-(Arg-Gly-Asp-DPhe-NMe-Val)" includes also the pharmaceutically acceptable derivatives, solvates and/or salts thereof.

Preferably, a reference to "the Peptide" or "said Peptide" preferably means "the Peptide of the formula Cyclo-(Arg-Gly-Asp-DPhe-NMe-Val)" and preferably also includes the pharmaceutically acceptable derivatives, solvates and/or salts thereof.

Thus, a reference to "the Peptide and/or the pharmaceutically acceptable derivatives, solvates and/or salts thereof" or to "said Peptide and/or the pharmaceutically acceptable derivatives, solvates and/or salts thereof" preferably refers to "the Peptide of the formula Cyclo-(Arg-Gly-Asp-DPhe-NMe-Val) and/or the pharmaceutically acceptable derivatives, solvates and/or salts thereof".

The term "without a pause" as used herein, especially used with respect to treatment regimens or treatment durations, is preferably understood to mean that said treatment regimens or durations are performed or applied in a consecutive order. For example, "2 to 8 weeks and especially 6 weeks, preferably without a pause" is preferably intended to mean "2 to 8 weeks and especially 6 weeks, preferably in a consecutive order".

If not specified otherwise, amounts administered to a patient given in "mg", such as in 500 mg, 1000 mg, 2000 mg, etc., are preferably intended to mean the respective amounts to be administered "flat", i.e. as a fixed dose that is not adjusted to the bodyweight and/or body surface of the respective patient.

Especially preferred according to the invention are subjects as described herein, wherein the characteristics of two or more preferred, more preferred and/or especially preferred embodiments, aspects and/or subjects are combined into one embodiment, aspect and/or subject. Preferably, according to this invention, preferred subjects or embodiments can be combined with other preferred subjects or embodiments; more preferred subjects or embodiments can be combined with other less preferred or even more preferred subjects or embodiments; especially preferred subjects or embodiments can be combined with other just preferred or just even more preferred subjects or embodiments, and the like.

Preferably, the reference to a paragraph numbered [9] preferably includes the reference to the paragraph numbered [9a] and/or the paragraph numbered [9b]. Preferably, the reference to a paragraph numbered [28] preferably includes the reference to the paragraph numbered [28a] and/or the paragraph numbered [28b]. Preferably, the reference to a paragraph numbered [29] preferably includes the reference to the paragraph numbered [29a] and/or the paragraph numbered [29b].

The term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of plus/minus 15% and especially of plus/minus 10%.

A method or a use according to one of the preceding claims, wherein the medicament is to be used in the treatment of newly diagnosed cancer, preferably in a first line chemotherapy setting.

Anther preferred subject of the instant invention is a method or a use as described herein, wherein the medicament is to be used in the treatment of newly diagnosed cancer, preferably in a first line treatment setting, wherein the cancer is selected from the group consisting of astrocytoma, more preferably astrocytoma grade II, III and/or IV, and especially consisting of glioblastoma or glioblastoma multiforme.

The term "without a pause" as used herein, especially used with respect to treatment regimens or treatment durations, is preferably understood to mean that said treatment regimens or durations are performed or applied in a consecutive order. For example, "2 to 8 weeks and especially 6 weeks, preferably without a pause" is preferably intended to mean "2 to 8 weeks and especially 6 weeks, preferably in a consecutive order".

As used herein, the term "about" with respect to numbers, amounts, dosings, hours, times, timings, durations, and the like, is preferably understood to mean "approximately" with respect to said numbers, amounts, dosings, hours, times, timings, durations, and the like.

Moreover, the following examples are given in order to assist the skilled artisan to better understand the present invention by way of exemplification. The examples are not intended to limit the scope of protection conferred by the claims. The features, properties and advantages exemplified for the compounds, compositions, methods and/or uses defined in the examples may be assigned to other compounds, compositions, methods and/or uses not specifically described and/or defined in the examples, but falling under the scope of what is defined in the claims.

Preferably, the features, properties and advantages exemplified for the compounds, compositions, methods and/or uses defined in the examples and/or claims may be assigned to other compounds, compositions, methods and/or uses not specifically described and/or defined in the examples and/or claims, but falling under the scope of what is defined in the specification and/or the claims.

The invention is explained in greater detail below by means of examples. The invention preferably can preferably be carried out throughout the range claimed and is not restricted to the examples given here.

EXPERIMENTAL SECTION

The following examples are given in order to assist the skilled artisan to better understand the present invention by way of exemplification. The examples are not intended to limit the scope of protection conferred by the claims. The features, properties and advantages exemplified for the compounds and uses defined in the examples and/or the Figures related thereto may be assigned to other compounds and uses not specifically described and/or defined in the examples and/or the Figures related thereto, but falling under the scope of what is defined in the claims.

Example 1

This Example of a typical composition in the form of a suspension comprising a lipophilic compound and preferably no water may contain per mL:
  150 to 300 mg/mL of solid Cilengitide, preferably in amorphous or crystalline form, more preferably the crystalline form A1-Cilengitide
  optionally 9 mg/mL sodium chloride
  optionally 5 mg/mL phenol
  Sesame oil (add 100%)

The composition of Example 1 is preferably prepared by suspending the solid Cilengitide and especially the solid A1-Cilengitide in the oil by adding it to the oil under stirring. Preferably, the stirring is continued for 4 to 20 h. If desired, the sodium chloride can then be added for adjusting the tonicity of decomposition and/or the phenol can be added for the preservation of the composition. If necessary, further amounts of the oil can be added (add 100%) to achieve the total volume of the composition i.e. 1 mL.

Example 2

This Example of a typical composition in the form of a suspension comprising a lipophilic compound and preferably no water may contain per mL:
  200 mg/mL of Cilengitide in the crystalline form A1
  optionally 9 mg/mL sodium chloride
  optionally 5 mg/mL phenol
  Miglyol 812 (add 100%)

The composition of Example 2 is preferably prepared by suspending the solid Cilengitide in the crystalline form A1 in the oil (Miglyol 812) by adding it to the oil under stirring. Preferably, the stirring is continued for 4 to 48 h. If desired, the sodium chloride can then be added for adjusting the tonicity of decomposition and/or the phenol can be added for the preservation of the composition. If necessary, further amounts of the oil can be added (add 100%) to achieve the total volume of the composition i.e. 1 mL.

Example 3

This Example of a typical composition (5 mL) in the form of a suspension comprising a lipophilic compound and preferably no water may contain per mL:
  200 mg/mL of micronized A1-Cilengitide, e.g. micronized A1-Cilengitide with a typical particle size distribution of d(10)=1-5 µm, d(50)=5-10 µm, and d(90)=20-30 µm,
  optionally 9 mg/mL sodium chloride
  optionally 5 mg/mL phenol
  sesame oil (add 100%)

The composition of Example 3 is preferably prepared by suspending the solid micronized A1-Cilengitide (1000 mg) in an aliquot of the sesame oil (3 mL) by adding it to the oil under stirring. Preferably, the stirring is continued for 4 to 48 h. If desired, the sodium chloride can then be added for adjusting the tonicity of decomposition and/or the phenol can be added for the preservation of the composition. If necessary, further amounts of the oil can be added (add 100%) to achieve the total volume of the composition i.e. 5 mL.

Example 4

This Example of a typical composition (5 mL) in the form of a suspension comprising an amphiphilic compound and water may contain per mL:
  200 mg/mL of micronized A1-Cilengitide, e.g. micronized A1-Cilengitide with a typical particle size distribution of d(10)=1-5 µm, d(50)=5-10 µm, and d(90)=20-30 µm,
  1 to 20 mg/mL DOPG
  optionally 9 mg/mL sodium chloride
  optionally 5 mg/mL phenol
  water for injection (add 100%)

The composition of Example 4 is preferably prepared by solubilization of the DOPG in water, preferably water for injection, at about room temperature or preferably at slightly elevated temperature, e.g. at about at about 30° C. or at about 40° C. After the solubilization, the micronized A1-Cilengitide (1000 mg) is added subsequently under stirring. Preferably, the stirring is continued for 4 to 20 h. If desired, the sodium chloride can then be added for adjusting the tonicity of decomposition and/or the phenol can be added for the preservation of the composition. If necessary, further amounts of water can be added (add 100%) to achieve the total volume of the composition, i.e. 5 mL.

Example 5

This Example of a typical suspension may contain per mL:
  200 to 300 mg/mL of micronized A1-Cilengitide, e.g. micronized A1-Cilengitide with a typical particle size distribution of d(10)=1-5 µm, d(50)=5-10 µm, and d(90)=20-30 µm, or micronized A1-Cilengitide with an even more narrow particle size distribution optionally
  1 to 20 mg/mL DOPG
  optionally 9 mg/mL sodium chloride
  optionally 5 mg/mL phenol
  water for injection (add 100%)

The composition of Example 2 is preferably prepared by solubilization of DOPG in water, preferably water for injection, at about room temperature or preferably at slightly elevated temperature, e.g. at about 30° C. or at about 40° C. After the solubilization, the solid A1-Cilengitide is added subsequently under stirring. Preferably, the stirring is continued for 2 to 6 h. If desired, the sodium chloride can then be added for adjusting the tonicity of the composition and/or the phenol can be added for the preservation of the composition. Then water is added (add 100%) i.e. until the total volume of 1 mL of the composition is obtained

Example 6

A preferred method of manufacture comprises the following steps, preferably in the given order:
1. Dissolution or solubilisation of solid DOPG in water under stirring at a temperature between 20° C. and 40° C.
2. Addition of solid Cilengitide, preferably crystalline Cilengitide, more preferably crystalline Cilengitide anhydrate and especially crystalline Cilengitide of the form A1
3. Stirring of the obtained suspension until a stable particle distribution is obtained, generally 24 h or more and especially 24 to 48 h
4. Addition of NaCl, generally about 9 mg/mL, to the suspension under continued stirring, and optionally
5. Continuation of the stirring process (in order to prevent sedimentation of the Cilengitide) until the suspension is filled in the respective container, vial or the like.

Example 7

A preferred alternate method of manufacture comprises the following steps, preferably in the given order:
1. Dissolution of solid DOPG in water under stirring at a temperature between 20° C. and 40° C.
2. Addition of NaCl, generally about 9 mg/mL, to the suspension under continued stirring
3. Addition of solid Cilengitide, preferably crystalline Cilengitide, more preferably crystalline Cilengitide anhydrate and especially crystalline Cilengitide of the form A1
4. Stirring of the obtained suspension until a stable particle distribution is obtained, generally 24 h or more and especially 24 to 48 h, and optionally
5. Continuation of the stirring process (in order to prevent sedimentation of the Cilengitide) until the suspension is filled in the respective container, vial or the like

Example 8

An especially preferred method of manufacture comprises the following steps, preferably in the given order:
1. Dissolution of solid DOPG in water under stirring at a temperature between 20° C. and 40° C.
2. Addition of micronised Cilengitide, preferably micronised Cilengitide anhydrate and especially micronised Cilengitide of the form A1
3. Stirring of the obtained suspension until a stable particle distribution is obtained, generally 4 h or more and especially 6 to 12 h
4. Addition of NaCl, generally about 9 mg/mL, to the suspension under continued stirring, and optionally
5. Continuation of the stirring process (in order to prevent sedimentation of the Cilengitide) until the suspension is filled in the respective container, vial or the like.

Example 9

An especially preferred alternate method of manufacture comprises the following steps, preferably in the given order:
1. Dissolution of solid DOPG in water under stirring at a temperature between 20° C. and 40° C.
2. Addition of NaCl, generally about 9 mg/mL, to the suspension under continued stirring
3. Addition of micronised Cilengitide, preferably micronised Cilengitide anhydrate and especially micronised Cilengitide of the form A1
4. Stirring of the obtained suspension until a stable particle distribution is obtained, generally 4 h or more and especially 6 to 12 h, and optionally
5. Continuation of the stirring process (in order to prevent sedimentation of the Cilengitide) until the suspension is filled in the respective container, vial or the like

Example 10

This Example of a typical composition (5 mL) in the form of a suspension comprising an amphiphilic compound and water may contain per mL:

200 mg/mL of micronized A1-Cilengitide, e.g. micronized A1-Cilengitide with a typical particle size distribution of d(10)=1-5 μm, d(50)=5-10 μm, and d(90)=20-30 μm, 1 to 20 mg/mL DMPG optionally 9 mg/mL sodium chloride optionally 5 mg/mL phenol water for injection (add 100%)

The composition of Example 4 is preferably prepared by solubilization of the DMPG in water, preferably water for injection, at about room temperature or preferably at slightly elevated temperature, e.g. at about at about 30° C. or at about 40° C. After the solubilization, the micronized A1-Cilengitide (1000 mg) is added subsequently under stirring. Preferably, the stirring is continued for 4 to 20 h. If desired, the sodium chloride can then be added for adjusting the tonicity of decomposition and/or the phenol can be added for the preservation of the composition. If necessary, further amounts of water can be added (add 100%) to achieve the total volume of the composition, i.e. 5 mL.

Example 11

This Example of a typical suspension may contain per mL:

200 to 300 mg/mL of micronized A1-Cilengitide, e.g. micronized A1-Cilengitide with a typical particle size distribution of d(10)=1-5 μm, d(50)=5-10 μm, and d(90)=20-30 μm, or micronized A1-Cilengitide with an even more narrow particle size distribution optionally 1 to 20 mg/mL DMPG optionally 9 mg/mL sodium chloride optionally 5 mg/mL phenol water for injection (add 100%)

The composition of Example 2 is preferably prepared by solubilization of DMPG in water, preferably water for injection, at about room temperature or preferably at slightly elevated temperature, e.g. at about 30° C. or at about 40° C. After the solubilization, the solid A1-Cilengitide is added subsequently under stirring. Preferably, the stirring is continued for 2 to 6 h. If desired, the sodium chloride can then be added for adjusting the tonicity of the composition and/or the phenol can be added for the preservation of the composition. Then water is added (add 100%) i.e. until the total volume of 1 mL of the composition is obtained Example 12

A preferred method of manufacture comprises the following steps, preferably in the given order:
1. Dissolution or solubilisation of solid DMPG in water under stirring at a temperature between 20° C. and 40° C.
2. Addition of solid Cilengitide, preferably crystalline Cilengitide, more preferably crystalline Cilengitide anhydrate and especially crystalline Cilengitide of the form A1
3. Stirring of the obtained suspension until a stable particle distribution is obtained, generally 24 h or more and especially 24 to 48 h
4. Addition of NaCl, generally about 9 mg/mL, to the suspension under continued stirring, and optionally
5. Continuation of the stirring process (in order to prevent sedimentation of the Cilengitide) until the suspension is filled in the respective container, vial or the like.

Example 13

A preferred alternate method of manufacture comprises the following steps, preferably in the given order:
1. Dissolution of solid DMPG in water under stirring at a temperature between 20° C. and 40° C.
2. Addition of NaCl, generally about 9 mg/mL, to the suspension under continued stirring
3. Addition of solid Cilengitide, preferably crystalline Cilengitide, more preferably crystalline Cilengitide anhydrate and especially crystalline Cilengitide of the form A1
4. Stirring of the obtained suspension until a stable particle distribution is obtained, generally 24 h or more and especially 24 to 48 h, and optionally
5. Continuation of the stirring process (in order to prevent sedimentation of the Cilengitide) until the suspension is filled in the respective container, vial or the like Example 14

An especially preferred method of manufacture comprises the following steps, preferably in the given order:
1. Dissolution of solid DMPG in water under stirring at a temperature between 20° C. and 40° C.
2. Addition of micronised Cilengitide, preferably micronised Cilengitide anhydrate and especially micronised Cilengitide of the form A1
3. Stirring of the obtained suspension until a stable particle distribution is obtained, generally 4 h or more and especially 6 to 12 h
4. Addition of NaCl, generally about 9 mg/mL, to the suspension under continued stirring, and optionally
5. Continuation of the stirring process (in order to prevent sedimentation of the Cilengitide) until the suspension is filled in the respective container, vial or the like.

Example 15

An especially preferred alternate method of manufacture comprises the following steps, preferably in the given order:
1. Dissolution of solid DMPG in water under stirring at a temperature between 20° C. and 40° C.
2. Addition of NaCl, generally about 9 mg/mL, to the suspension under continued stirring
3. Addition of micronised Cilengitide, preferably micronised Cilengitide anhydrate and especially micronised Cilengitide of the form A1
4. Stirring of the obtained suspension until a stable particle distribution is obtained, generally 4 h or more and especially 6 to 12 h, and optionally
5. Continuation of the stirring process (in order to prevent sedimentation of the Cilengitide) until the suspension is filled in the respective container, vial or the like Example 16

Pharmacokinetic Study in Mice
A composition/formulation composed of
200 micronized A1-Cilengitide with a typical particle size distribution of d(10)=1-5 µm, d(50)=5-10 µm, and d(90)=20-30 µm
1 mg/mL DOPG
9 mg/mL sodium chloride
water for injection,
was administered subcutaneously in a pharmacokinetic study in mice (Group A) versus two control groups (Groups B and C):
Group A (squares/sc-DOPG-50 mg/kg): A1-DOPG-Cilengitide suspension (200 mg/mL A1-Cilengitide, 1 mg/mL DOPG, 9 mg/mL DOPG in water for injection) by SC administration at a dose of 50 mg/KG.
Group B (tilted squares/iv-NaCl-5 mg/kg): Cilengitide infusion solution (8 mg/mL S3-Cilengitide in isotonic sodium chloride solution) by IV administration at a dose 5 mg/KG
Group C (triangles/sc-NaCl-10 mg/kg): Cilengitide infusion solution (8 mg/mL S3-Cilengitide in isotonic sodium chloride solution) by SC administration at a dose 10 mg/KG

| Route | Dose (mg/kg) | Data | 0.1 h | 0.25 h | 0.5 h | 1 h | 2 h | 3 h | 4 h | 6 h | 8 h |
|---|---|---|---|---|---|---|---|---|---|---|---|
| iv | 5 | Cilengitide IV solution (8 mg/mL in 0.9% NaCl) | | | | | | | | | |
| | | Average of EMD 121974 (ng/mL) | 2613.3 | 1370.0 | 1155.3 | 861.3 | 131.7 | — | 10.2 | — | — |
| | | StdDev of EMD 121974 (ng/mL) | 1610.7 | 295.1 | 785.5 | 672.2 | 103.6 | — | 6.1 | — | — |
| | | Sample size n | 3 | 3 | 3 | 3 | 3 | — | 3 | — | — |
| sc | 10 | Cilengitide IV solution (8 mg/mL in 0.9% NaCl) | | | | | | | | | |
| | | Average of EMD 121974 (ng/mL) | 7540.0 | 8200.0 | 3720.0 | 496.0 | 56.1 | 5.6 | — | — | — |
| | | StdDev of EMD 121974 (ng/mL) | 1131.4 | 933.4 | 594.0 | 22.6 | 2.8 | 0.3 | — | — | — |
| | | Sample size n | 2 | 2 | 2 | 2 | 2 | 2 | — | — | — |

-continued

| Route | Dose (mg/kg) | Data | 0.1 h | 0.25 h | 0.5 h | 1 h | 2 h | 3 h | 4 h | 6 h | 8 h |
|---|---|---|---|---|---|---|---|---|---|---|---|
| sc | 50 | Cilengitide A1-DOPG suspension (200 mg/mL) | | | | | | | | | |
| | | Average of EMD 121974 (ng/mL) | 2673.3 | 3790.0 | 4853.3 | 3966.7 | 2600.0 | — | 1640.0 | 1079.3 | 928.0 |
| | | StdDev of EMD 121974 (ng/mL) | 207.4 | 466.7 | 1397.9 | 556.4 | 254.6 | — | 481.2 | 351.1 | 158.4 |
| | | Sample size n | 3 | 2 | 3 | 3 | 2 | — | 3 | 3 | 2 |

Group A on A1-DOPG-Cilengitide suspension shows close to complete (>98%) bioavailability with a sustained-release profile compared to I.V. infusion of an isotonic Cilengitide solution (8 mg/mL). The observed t(max) of A1-DOPG suspension is comparable to the isotonic Cilengitide solution (8 mg/mL), as both formulations contain readily dissolved drug which is instantly available for absorption, also resulting into comparable c(max) values. A1-DOPG-Cilengitide suspension truly provides a controlled-/sustained drug release resulting in in-vivo drug concentrations above 1000 ng/mL up over 8 hours as a pronounced advantage over any isotonic Cilengitide solution (8 mg/mL) intended for I.V. infusion.

Furthermore, A1-DOPG suspensions were tested in in-vitro $\alpha_v\beta_{3/5}$ receptor assays showing that the specific activity of the Cilengitide in these suspensions is maintained.

Example 17

Pharmacokinetic study in Monkeys
Composition (Suspension) administered
 Cilengitide: 300 mg/mL
 DMPG: 2 mg/mL
 Phenol: 0.5%
 NaCl: 0.9%
Species/strain and number of animals
 Monkey, Cynomolgus
Dose: 12 mg/kg (40 μL suspension/kg)
Sampling time points: 0.25, 0.5, 2, 4, 8 hours post dose:

| Animal_No | Dose (mg/kg) | 0.250 | 0.500 | 2.00 | 4.00 | 8.00 |
|---|---|---|---|---|---|---|
| | | \multicolumn{5}{c}{MSC1097999 (ng/mL)} | | | | |
| 583 | 11.8 | 586 | 967 | 892 | 605 | 537 |

Example 18

Dosage Forms (Compositions) for Preclinical or Clinical Purposes

The final product is a sterile suspension intended for subcutaneous infusion. It is presented in the following concentrations: 100 mg/mL, 150 mg/ml and 300 mg/ml, preferably in a vial with a nominal volume of 1 ml, 2 ml or 5 ml.

Compositions
Composition of Cilengitide Drug Product 100 mg/ml, e.g. for Animal Toxicology, Preclinical Animal Models and/or Clinical Use

| Component | Amount (mg/mL) | Function |
|---|---|---|
| Cilengitide | 100 mg/mL | Active ingredient |
| DMPG | 2 mg/mL | stabilizier |
| Sodium chloride | 9 mg/mL | Isotonicity agent |
| Phenol | 5 mg/mL | preservative |
| Water for injection | Ad 1 mL | Diluent |

Composition of Cilengitide Drug Product 300 mg/ml, e.g. for Animal Toxicology, Preclinical Animal Models and/or Clinical Use

| Component | Amount (mg/mL) | Function |
|---|---|---|
| Cilengitide | 300 mg/mL | Active ingredient |
| DMPG | 2 mg/mL | stabilizier |
| Sodium chloride | 9 mg/mL | Isotonicity agent |
| Phenol | 5 mg/mL | preservative |
| Water for injection | Ad 1 mL | Diluent |

Alternative Composition of Cilengitide Drug Product 150 mg/ml, e.g. for Animal Toxicology, Preclinical Animal Models and/or Clinical Use

| Component | Amount (mg/mL) | Function |
|---|---|---|
| Cilengitide | 150 mg/mL | Active ingredient |
| DMPG | 1 mg/mL | stabilizier |
| Sodium chloride | 9 mg/mL | Isotonicity agent |
| Phenol | 5 mg/mL | preservative |
| Water for injection | Ad 1 mL | Diluent |

Alternative Composition of Cilengitide Drug Product 300 mg/ml, e.g. for Animal Toxicology, Preclinical Animal Models and/or Clinical Use

| Component | Amount (mg/mL) | Function |
|---|---|---|
| Cilengitide | 300 mg/mL | Active ingredient |
| DMPG | 1 mg/mL | stabilizier |
| Sodium chloride | 9 mg/mL | Isotonicity agent |
| Phenol | 5 mg/mL | preservative |
| Water for injection | Ad 1 mL* | Diluent |

Example 19

Ilengitide Inhibits Progression of Experimental Breast Cancer Bone Metastases as Imaged Non-Invasively Using VCT, MRI and DCE-MRI in a Longitudinal In Vivo Study The aim of this study is to investigate the effect of inhibiting $\alpha v\beta 3/\alpha v\beta 5$ integrins by cilengitide in experimentally induced breast cancer bone metastases using non-invasive imaging techniques. For this purpose, nude rats bearing established breast cancer bone metastases are treated with cilengitide, a small molecule inhibitor of αvβ3 and αvβ5 integrins (75 mg/kg, five days per week; n=12 rats) and compared to vehicle treated control rats (n=12). In a longitudinal study, conventional magnetic resonance imaging (MRI) and flat panel volumetric computed tomography (VCT) are used to assess the volume of the soft tissue tumor and osteolysis, respectively, and dynamic contrastenhanced (DCE–) MRI is performed to determine functional parameters of the tumor vasculature reflecting blood volume and blood vessel permeability. In rats treated with cilengitide, VCT and MRI shows that osteolytic lesions and the respective bone metastatic soft tissue tumors progress more slowly than in vehicle treated controls. DCE-MRI indicates a decrease in blood volume and an increase in vessel permeability, and immunohistology reveals increased numbers of immature vessels in cilengitidetreated rats compared to vehicle controls. In conclusion, treatment of experimental breast cancer bone metastases with cilengitide results in pronounced anti-resorptive and antitumor effects, suggesting that the achieved αvβ3/αvβ5 inhibition is a promising therapeutic approach for the treatment of bone metastases.

1. Introduction

Bone metastases occur frequently in many human malignancies including breast, prostate, and lung carcinoma. The stimulation of osteoclasts by tumor cells proliferating within the bone marrow is a feature of the pathogenesis of bone metastases, and both the tumor and the bone microenvironment must be considered when strategies for therapy of bone metastases are developed.[1] Bisphosphonates are potent inhibitors of osteoclast function that have been used over the last decades to treat patients with bone metastases. However, they do not induce regression of bone metastases. This, together with the adverse effects associated with bisphosphonate therapy such as osteonecrosis of the jaw and renal toxicity, emphasize the urgent need for the development of novel therapies that can be applied alternatively and as combination partners to target bone metastases more effectively.

Integrins are a family of 24 transmembrane proteins that integrate extracellular and intracellular activities. Besides their role in promoting physical adhesion, integrin signaling can induce cell spreading, migration, survival, proliferation, and differentiation.[2] The αvβ3 integrin interacts with several extracellular matrix (ECM) proteins including vitronectin, fibronectin, osteopontin, bone sialoprotein (BSP) and fibrinogen.[3,4] It is strongly expressed on activated tumor endothelial cells while on resting endothelial cells in non-diseased tissues its expression is generally low.[5-7] In the pathogenesis of bone metastases, osteoclasts too express αvβ3 integrin, and selective αvβ3 inhibitors have been shown to inhibit osteoclast-mediated bone resorption in experimental prostate carcinoma bone metastases.[8] Furthermore, αvβ3 integrin over expression on tumor cells stimulated metastasis to bone in experimental models.[9,10] The closely related integrin αvβ5 is also a vitronectin receptor involved in breast cancer cell migration and invasion, but is less studied in the pathogenesis of bone metastasis, although it is over expressed by osteoclasts and a wide range of cancer cells.[11,12] Together with αvβ5, αvβ3 integrin recognizes the arginine-glycine-aspartic acid (RGD) peptide sequence of extracellular ligands.[13] Cilengitide (EMD 121974) is a cyclic pentapeptide containing the sequence RGDf(N-Me)V with high affinity for αvβ3 and αvβ5, which inhibits αvβ3/αvβ5-dependent cellular processes.[14-17] As cilengitide inhibits αvβ3 and αvβ5 integrin from human, bovine and rat origin, it can be appropriately used in both experimental and clinical studies.[15,16] In recent phase II trials for treatment of glioblastoma multiforme, cilengitide has shown promising results including indications of anti-tumor activity and a good safety profile.[13,19] Cilengitide has anti-angiogenic activity in model systems, correlating with its inhibition of attachment, migration, sprouting, differentiation, and in the induction of anoikis in those endothelial angiogenic cells whose adhesion and survival is dependent on αvβ3/αvβ5.[15,18,20] Nevertheless, targeting αv integrins for therapy remains contentious, and for some tumors growth is accelerated in mice lacking αvβ3 and αvβ5 while in others, tumor growth and angiogenesis is accelerated by cilengitide.[21,22] In this study, we have used non-invasive imaging techniques to examine the dynamics of metastatic lesion development under therapy with cilengitide. Computed tomography (CT) and magnetic resonance imaging (MRI) are currently used to determine the extent of the osteolysis and the respective soft tissue component of bone metastases. For in vivo imaging of angiogenesis in bone metastases, dynamic contrast-enhanced MRI (DCE-MRI) allows assessment of functional parameters associated with blood volume and vessel permeability in these skeletal lesions.[23] We recently introduced an in vivo model of experimental breast cancer bone metastasis in which angiogenesis, soft-tissue lesion size and extent of osteolysis can be monitored simultaneously and longitudinally by volumetric CT (VCT), morphologic MRI and DCE-MRI.[23,24] Here we use this model to noninvasively assess the treatment effects of cilengitide inhibiting αvβ3 and αvβ5 integrins in breast cancer bone metastases.

2. Materials and Methods 2.1 Cell Lines and Culture Conditions

The human estrogen-independent breast cancer cell line MDA-MB-231 is purchased from American Type Culture Collection. Cells are cultured routinely in RPMI-1640 (Invitrogen, Karlsruhe, Germany), supplemented with 10% FCS (Sigma, Taufkirchen, Germany). All cultures are kept under controlled conditions (humidified atmosphere, 5% $CO_2$, 37° C.) and passaged 2-3 times a week to keep them in logarithmic growth.

2.2 Flow Cytometry

The integrin expression profile of MDA-MB-231 human breast cancer cells is characterized using flow cytometry. Surface integrin staining on live cells is performed as described with minor modifications.[25] Briefly, cells are harvested, rinsed, suspended in PBS-BSA (containing divalent cations), and sequentially incubated with mouse anti-αvβ3 (LM609[26]) mouse anti-αvβ5 (P1F6[27]; Millipore, Schwalbach, Germany), or mouse anti-αv (17E6[25]) followed by staining with fluorescinated goat-anti-mouse IgG and propidium iodide (5 µg/ml). Incubations use 10 µg/ml primary antibody concentrations and are for 45 min on ice. Flow cytometry is performed on a FACScan instrument (Becton-Dickinson, Heidelberg, Germany), gating for viable cells, and collecting 10000 events per staining. The mean fluorescence intensity of the integrin staining is normalized using the staining intensity of the second layer reagent as background.

2.3 Animal Model and Therapy Application

Nude rats (RNU strain) are obtained from Harlan-Winkelmann GmbH (Borchen, Germany) at the age of six weeks and housed in a specific pathogen-free environment in a mini barrier system of the central animal facility. Animals are kept under controlled conditions (21±2° C. room temperature, 60% humidity, 12 h light-dark rhythm) and offered autoclaved food and water ad libitum. Sub-confluent MDAMB-231 cells are harvested using 0.05% Trypsin-EDTA (Gibco®; Invitrogen, Karlsruhe, Germany) counted on a Neubauer's chamber and resuspended in RPMI-1640 to a final concentration of $10^5$ cells in 200 µl. Rats are anesthetized using a mixture of nitrous oxide (1 l/min), oxygen (0.5 l/min) and isoflurane (1.5 vol. %). Arterial branches of the right hind leg are dissected and $10^5$ cells injected into the superficial epigastric artery as described previously.[28] Bone metastases established and are observed exclusively in the femur, tibia and fibula of the right hind leg. 30 days after cancer cell transplantation, rats (n=24) are randomly divided into two groups, one group receiving the cyclic RGD-peptide inhibitor of $\alpha v\beta 3/\alpha v\beta 5$ integrins (cilengitide, EMD 121974[14, 17, 29]; Merck, Darmstadt, Germany) intraperitoneally five times per week (75 mg/kg; n=12 rats) and the other, sham-treated group, serving as a control (n=12 rats). The observation period of all animals is 55 days and no rat in the study dies ahead of schedule.

2.4 In Vivo Imaging

After the inoculation of cancer cells each rat is imaged at days 30, 35, 45 and 55 using (i) a flat-panel equipped volumetric computed tomograph (Volume CT, Siemens, Germany) and (ii) a 1.5T clinical magnetic resonance scanner (Symphony, Siemens, Erlangen, Germany) equipped with a home-built receive-transmit coil (cylindrical volume resonator with an inner diameter of 83 mm and a usable length of 120 mm). Prior to in vivo imaging with VCT and MRI, rats are anesthetized with nitrous oxide, oxygen and isoflurane as described above.

2.4.1 Volumetric Computed Tomography

VCT imaging is obtained using the following parameters: tube voltage 80 kV, tube current 50 mA, scan time 51 s, rotation speed 10 s, frames per second 120, matrix 512×512, and slice thickness 0.2 mm. Image reconstructions are performed using a modified FDK (Feldkamp Davis Kress) cone beam reconstruction algorithm (kernel H80a; Afra, Erlangen, Germany).

2.4.2 Magnetic Resonance Imaging

T2-weighted imaging is performed using a turbo spin echo sequence (orientation axial, TR 3240 ms, TE 81 ms, matrix 152×256, FOV 90×53.4 mm$^2$, slice thickness 1.5 mm, 3 averages, scan time 3 min 40 s). For dynamic contrast-enhanced MRI, a saturation recovery turbo flash sequence through the largest diameter of the tumor (orientation axial, TR 373 ms, TE 1.86 ms, matrix 192×144, FOV 130×97.5 mm, slice thickness 5 mm, measurements 512, averages 1, scan time 6 min 55 s) is used. After 20 s baseline, 0.1 mmol/kg Gd-DTPA (Magnevist; Bayer Schering Pharma, Berlin, Germany) is intravenously infused for a time period of 10 s.

2.5 Postprocessing

Unenhanced VCT images and MRI-acquired T2-weighted images are analyzed using the Medical Imaging Interaction Toolkit (MITK, Heidelberg, Germany) to determine volumes of osteolytic lesions and soft tissue components, respectively. DCE-MRI acquired data is analyzed using the Dynalab workstation (Mevis Research, Bremen, Germany) according to the two-compartment model of Brix to determine the parameters amplitude A and exchange rate constant kep, as described.[23, 30] Briefly, the injected contrast media is distributed in both compartments (intravascular space and extravascular, interstitial space). The accumulation of contrast agent in these compartments over time is characterized by the amplitude A (associated with blood volume), whereas the exchange of contrast agent between the intravascular space and the interstitial space is characterized by the exchange rate constant $k_{ep}$ (associated with vessel permeability). For determination of the respective values of the amplitude A and $k_{ep}$ of bone metastases in our study, a region of interest is placed around the soft tissue component on color maps for A and $k_{ep}$, respectively, using the Dynalab workstation (Mevis Research, Bremen, Germany).

2.6 Histology

At the end of the observation period lower limbs of each animal are amputated and muscular tissue removed. Bones with surrounding soft tissue tumors are stored in 70% ethanol and embedded in a methylmethacrylat-based compound (Technovit® 9100 NEU, Heraeus Kulzer, Hanau, Germany) according to the instructions of the manufacturer. 5 µm-thick sections are cut (Microm HM340e microtome; Thermo Scientific, Waltham, Mass.), mounted on Super-Frost Plus microscope slides and dried overnight at 60° C. Additional freshly removed soft tissue tumors are embedded in optimum cutting temperature compound (OCT, TissueTec, Sakura, Japan) and stored at −80° C. 7 µm thick cryosections (obtained on a Leica CM 3050S) are thaw-mounted, fixed in methanol and acetone and washed in PBS. For immunostaining, the Technovit®-embedded sections are incubated overnight at 4° C. with primary antibodies in PBS containing 12% bovine serum albumin. The following primary antibodies are used: rabbit anti-collagen IV polyclonal antibody (1:50; Progen Biotechnik GmbH, Heidelberg, Germany) and mouse anti-smooth muscle actin (SMA) polyclonal antibody (1:400; Sigma Aldrich, Saint Louis, Mo.). After washing in PBS, sections are incubated with secondary antibodies for 1 h at room temperature as follows: Texas Red® dye-conjugated donkey anti rabbit IgG (1:100; Jackson Immunoresearch, Suffolk, UK) and Cy™2-conjugated goat anti mouse IgG (1:50, Jackson Immunoresearch, Suffolk, UK). Cryosections are incubated overnight at 4° C. with the following antibodies: mouse anti-human integrin $\alpha v\beta 3$ Alexa Fluor® 488 conjugated monoclonal [LM609] antibody (1:100; Millipore GmbH, Schwalbach, Germany) and mouse monoclonal [P1F6] antibody to integrin $\alpha v\beta 5$ (Phycoerythrin) (1:100; Abcam, Cambridge, UK). After a nuclear staining step with DAPI (4',6-diamidino-2-phenylindole, Serva, Heidelberg, Germany) sections are mounted in Fluoromount G (Southern Biotech, USA). Sections are examined using a Leica microscope (DMRE Bensheim, Germany) equipped with a digital camera (F-view XS; Soft Imaging System, Münster, Germany). Mean positive area fractions of SMA and collagen IV (in percent) as well as mean vessel diameters (in µm) are determined from 4 representative animals of each group analyzing 10 fields of view chosen randomly from each rat using Analysis Software (cell$^F$; Olympus Soft Imaging Solutions, Münster, Germany). Immunostainings for CD 31 (endothelial cells) and collagen IV (basal lamina) on tumor vessels are seen to be strongly positively correlated in soft tissue components of bone metastases (data not shown).

For light microscopical analysis, sections are stained with Mayer's hematoxylin (Carl Roth, Karlsruhe, Germany) and eosin (Merck, Darmstadt, Germany), mounted using Eukitt mounting medium (O. Kindler, Freiburg, Germany) and analyzed using a microscope (DM LB; Leica, Wetzlar, Germany) equipped with a digital camera (DFC 320; Leica, Wetzlar, Germany).

2.7 Statistical Analyses

For each animal, volumes of the osteolysis and soft tissue component, amplitude A and exchange rate constant $k_{ep}$ are plotted versus time after tumor cell inoculation (due to technical reasons one animal of the control group can not be evaluated for the amplitude A and $k_{ep}$). Normalization of the data to the corresponding initial value at day 30 for each animal is performed and changes are expressed in percent. For statistical comparisons of data from non-invasive imaging and histological analysis, the respective values are compared between the control and treatment groups using the two-sided Wilcoxon-Test; p-values <0.05 are considered significant.

3. Results

Figure 8:
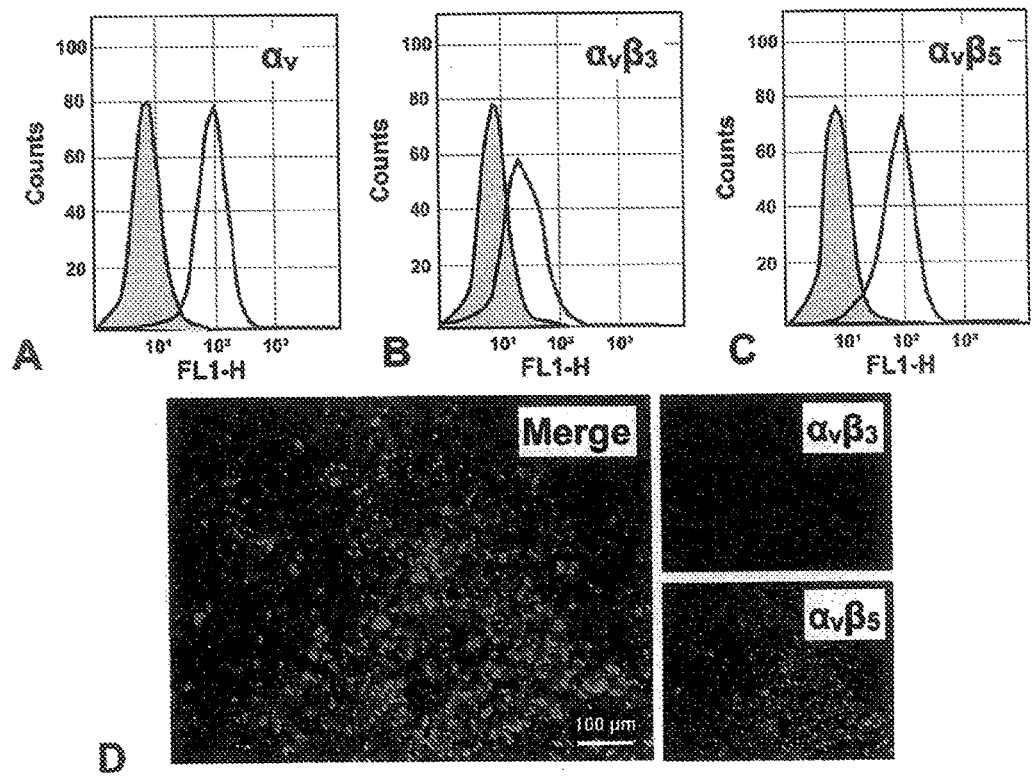
FIG. 8 consists of FIG. 8 A-D and shows expression of integrins of MDA-231 cells in vitro (A-C) and in bone metastases (D). MDA-MB-231 cells were stained with antibodies recognizing the αv chains (17E6; A), αvβ3 (LM609; B) or αvβ5 (P1 F6; C) integrin complexes and expression was evaluated by flow cytometry (open curves), staining due to the second layer reagent was minimal (closed curves). The raw data curves have been smoothed for presentation. Immunohistology section (D) of the soft tissue component from a control animal staining for αvβ3 (red), αvβ5 (green) and DAPI (blue). A merged image (αvβ3, αvβ5, DAPI) is shown as well as single channels for αvβ3 and αvβ5. Bar, 100 µm. 539×396mm (72×72 DPI). (See Example 19)

MDA-MB-231 human breast cancer cells express αvβ5 but only low levels of αvβ3 integrins in vitro. The entire population of MDA-MB-231 cells in vitro expresses αv integrins as detected by the pan alpha-v reagent 17E6 (FIG. 8A). They show low cell surface expression of αvβ3 integrins by flow cytometry using the standard defining antibodies in the literature (36% of the cells are gated; median intensity 3 fold background), while staining strongly for αvβ5 integrins (100% cells gated; median intensity 10 fold background) (FIG. 8B, 8C). MDA-MB-231 also expresses α2, α3, α5, α6, and β1, β4, but not α4 or β6 chains (data not shown). In situ immunohistochemistry shows that soft tissue tumors stained strongly and quite uniformly for αvβ5, but has only weak patches of staining for αvβ3 (FIG. 8D). The results according to FIG. 8 A-D are graphically shown in FIG. 8 (8/21) and commented as follows:

FIG. 8 A-D. Expression of integrins of MDA-MB-231 cells in vitro (A-C) and in bone metastases (D). MDA-MB-231 cells were stained with antibodies recognizing the αv chains (17E6; A), αvβ3 (LM609; B) or αvβ5 (P1F6; C) integrin complexes and expression was evaluated by flow cytometry (9open curves), staining due to the second layer reagent was minimal (closed curves). The raw data curves have been smoothed for presentation. Immunohistology section (d) of the soft tissue component from a control animal staining for αvβ3 (red), αvβ5 (green) and DAPI (blue). A merged image (αvβ3, αvβ5, DAPI) is shown as well as single channels for αvβ3 and αvβ5. Bar, 100 μm. 539×396 mm (72×72 DPI).

Treatment with cilengitide reduces the volume of osteolytic lesions (OL) and soft tissue components (STC) in experimental bone metastases as assessed in vivo with VCT and MRI. Tumor bearing animals are randomly assigned to two groups before therapy is begun at day 30. The mean relative volumes of the osteolytic lesions (OL) and the soft tissue components of bone metastases (STC) increase continuously in untreated rats until the end of the observation time (day 55 post tumor cell injection) compared to the initial values at day 30 after cancer cell injection (FIG. 2A). Mean relative values of the OL volumes have increased by 1.9, 4.5 and 9.7 fold in the control group and by 1.5, 2.4 and 3.5 fold in the treatment group (at days 35, 45 and 55, respectively) when compared to initial values at day 30 (FIG. 2A, FIG. 3A). Significant differences between the groups are found at days 45 (p<0.05) and 55 (p<0.01) for the OL (FIG. 2A). The mean volume of STC have increased by 2.3, 10.4 and 22.5 fold in controls at days 35, 45 and 55, respectively (FIG. 2A). The increase in mean relative STC values in bone metastases of the treatment group, however, increases only by 2.2, 4.9 and 6.3 fold for the volume of STC compared to initial values (FIG. 2A, FIG. 3B). Significant differences between the control and on-therapy groups are recorded at days 45 (p<0.05) and 55 (p<0.01; FIG. 2A) for the STC. In the treatment group, three rats (25%) show new bone formation under therapy with cilengitide as imaged by VCT (FIG. 3C). This bone formation is confined to the osteolytic lesion and no excessive increase in bone mass beyond the osteolyis is observed. Such a de novo bone formation further confirmed by histology does not occur in control animals.

Experimental breast cancer bone metastases treated with cilengitide reveal changes in DCE-MRI derived parameters for both, relative blood volume, and for vessel permeability. For the mean relative values of the DCE-MRI parameter amplitude A, a significant decrease is found in animals treated with the αvβ3/αvβ5 inhibitor at days 45 (102% of initial value; p<0.05) and 55 (93% of initial value; p<0.05) as compared to controls (day 45, 125% and day 55, 105% of initial values) but not on day 35 post inoculation (106% in controls vs. 97% in treated rats; p>0.05) (FIG. 2B, FIG. 4A). DCE-MRI parameter exchange rate constant $k_{ep}$ also reveals significant differences at day 55 post inoculation with increased values in treated animals (72% of initial value; p<0.05) compared to controls (40% of initial value), but not on days 35 (controls, 86% and treated animals, 69%; p>0.05) or 45 (controls, 63% and treated animals, 88%; p>0.05) (FIG. 2B, FIG. 4B).

Histological analysis reveals new bone formation, decreased vessel diameter and reduced co-localization of smooth muscle actin and collagen IV in blood vessels of animals after treatment with cilengitide when compared to untreated controls. In control rats bone metastases contain tumor cells (representing the soft tissue tumor) within areas of bone resorption corresponding to VCT and MR imaging (FIG. 5A). After treatment with cilengitide, newly formed bone is confirmed on hematoxylin/eosin stained sections (FIG. 5B) taken from the proximal tibia of the animal shown in FIG. 3C. Immunofluorescence analysis in control animals reveals irregular vessels with small diameters, indicated by collagen IV staining in the basal lamina of vessels, which are not co-localized with smooth muscle actin (SMA), along with larger vessels showing collagen IV/SMA co-localization (FIG. 5C). After 4 weeks treatment with cilengitide essentially only small and mesh-like vessels are seen, without clear co-localization of SMA and collagen IV (FIG. 5D). Quantification of the immunofluorescent analysis results in significantly decreased mean positive area fractions of SMA (p<0.05) and significantly increased area fractions of collagen IV (p<0.01) in treated animals as compared to controls (FIG. 6A). The ratio of SMA and collagen IV (treated rats: 0.60/3.32; control rats: 0.83/2.37) is significantly decreased in animals after 4 weeks treatment with cilengitide (p<0.01), and the mean vessel diameter in cilengitide-treated bone metastases (6.6 μm) is significantly smaller than in control rats (8.8 μm, p<0.01; FIG. 6B).

4. Discussion

The aim of this study is to assess the effects of the αvβ3/αvβ5 integrin inhibitor cilengitide on breast cancer bone metastases in nude rats transplanted with human MDA-MB-231 breast cancer cells. We use the non-invasive imaging techniques VCT, morphological MRI and DCE-MRI to follow-up longitudinal progression. Our primary findings are that cilengitide treatment, begun a month after tumors are allowed to implant into bone, decreases osteolysis of breast cancer metastases in nude rats and the volume of the soft tissue tumor components. Cilengitide increases intratumoral vascular permeability, reduces the apparent numbers of mature intratumoral vessels, and unexpectedly causes an resumption of bone formation in a quarter of the animals under therapy. We find a significant decrease in osteolysis using VCT during therapy with cilengitide in nude rats. Several studies have reported a decrease of bone resorption in breast cancer bone metastases after inhibition of the integrin αvβ3.[9, 31, 32] However, these groups have used MDA-MB-231 cells engineered and cloned to over express αvβ3 or breast cancer cell lines such as MDA-MB-435 that strongly express this integrin. As the MDA-MB-231 cells we use only express low levels of αvβ3, the anti-resorptive effect observe here may not be primarily due to the inhibition of this integrin on tumor cells, but also of αvβ3 on osteoclasts and on the intratumoral vasculature, and αvβ5 integrin on all three compartments.[12, 33] In previous studies osteoclasts which express high levels of the αvβ3 integrin, bind several RGD-containing ECM proteins including vitronectin, osteopontin, and BSP.[34] By these interactions, αvβ3 is involved in the regulation of osteoclast activity and the inhibition of this integrin is found to reduce osteoclast-mediated bone resorption.[35] Furthermore, as angiogenesis is required for initiation and maintenance of osteoclastic bone resorption, its inhibition by cilengitide might contribute to the observed decrease of osteolysis we observe after cilengitide treatment.[36] As cilengitide cross reacts with human and rat αv integrins the observed effects in our study are due to the inhibition of αvβ3 and αvβ5 integrins on both, MDA-MB-231 as well as on host cells in particular of the vascular and bone compartments. Which compartments are targeted to produce the effects we report here is under investigation.

Interestingly, three animals (25%) treated with cilengitide here show an increase in bone matrix, i.e. new bone formation in the osteolytic lesions, which is not seen in control animals. There are no known therapies in use today for patients suffering from bone metastases, where such an effect is seen. After treatment with bisphosphonates, a sclerotic rim around osteolytic lesions is a common sign for treatment response indicating local bone mineralization, but new bone formation is not seen after this therapy.[37] Both integrins, αvβ3 and αvβ5, are expressed by osteoblasts and are associated with osteoblast migration, adhesion and activity.[38] We have previously shown in this model of breast cancer bone metastases, that the inhibition of BSP also resulted in decreased bone resorption and new bone formation.[28, 39] As BSP binds αvβ3 integrin, the inhibition of either factors, BSP or αvβ3, might result in osteoblastic bone formation via the same pathway.[40] However, the exact mechanism inducing bone regrowth must still be elucidated.

Not only are there anti-resorptive effects, but also the respective soft tissue components have a lower volume than in the control animals, indicating an anti-tumor effect of Cilengitide. Cilengitide inhibits the growth of several experimental tumors including melanomas and glioblastomas.[41, 42] Due to the high expression of αvβ5 and the low expression of αvβ3 of MDA-MB-231 cells, the anti-tumor effect we report here may be a consequence of directly inhibiting αvβ5 on the surface of the breast cancer cells, combined with the anti-angiogenic effects of inhibiting αvβ3 and αvβ5 on the endothelia of tumor vessels.[15] This hypothesis, however, is based only on the integrin expression of MDAMB-231 cells observed in our study, and has to be verified experimentally in further studies. Chen et al. previously observed that MDA-MB-231 cells expressed αvβ3 and αvβ5 integrins at similar levels suggesting that treatment effects of Cilengitide might vary depending on the expression pattern of the respective cell clone used.[43]

Anti-angiogenic effects of cilengitide have been described previously in vitro and in vivo.[15, 18, 41, 44] In our study, cilengitide treatment of experimental breast cancer bone metastases results in a decrease of the amplitude A and an increase of the exchange rate constant $k_{ep}$ as assessed by DCE-MRI. These results indicate a decrease in blood volume and an increase of vessel permeability in these skeletal lesions, compatible with an "antiangiogenic" effect. In experimental glioblastomas and melanomas, a decrease in tumor vascularization and tumor growth followed treatment with cilengitide.[21, 29] It is generally assumed that the anti-angiogenic activity of cilengitide and related inhibitors is due to the experimentally observable inhibition of sprouting and differentiation, and the induction of anoikis of angiogenic endothelial cells relaying on αvβ3 and αvβ5 for adhesion and survival.[15, 45] In our immunohistology analysis we observe vessel remodeling after cilengitide treatment including significantly decreased mean vessel diameter and SMA/collagen IV ratio, indicating that smaller vessels lacking pericyte and smooth muscle cells occur more frequently in these animals than in untreated controls. These results of vessel remodeling rather than complete regression of tumor vessels upon cilengitide treatment are in good agreement with the moderate changes of DCE-MRI parameters A and $k_{ep}$. Taken together, we conclude that cilengitide triggeres a decrease in blood volume (assessed by the amplitude A) due to smaller and partly non-functional blood vessels, and increased vessel permeability (assessed by the exchange rate constant $k_{ep}$) is observed due to the increased number of immature vessels that arose after treatment with cilengitide. Increased vessel permeability as seen in our study was previously reported by Alghisi and colleagues, who reported VE-cadherin delocalization from cell-cell contact sites on cilengitide treatment leading to a loss of cellular contacts and an increase of endothelial monolayer permeability.[46] In bone metastases, this effect might improve local drug delivery to these lesions when combining cilengitide with standard treatments such as bisphosphonates or chemotherapy. In comparison to bisphosphonates showing predominantly anti-osteoclastic and chemotherapy exhibiting mainly cytotoxic effects in bone metastases, cilengitide shows anti-resorptive, anti-tumor and anti-angiogenic efficacy in our study. Due to the favorable safety profile of this drug and the alternative mechanism of action compared to currently used treatments, cilengitide emerges as a promising novel therapy for breast cancer metastasis to bone and could be validated either as a single agent, or in combination with bisphosphonates and chemotherapy in further experimental and clinical studies. Cilengitide might also be a suitable combination partner for ionizing radiation in the treatment of skeletal lesions due to its previously reported radio sensitizing effects in various tumors including breast cancer.[47-49] In some rodent tumor models, a lack of αvβ3 and αvβ5 integrins, or an inhibition by low concentrations of cilengitide stimulate tumor growth.[50, 51] This appears not to be the case in the breast-tumor-to-bone model we report here. Whether one or other of these experimental contexts better reflects the response of human pathologies to αv integrin inhibitors, however, must remain to be proven by clinical trial.[19] In conclusion, treatment of well established experimental breast cancer bone metastases with cilengitide results in an inhibition of bone resorption and soft tissue tumor growth in these osseous lesions and partial regrowth of bone. Although further experimental and clinical studies are required, cilengitide is a possible option for breast cancer patients suffering from metastases to bone.

Acknowledgments

We thank Karin Leotta, Renate Bangert, Lisa Seyler and Catherine Eichhorn for excellent technical assistance. We furthermore thank the Deutsche Forschungsgemeinschaft (SFBTR23) and Merck-Serono for financial support.

5. REFERENCES

1. Guise T A. Breaking down bone: new insight into site-specific mechanisms of breast cancer osteolysis mediated by metalloproteinases. Genes Dev 2009; 23:2117-23.

2. Schwartz M A. Integrin signaling revisited. Trends Cell Biol 2001; 11:466-70.
3. Varner J A, Brooks P C, Cheresh D A. The integrin alpha V beta 3: angiogenesis and apoptosis. Cell Adhes Commun 1995; 3:367-74.
4. Hynes R O. Integrins: bidirectional, allosteric signaling machines. Cell 2002; 110:673-87.
5. Max R, Gerritsen R R, Nooijen P T, Goodman S L, Sutter A, Keilholz U, Ruiter D J, De Waal R M. Immunohistochemical analysis of integrin alpha v beta3 expression on tumorassociated vessels of human carcinomas. Int J Cancer 1997; 71:320-4.
6. Nemeth J A, Nakada M T, Trikha M, Lang Z, Gordon M S, Jayson G C, Corringham R, Prabhakar U, Davis H M, Beckman R A. Alpha-v integrins as therapeutic targets in oncology. Cancer Invest 2007; 25:632-46.
7. Mulder W J, Castermans K, van Beijnum J R, Oude Egbrink M G, Chin P T, Fayad Z A, Löwik C W, Kaijzel E L, Que I, Storm G, Strijkers G J, Griffioen A W, et al. Molecular imaging of tumor angiogenesis using alphavbeta3-integrin targeted multimodal quantum dots. Angiogenesis 2009; 12:17-24.
8. Nemeth J A, Cher M L, Zhou Z, Mullins C, Bhagat S, Trikha M. Inhibition of alpha(v)beta3 integrin reduces angiogenesis, bone turnover, and tumor cell proliferation in experimental prostate cancer bone metastases. Clin Exp Metastasis 2003; 20:413-20.
9. Pecheur I, Peyruchaud O, Serre C M, Guglielmi J, Voland C, Bourre F, Margue C, Cohen-Solal M, Buffet A, Kieffer N, Clezardin P. Integrin alpha(v)beta3 expression confers on tumor cells a greater propensity to metastasize to bone. Faseb J 2002; 16:1266-8.
10. Sloan E K, Pouliot N, Stanley K L, Chia J, Moseley J M, Hards D K, Anderson R L. Tumor-specific expression of alphavbeta3 integrin promotes spontaneous metastasis of breast cancer to bone. Breast Cancer Res 2006; 8:R20.
11. Silvestri I, Longanesi Cattani I, Franco P, Pirozzi G, Botti G, Stoppelli M P, Carriero M V. Engaged urokinase receptors enhance tumor breast cell migration and invasion by upregulating alpha(v)beta5 vitronectin receptor cell surface expression. Int J Cancer 2002; 102:562-71.
12. Inoue M, Ross F P, Erdmann J M, Abu-Amer Y, Wei S, Teitelbaum S L. Tumor necrosis factor alpha regulates alpha(v)beta5 integrin expression by osteoclast precursors in vitro and in vivo. Endocrinology 2000; 141:284-90.
13. Reardon D A, Nabors L B, Stupp R, Mikkelsen T. Cilengitide: an integrin-targeting arginine-glycine-aspartic acid peptide with promising activity for glioblastoma multiforme. Expert Opin Investig Drugs 2008; 17:1225-35.
14. Dechantsreiter M A, Planker E, Matha B, Lohof E, Holzemann G, Jonczyk A, Goodman S L, Kessler H. N-Methylated cyclic RGD peptides as highly active and selective alpha(V)beta(3) integrin antagonists. J Med Chem 1999; 42:3033-40.
15. Nisato R E, Tille J C, Jonczyk A, Goodman S L, Pepper M S. Alpha v beta 3 and alphav beta 5 integrin antagonists inhibit angiogenesis in vitro. Angiogenesis 2003; 6:105-19.
16. Patsenker E, Popov Y, Sickel F, Schneider V, Ledermann M, Sagesser H, Niedobitek G, Goodman S L, Schuppan D. Pharmacological Inhibition of Integrin avb3 aggravates experimental liver fibrosis and suppresses hepatic angiogenesis. Hepatology 50:1501-11.
17. Xiong J P, Stehle T, Zhang R, Joachimiak A, Frech M, Goodman S L, Arnaout M A. Crystal structure of the extracellular segment of integrin alpha V beta3 in complex with an Arg-Gly-Asp ligand. Science 2002; 296:151-5.
18. Buerkle M A, Pahernik S A, Sutter A, Jonczyk A, Messmer K, Dellian M. Inhibition of the alpha-nu integrins with a cyclic RGD peptide impairs angiogenesis, growth and metastasis of solid tumours in vivo. Br J Cancer 2002; 86:788-95.
19. Reardon D A, Fink K L, Mikkelsen T, Cloughesy T F, O'Neill A, Plotkin S, Glantz M, Ravin P, Raizer J J, Rich K M, Schiff D, Shapiro W R, et al. Randomized phase II study of cilengitide, an integrin-targeting arginine-glycine-aspartic acid peptide, in recurrent glioblastoma multiforme. J Clin Oncol 2008; 26:5610-7.
20. Strieth S, Eichhorn M E, Sutter A, Jonczyk A, Berghaus A, Dellian M. Antiangiogenic combination tumor therapy blocking alpha(v)-integrins and VEGF-receptor-2 increases therapeutic effects in vivo. Int J Cancer 2006; 119:423-31.
21. Hodivala-Dilke K. alphavbeta3 integrin and angiogenesis: a moody integrin in a changing environment. Curr Opin Cell Biol 2008; 20:514-9.
22. Taverna D, Moher H, Crowley D, Borsig L, Varki A, Hynes R O. Increased primary tumor growth in mice null for beta3- or beta3/beta5-integrins or selectins. Proc Natl Acad Sci USA 2004; 101:763-8.
23. Bäuerle T, Bartling S, Berger M, Schmitt-Gräff A, Hilbig H, Kauczor H U, Delorme S, Kiessling F. Imaging antiangiogenic treatment response with DCE-VCT, DCE-MRI and DWI in an animal model of breast cancer bone metastasis. Eur J Radiol 2010; 73:280-7.
24. Bäuerle T, Hilbig H, Bartling S, Kiessling F, Kersten A, Schmitt-Gräff A, Kauczor H U, Delorme S, Berger M R. Bevacizumab inhibits breast cancer-induced osteolysis, surrounding soft tissue metastasis, and angiogenesis in rats as visualized by VCT and MRI. Neoplasia 2008; 10:511-20.
25. Mitjans F, Sander D, Adan J, Sutter A, Martinez J M, Jaggle C S, Moyano J M, Kreysch H G, Piulats J, Goodman S L. An anti-alpha v-integrin antibody that blocks integrin function inhibits the development of a human melanoma in nude mice. J Cell Sci 1995; 108 (Pt 8):2825-38.
26. Cheresh D A, Spiro R C. Biosynthetic and functional properties of an Arg-Gly-Asp directed receptor involved in human melanoma cell attachment to vitronectin, fibrinogen, and von Willebrand factor. J Biol Chem 1987; 262:17703-11.
27. Weinacker A, Chen A, Agrez M, Cone R I, Nishimura S, Wayner E, Pytela R, Sheppard D. Role of the integrin alpha v beta 6 in cell attachment to fibronectin. Heterologous expression of intact and secreted forms of the receptor. J Biol Chem 1994; 269:6940-8.
28. Bäuerle T, Adwan H, Kiessling F, Hilbig H, Armbruster F P, Berger M R. Characterization of a rat model with site-specific bone metastasis induced by MDA-MB-231 breast cancer cells and its application to the effects of an antibody against bone sialoprotein. Int J Cancer 2005; 115:177-86.
29. Yamada S, Bu X Y, Khankaldyyan V, Gonzales-Gomez I, McComb J G, Laug W E. Effect of the angiogenesis inhibitor Cilengitide (EMD 121974) on glioblastoma growth in nude mice. Neurosurgery 2006; 59:1304-12.
30. Brix G, Semmler W, Port R, Schad L R, Layer G, Lorenz W J. Pharmacokinetic parameters in CNS Gd-DTPA enhanced MR imaging. J Comput Assist Tomogr 1991; 15:621-8.

31. Harms J F, Welch D R, Samant R S, Shevde L A, Miele M E, Babu G R, Goldberg S F, Gilman V R, Sosnowski D M, Campo D A, Gay C V, Budgeon L R, et al. A small molecule antagonist of the alpha(v)beta3 integrin suppresses MDA-MB-435 skeletal metastasis. Clin Exp Metastasis 2004; 21:119-28.
32. Zhao Y, Bachelier R, Treilleux I, Pujuguet P, Peyruchaud O, Baron R, Clement-Lacroix P, Clezardin P. Tumor alphavbeta3 integrin is a therapeutic target for breast cancer bone metastases. Cancer Res 2007; 67:5821-30.
33. Eliceiri B P, Puente X S, Hood J D, Stupack D G, Schlaepfer D D, Huang X Z, Sheppard D, Cheresh D A. Src-mediated coupling of focal adhesion kinase to integrin alpha(v)beta5 in vascular endothelial growth factor signaling. J Cell Biol 2002; 157:149-60.
34. Duong L T, Rodan G A. Integrin-mediated signaling in the regulation of osteoclast adhesion and activation. Front Biosci 1998; 3:d757-68.
35. Nakamura I, Duong le T, Rodan S B, Rodan G A. Involvement of alpha(v)beta3 integrins in osteoclast function. J Bone Miner Metab 2007; 25:337-44.
36. Andersen T L, Sondergaard T E, Skorzynska K E, Dagnaes-Hansen F, Plesner T L, Hauge E M, Plesner T, Delaisse J M. A physical mechanism for coupling bone resorption and formation in adult human bone. Am J Pathol 2009; 174:239-47.
37. Hamaoka T, Madewell J E, Podoloff D A, Hortobagyi G N, Ueno N T. Bone imaging in metastatic breast cancer. J Clin Oncol 2004; 22:2942-53.
38. Lai C F, Cheng S L. Alphavbeta integrins play an essential role in BMP-2 induction of osteoblast differentiation. J Bone Miner Res 2005; 20:330-40.
39. Bäuerle T, Peterschmitt J, Hilbig H, Kiessling F, Armbruster F P, Berger M R. Treatment of bone metastasis induced by MDA-MB-231 breast cancer cells with an antibody against bone sialoprotein. Int J Oncol 2006; 28:573-83.
40. Karadag A, Ogbureke K U, Fedarko N S, Fisher L W. Bone sialoprotein, matrix metalloproteinase 2, and alpha (v)beta3 integrin in osteotropic cancer cell invasion. Journal of the National Cancer Institute 2004; 96:956-65.
41. Mitjans F, Meyer T, Fittschen C, Goodman S, Jonczyk A, Marshall J F, Reyes G, Piulats J. In vivo therapy of malignant melanoma by means of antagonists of alphav integrins. Int J Cancer 2000; 87:716-23.
42. MacDonald T J, Taga T, Shimada H, Tabrizi P, Zlokovic B V, Cheresh D A, Laug W E. Preferential susceptibility of brain tumors to the antiangiogenic effects of an alpha (v) integrin antagonist. Neurosurgery 2001; 48:151-7.
43. Chen Q, Manning A D, Millar H, McCabe F L, Ferrante C, Sharp C, Shahied-Arruda L, Doshi P, Nakada M T, Anderson G M. CNTO 95, a fully human anti αv integrin antibody, inhibits cell signalin, migration, invasion, and spontaneous metastasis of human breast cancer cells. Clin Exp Metastasis 2008; 25:139-48.
44. Patsenker E, Popov Y, Stickel F, Schneider V, Ledermann M, Sagesser H, Niedobitek G, Goodman S L, Schuppan D. Pharmacological inhibition of integrin alphavbeta3 aggravates experimental liver fibrosis and suppresses hepatic angiogenesis. Hepatology 2009; 50:1501-11.
45. Brooks P C, Montgomery A M, Rosenfeld M, Reisfeld R A, Hu T, Klier G, Cheresh D A. Integrin alpha v beta 3 antagonists promote tumor regression by inducing apoptosis of angiogenic blood vessels. Cell 1994; 79:1157-64.
46. Alghisi G C, Ponsonnet L, Ruegg C. The integrin antagonist cilengitide activates alphaVbeta3, disrupts V E-cadherin localization at cell junctions and enhances permeability in endothelial cells. PLoS One 2009; 4:e4449.
47. Abdollahi A, Griggs D W, Zieher H, Roth A, Lipson K E, Saffrich R, Gröne H J, Hallahan D E, Reisfeld R A, Debus J, Niethammer A G, Huber P E. Inhibition of alpha(v)beta3 integrin survival signaling enhances antiangiogenic and antitumor effects of radiotherapy. Clin Cancer Res 2005; 11:6270-9.
48. Mikkelsen T, Brodie C, Finniss S, Berens M E, Rennert J L, Nelson K, Lemke N, Brown S L, Hahn D, Neuteboom B, Goodman S L. Radiation sensitization of glioblastoma by cilengitide has unanticipated schedule-dependency. Int J Cancer 2009; 124:2719-27.
49. Albert J M, Cao C, Geng L, Leavitt L, Hallahan D E, Lu B. Integrin alpha v beta 3 antagonist Cilengitide enhances efficacy of radiotherapy in endothelial cell and non-smallcell lung cancer models. Int J Radiat Oncol Biol Phys 2006; 65:1536-43.
50. Reynolds L E, Wyder L, Lively J C, Taverna D, Robinson S D, Huang X, Sheppard D, Hynes R O, Hodivala-Dilke K M. Enhanced pathological angiogenesis in mice lacking beta3 integrin or beta3 and beta5 integrins. Nat Med 2002; 8:27-34.
51. Reynolds A R, Hart I R, Watson A R, Welti J C, Silva R G, Robinson S D, Da Violante G, Gourlaouen M, Salih M, Jones M C, Jones D T, Saunders G, et al. Stimulation of tumor growth and angiogenesis by low concentrations of RGD-mimetic integrin inhibitors. Nat Med 2009; 15:392-400.

The disclosure of the above given documents is incorporated into this application by reference in their entirety.

6. Figure Legends

FIG. 8 (FIG. 8 A-D). Expression of integrins of MDA-MB-231 cells in vitro (A-C) and in bone metastases (D). MDA-MB-231 cells are stained with antibodies recognizing the αv chains (17E6; A), αvβ3 (LM609; B) or αvβ5 (P1 F6; C) integrin complexes and expression is evaluated by flow cytometry (open curves), staining due to the second layer reagent is minimal (closed curves). The raw data curves are smoothed for presentation. Immunohistology section (D) of the soft tissue component from a control animal staining for αvβ3 (red), αvβ5 (green) and DAPI (blue). A merged image (αvβ3, αvβ5, DAPI) is shown as well as single channels for αvβ3 and αvβ5. Bar, 100 μm.

Figure 9:
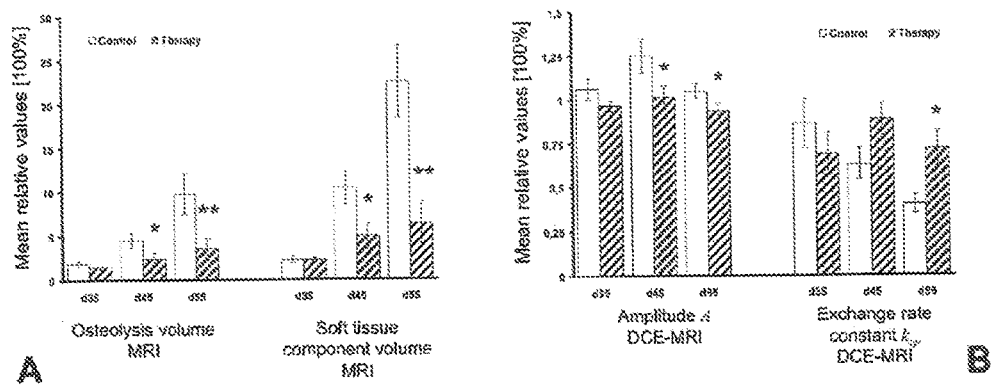
FIG. 9 consists of FIG. 9 A, B and shows volumetric analyses of osteolytic lesions and soft tissue tumors (A) as well as quantification of mean relative parameters A and kep (B) from experimental bone metastases: Comparison between untreated and cilengitide-treated rats. Values are given in percent and are presented as mean values relative to initial values determined at day 30 after cancer cell inoculation at which time cilengitide therapy was started. Y-axis, mean relative values in percent (times 100); X-axis, days after cancer cell inoculation; error bars, SEM; *, p<0.05; **, P<0.01. 452×173mm (72×72 DPI). (See Example 19).

FIG. 9 (Fig. 9 A- B). Volumetric analyses of osteolytic lesions and soft tissue tumors (A) as well as quantification of mean relative values of parameters A (associated with blood volume) and $k_{ep}$ (associated with vessel permeability) (B) from experimental bone metastases: Comparison between untreated and cilengitide-treated rats. Values are given in percent and are presented as mean values relative to initial values determined at day 30 after cancer cell inoculation, at which time cilengitide therapy is started. Y-axis, mean relative values in percent (times 100); X-axis, days (d) after cancer cells inoculation (d35, d45, d55); error bars, SEM; *, p<0.05; **, p<0.01.

Figure 10:
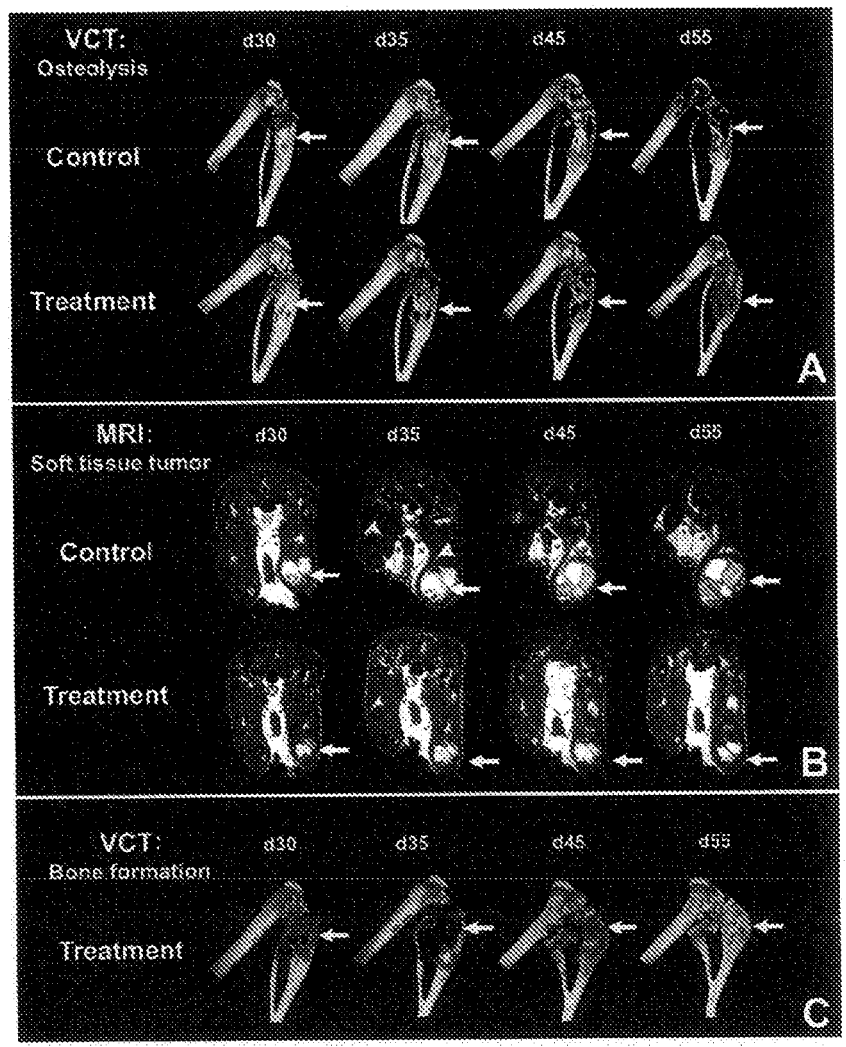
FIG. 10 consists of FIG. 10 A-C and shows morphological characteristics of vehicle treated and Cilengitide-treated experimental bone metastases. Volumes of the osteolytic lesions (A, C) and soft tissue tumours (B) were determined by the analysis of images acquired by VCT and MRI, respectively, at days 30, 35, 45 and 55 after cancer cell injection. Therapy with Cilengitide commenced after imaging on day 30. Compare differences in bone loss and soft tumour burden between vehicle treated (A, B: upper rows) as well as Cilengitide-treated animals resulting in inhibition of osteolysis and bone formation (A, B: upper rows; C). Representative VCT images: 3D bone surface reconstructions, and MRI: axial slices from T2-weighted imaging. Arrows, proximal tibia of the hind leg. 323×402mm (72×72 DPI). (See Example 19).

FIG. 10 (Fig. 10 A-C). Morphological characteristics of vehicle treated and cilengitide-treated experimental bone metastases. Volumes of the osteolytic lesions (A, C) and soft tissue tumors (B) are determined by the analysis of images acquired by VCT and MRI, respectively, at days 30, 35, 45 and 55 after cancer cell injection. Therapy with cilengitide commences after imaging on day 30. Compare differences in bone loss and soft tumor burden between vehicle treated (A, B: upper rows) as well as cilengitide-treated animals resulting in inhibition of osteolysis and bone formation (A, B:

lower rows; C). Representative VCT images: 3D bone surface reconstructions, and MRI: axial slices from T2-weighted imaging. Arrows, proximal tibia of the hind leg.

Figure 11:
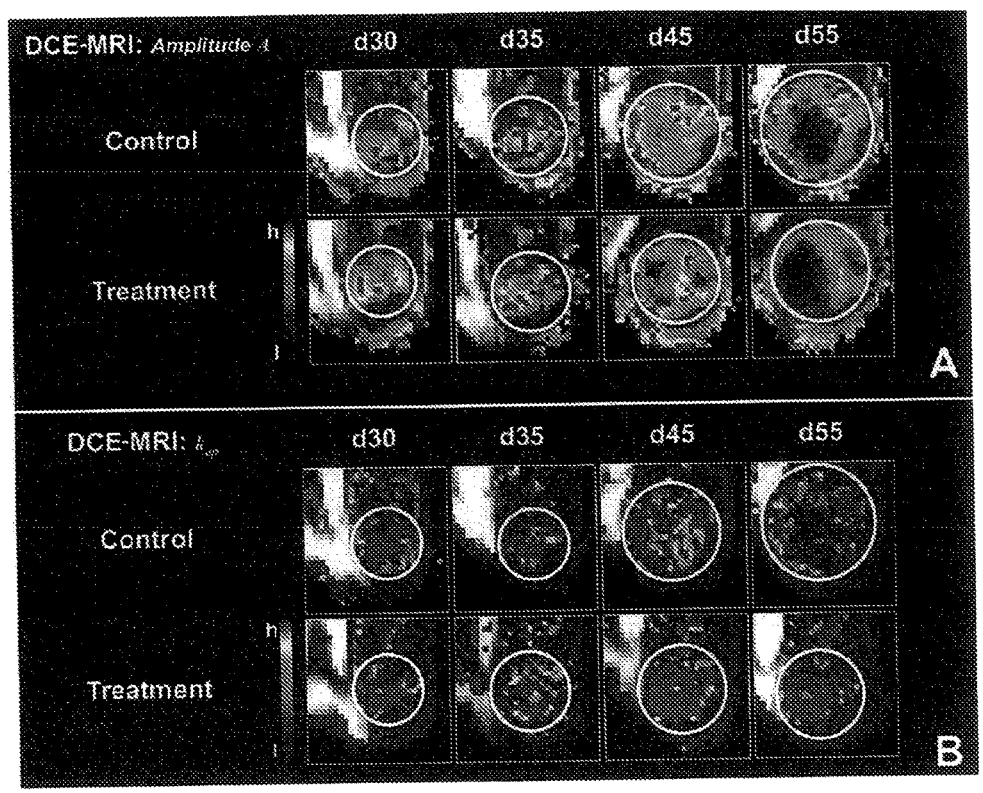
FIG. 11 consist of FIG. 11 A, B and shows DCE-MRI-acquired colour maps depicting functional parameters of bone metastases amplitude A (A) and exchange rate constant kep (B): Comparison between untreated and Cilengitide-treated rats at days 30, 35, 45 and 55 after cancer cell inoculation. Cilengitide treatment began following imaging at day 30. Rats bearing MDA-MBE-231 bone metastases were imaged at day 30, and then following control (upper rows) or Cilengitide (lower rows) treatment. These colour maps were calculated by the use of DynaLab software, red colour denotes high (h) values for the given parameters, blue colour denotes low (l) values. The same scaling ranges were used to produce these images for experimental and control animals. 440×351mm (72×72 DPI). (See Example 19).

FIG. 11 (FIG. 11 A-B). DCE-MRI-acquired color maps depicting functional parameters of bone metastases amplitude A (associated with blood volume) (A) and exchange rate constant $k_{ep}$ (associated with vessel permeability) (B): Comparison between untreated and cilengitide-treated rats at days 30, 35, 45 and 55 after cancer cell inoculation. Cilengitide treatment begins following imaging at day 30. Rats bearing MDAMB- 231 bone metastases are imaged at day 30, and then following control (upper rows) or cilengitide (lower rows) treatment. These color maps are calculated by the use of DynaLab software, red color denotes high (h) values for the given parameter, blue color denotes low (I) values. The same scaling ranges are used to produce these images for experimental and control animals.

Figure 12:
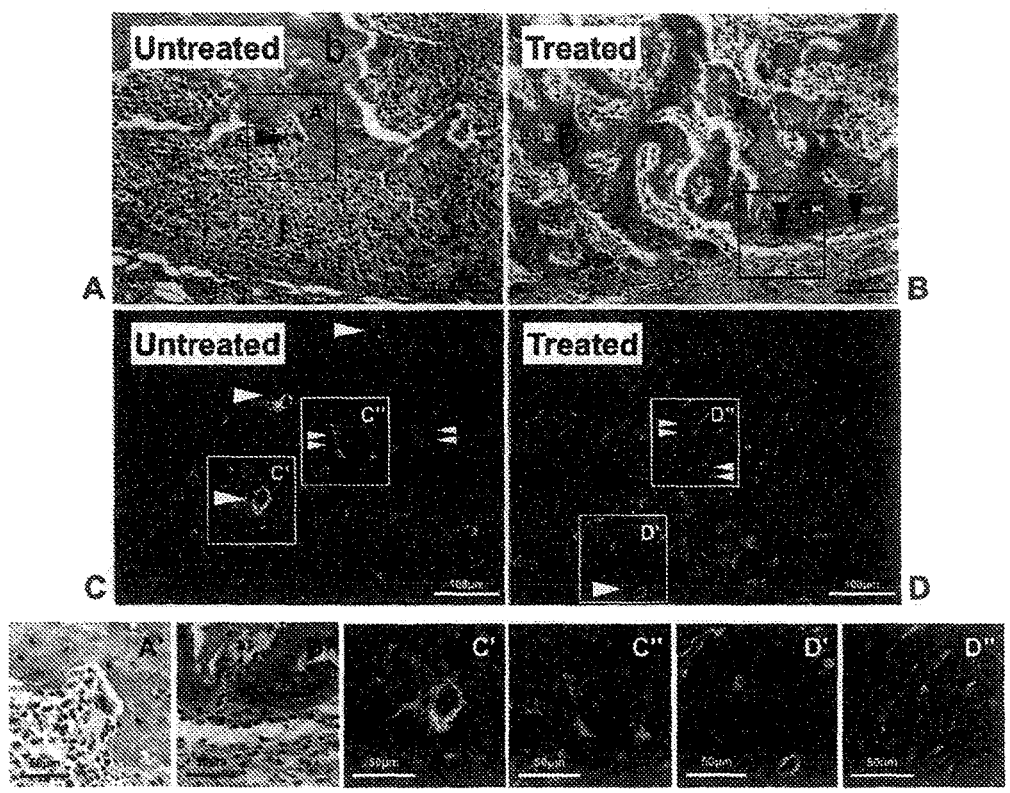
FIG. 12 consists of FIG. 12 A-D and shows histologic analysis of experimental breast cancer bone metastases of untreated and Cilengitide-treated rats. Hematoxylin/eosin stained sections of an osteolytic lesion in a control rat (A; t, tumour cells; b, bone; arrow, osteoclast) and new bone formation in a treated rat (B; b, arrows, osteoclasts). Immunohistology sections of the soft tissue component from a control animal (C) and a Cilengitide-treated rat (D). Green colour shows collagen IV staining whereas red denotes structures staining for smooth muscle actin; blue, cell nuclei. Arrows point at larger vessels with partial co-localisation of smooth muscle actin and collagen IV, while double arrows indicate smaller vessels without clear co-localisation of green and red staining. Enlarged images of the highlighted structures are shown below (A', B', C', C", D', D"). A-D, bar 100 μm; A'-D", bar 50 μm. 478×371mm (72×72 DPI). (See Example 19).

FIG. 12 (FIG. 12 A-D). Histologic analysis of experimental breast cancer bone metastases of untreated and cilengitide-treated rats. Hematoxylin/eosin stained sections of an osteolytic lesion in a control rat (A; t, tumor cells; b, bone; arrow, osteoclast) and new bone formation in a treated rat (B; b, bone; arrows, osteoblasts). Immunohistology sections of the soft tissue component from a control animal (C) and a cilengitide-treated rat (D). Green color shows collagen IV staining whereas red denotes structures staining for smooth muscle actin; blue, cell nuclei. Arrows point at larger vessels with partial co-localization of smooth muscle actin and collagen IV, while double arrows indicate smaller vessels without clear co-localization of green and red staining. Enlarged images of the highlighted structures are shown below (A', B', C', C", D', D"). A-D, bar 100μm; A'-D", bar 50μm.

Figure 13:
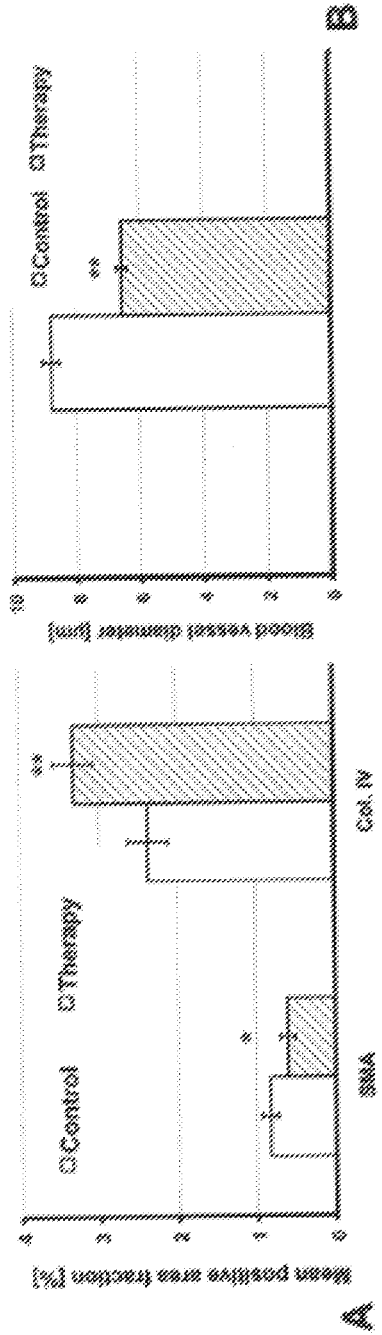
FIG. 13 consist of FIG. 13 A, B and shows the quantification of histological analysis. Values of fractional mean area stained for smooth muscle actin (SMA) and collagen IV (Col. IV) are expressed as percent total area examined (A), while the blood vessels by a meters are presented as mean values in pm (B). Error bars, SEM; *, p<0.05; **, p<0.01. 548×152mm (72×72 DPI). (See Example 19).

FIG. 13 (FIG. 13 A-B). Quantification of histological analysis. Values of fractional mean area stained for smooth muscle actin (SMA) and collagen IV (Col. IV) are expressed as percent total area examined (A), while the blood vessel diameters are presented as mean values in pm (B). Error bars, SEM; *, $p<0.05$; **, $p<0.01$.

Example 20

Study 003: 4T1 Orthotopic Model

4T1 mouse breast tumour cells were orthotopically inoculated into the third mammary fat pad of female BALB/c mice. The mice were randomised into groups when the tumors reached a size of approximately 40 mm$^3$.

The mice in each group received treatment with either Vehicle Control (Placebo), EMD 121974 (75, 150 or 300 mg/kg as Composition according to Example 18) or Taxol® (8 mg/kg). The Vehicle Control and EMD 121974 were administered by subcutaneous injection, daily; Taxol® was administered by intravenous injection three times per week.

Body weight and tumour volume measurements were made for all mice three times per week. The lungs and liver were excised from all mice at termination. For lung metastasis assessment surface metastases of the lungs were counted and for liver metastasis assessment H&E-stained sections of liver were assessed for the presence and number of micro-metastases.

Figure 14:
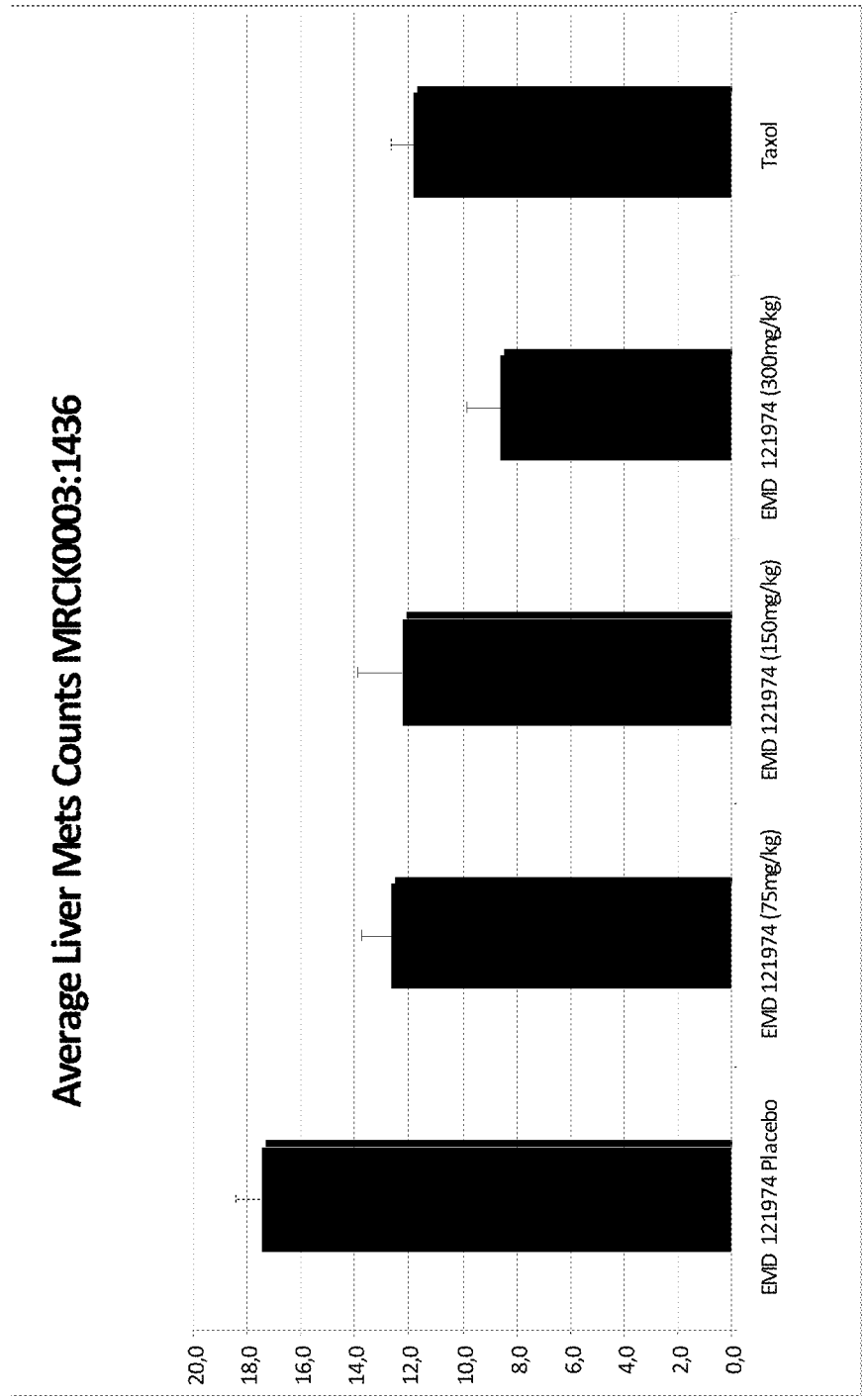
FIGS. 14 and 15 show the results of the Study 003: 4T1 orthotopic model (See Example 20).
Figure 15:
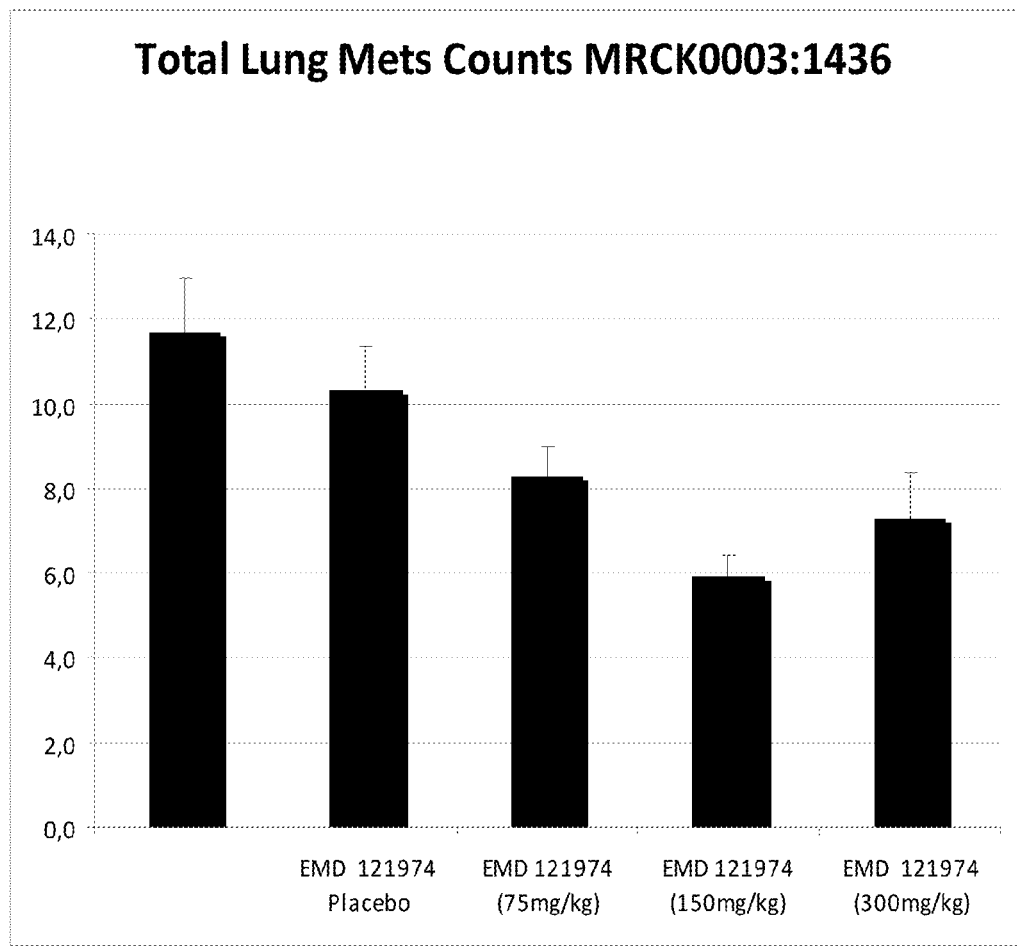

Result: Daily treatment with EMD 121974 inhibited spontaneous liver metastasis formation comparable to Taxol (significant for all doses) and spontaneous lung metastasis formation comparable to Taxol (significant for 300 mg/kg/day). The results are shown in FIGS. 14 and 15

Example 21

Study 006: 4T1 Survival Model

4T1 mouse breast tumour cells were orthotopically inoculated into the fourth mammary fat pad of female BALB/c mice. Treatment started seven days post-inoculation (Day 0), when the mice were randomised, based on tumour size.

Animals received treatment with either Vehicle Control (Placebo), EMD 121974 (75, 150 or 300 mg/kg as a Composition according to Example 18), or Taxol® (8 mg/kg). The Vehicle Control and EMD 121974 were administered daily by subcutaneous injection. Taxol® was administered three times weekly by intravenous injection. To assess the survival of tumor bearing animals a mastectomy was performed 11 days post-inoculation (4 days after treatment start). Animals were monitored daily for clinical symptoms and were culled if body weight loss in any animal exceeded 15% of initial weight, the animal was culled or disease progression was observed (e.g. severe breathing difficulties). Body weight measurements were made three times per week.

Figure 16:
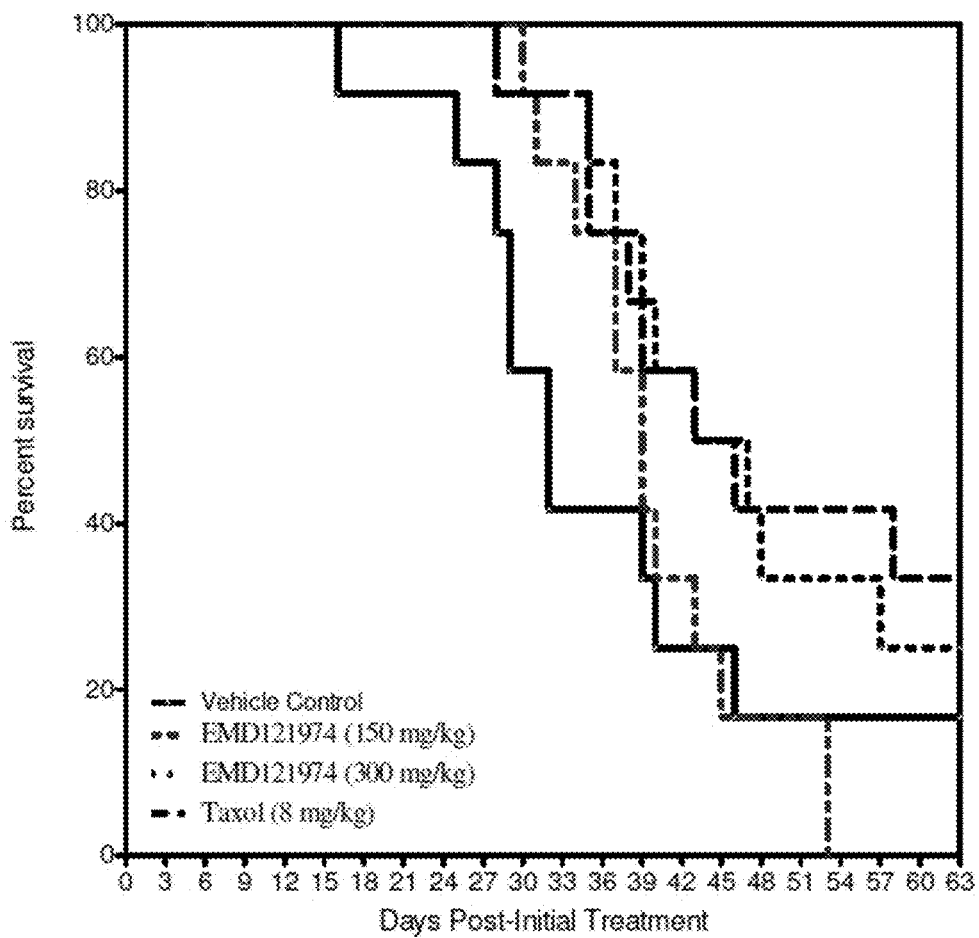
FIG. 16 shows the results of the Study 006: 4T1 survival model (See Example 21).

Result: Daily treatment with 300 mg/kg EMD 121974 resulted in a comparable survival as Taxol. The results are shown in FIG. 16

Example 22

Study 007: MDA-MB-468—Primary Tumor Growth

MDA-MB468 human breast tumour cells were orthotopically inoculated into the third mammary fat pad of female BALB/c nu/nu mice. The mice were randomised into groups when the tumors reached a size of approximately 40 mm$^3$.

The mice in each group received treatment with either Vehicle Control (Placebo) or EMD 121974 (75, 150 or 300 mg/kg as a Composition according to Example 18) by daily subcutaneous injection. Body weight and tumour volume measurements were made for all mice three times per week.

Result: Daily treatment with EMD 121974 as a composition according to the invention inhibited tumor growth of MDA-MB-468 tumors (tumour volume for all three dosing groups (75, 150 or 300 mg/kg) below 200 mm$^3$ on day 60, tumour volume for Vehicle Control higher than 350 mm$^3$ on day 60. Results are shown in detail below:

Example 23

Figure 17:
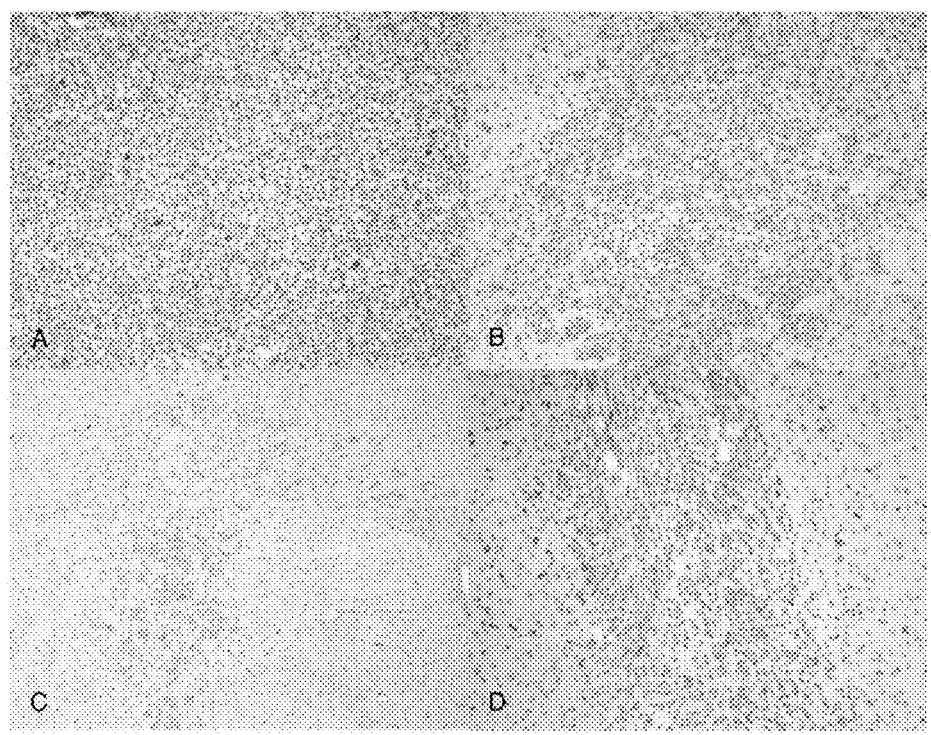
FIG. 17 shows the synergistic effect of the combination of cilengitide with radiation in U251 MG xenograft orthotopic brain model in nude rat: cell death response amplified by cilengitide in presence of radiotherapy (See Example 23).

Synergistic Effect of the Combination of Cilengitide with Radiation in U251 MG Xenograft Orthotopic Brain Model in Nude Rat Caspase 3 Staining (Shown in FIG. 17)

A. Control 40×, B. Cilengitide alone 40×, C) RT alone 40× D) Cilengitide±RT 40×

Red stain shows extent of caspase 3, a protein responsible for apoptosis, in these histological sections of rat brains implanted with U251 MG and treated as indicated.

TABLE 1

Histologic tumor volumes (using Alu ISH) Tumor volumes were calculated using serial sections of Alu ISH-stained sections at time of symptoms (Control, RT and Cilengitide groups) or at 4 months (Cilengitide + RT). Thresholded images from serial sections were pixel-counted and serial areas summed to generate tumor volume.

| Treatment Group | Days post implant (range) | Tumor volume (mm³) median | Number of animals |
| --- | --- | --- | --- |
| Control | 38 (36-43) | 40.4 (30-120) | 6 |
| Cilengitide alone | 40 (40-41) | 175 (158-208) | 3 |
| RT alone | 80 (70-83) | 210 (176-245) | 3 |
| Cilengitide + RT | 131 (≥131) | 0.10 (0.06-0.14) | 4 |

Figure 18:
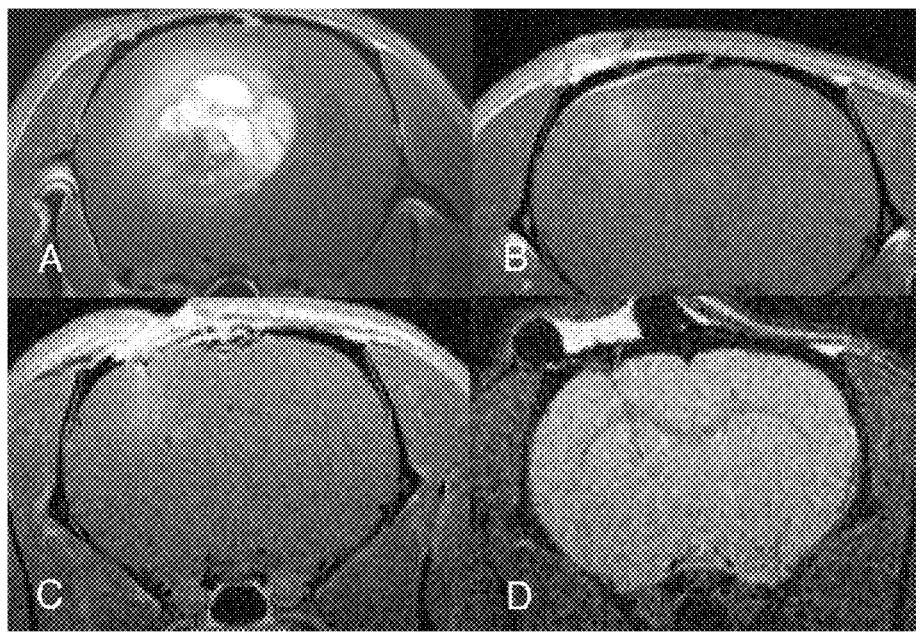
FIG. 18 shows the representative MRI sections of rat brains implanted with U251 and treated. from A. Control, d49 T1+ Gd B. cilengitide alone, d17 C. RT alone d18 D. cilengitide+RT d68(T2). Control at time of sacrifice (A) shows significant mass effect and irregular contrast enhancement. Note that cilengitide alone animal (B) is imaged at 17d, not at survival endpoint, but contrast-enhancing tumor is visible. RT alone animal is also imaged early (C), but cilengitide+RT animal (D) is imaged at 68 days and no tumor is visible, even by T2-MRI, although the injection tract is seen. (See Example 23).
Figure 19:
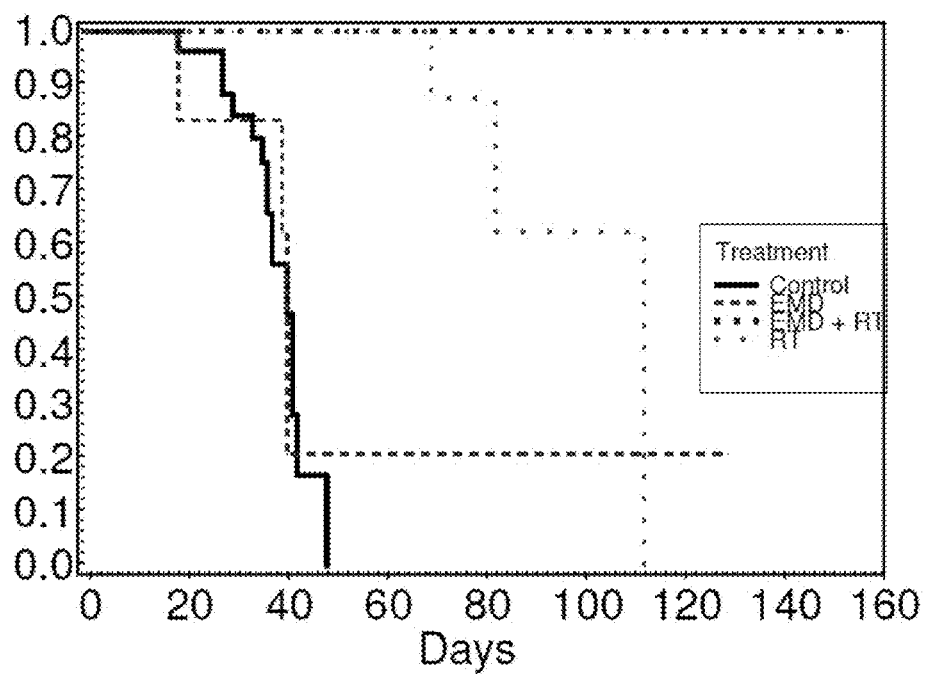
FIG. 19: Kaplan Meir Survival Plot. U251 Control (n=10), Cilengitide alone (n=4), RT alone (n=8) Cilengitide+RT (n=9); Vertical axis shows probability of survival, horizontal axis shows time in days. (See Example 23).
Figure 21:
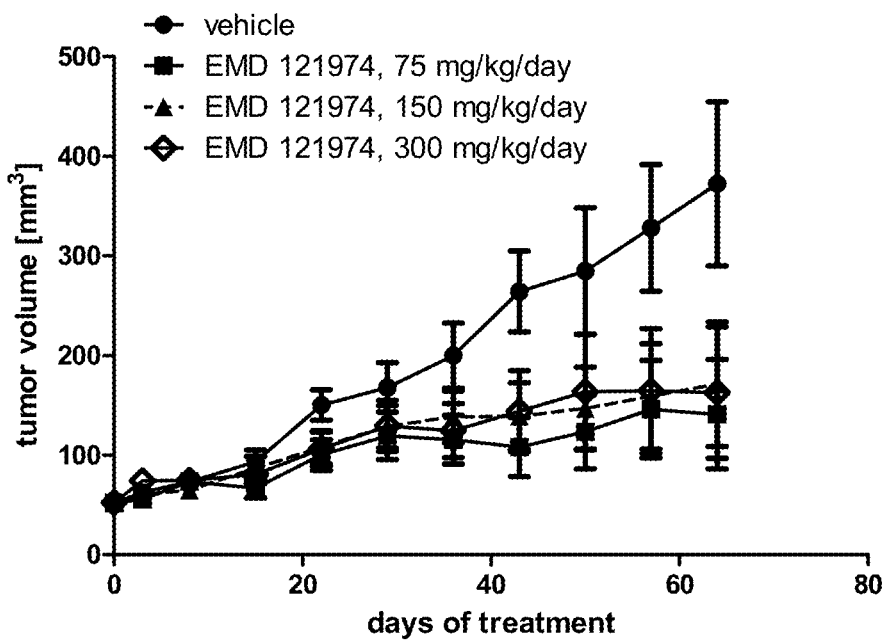
FIG. 21: Cilengitide in MDA-MB-468—primary tumor growth model; Daily treatment with EMD 121974 as a composition according to Example 18 inhibited tumor growth of MDA-MB-468 tumors (tumour volume for all three dosing groups (75, 150 or 300 mg/kg) below 200 mm$^3$ on day 60, tumour volume for Vehicle Control higher than 350 mm$^3$ on day 60 (See Example 22).

FIG. 18: Representative MRI sections of rat brains implanted with U251 and treated. from A. Control, d49 T1+ Gd B. Cilengitide alone, d17 C. RT alone d18 D. Cilengitide+RT d68(T2). Control at time of sacrifice (A) shows significant mass effect and irregular contrast enhancement. Note that Cilengitide alone animal (B) is imaged at 17d, not at survival endpoint, but contrast-enhancing tumor is visible. RT alone animal is also imaged early (C), but Cilengitide+RT animal (D) is imaged at 68 days and no tumor is visible, even by T2-MRI, although the injection tract is seen FIG. 19: Kaplan Meir Survival Plot. U251 Control (n=10), Cilengitide alone (n=4), RT alone (n=8) Cilengitide+RT (n=9)

Vertical axis shows probability of survival.
Horizontal axis shows time in days.

TABLE 2

Median Survival Estimates and Log rank p-values. Significant survival benefit is seen for combined Cilengitide (EMD) and RT over any other modality.

| Comparison | Median Survival in Days | P-value |
| --- | --- | --- |
| Control vs RT | 41 vs 113 | <0.001* |
| Control vs EMD | 41 vs 41 | 0.884 |
| Control vs EMD + RT | 41 vs >154 | <0.001* |
| RT vs EMD | 113 vs 41 | 0.142 |
| RT vs EMD + RT | >154 vs 113 | 0.004* |
| EMD vs EMD + RT | 41 vs >154 | <0.001* |

RT is radiotherapy. Single dose. EMD is cilengitide. Single dose.

Example 23

Inhibition of αVβ3 and αVβ5 Integrins by Cilengitide Improved Tumor Response to Radiation in Human Head and Neck Squamous Cell Carcinoma and Non-Small Cell Lung Cancer Models Purpose: Integrins are implicated in resistance of solid tumors to therapies, including radiation therapy, suggesting that their inhibition would enhance efficacy of tumor therapy. Because cilengitide, a cyclic Arg-Gly-Asp (RGD)-derived peptide, inhibits αVβ3 and αVβ5 integrins, we investigated the efficacy of cilengitide in enhancing in vitro cancer cell radiosensitivity and in vivo radioresponse of cancer xenografts.

Methods: Three non-small cell lung carcinoma lines (NSCLCs) (H460, A549 and H1299) and three head and neck squamous cell carcinoma lines (HNSCCs) (FaDu, SCC-15 and SCC-25) cell lines were used for in vitro experiments. Of these, H460 and FaDu were used for in vivo testing when grown as xenografts in nude mice. The effects of cilengitide (1-50 μg/ml, 24 h) on in vitro cell viability was determined by MTS assay and on cellular radiosensitivity by clonogenic cell survival assay after exposing the cells to graded single doses of γ-radiation with or without cilengitide (given 1 h before and continued for 23 h after irradiation). In vivo effect of cilengitide on radioresponse of xenografts was assessed by tumor growth delay. When tumor xenografts reached 7 mm in diameter cilengitide treatment (30 or 60 mg/d/5 or 10 days) was initiated followed by a single dose of 15 Gy local radiation (using $^{137}$Cs γ-ray source), when the tumors reached 8 mm.

Results: Cilengitide (5 μg/ml, 24 h) reduced in vitro viability of 7 out of 8 cell lines tested, which ranged between 71.4±2.2% (SCC-15) and 27.8±4.2% (H1299). In general, NSCLCs were more sensitive to cilengitide than HNSCCs. When combined with radiation, cilengitide significantly enhanced the radiosensitivity of all 3 NSCLC, by enhancement factors of 1.35 for H460, 1.56 for A549 and 1.3 for H1299. In contrast, cilengitide exerted only an additive effect on radiosensitivity of HNSCC lines. However, in vivo tumor growth delay studies showed that cilengitide as a single agent had no antitumor activity, but in combination with radiation it significantly enhanced response of both H460 (NSCLC) and FaDu (HNSCC) tumor xenografts. The enhancement factors were 1.7 for H460 and 2.0 for FaDu.

Conclusion: The results showed that cilengitide reduced in vitro cell viability of lung and head and neck cancer cells. When combined with radiation, the drug enhanced radiosensitivity of lung carcinoma cells. Cilengitide was effective in enhancing radiation response of both lung (H460) and head and neck (FaDu) tumor xenografts. These results suggest that cilengitide has potential to improve the treatment outcome of patients with NSCLC and HNSCC when combined with radiotherapy.

Example 24

Cilengitide in Combination with Herceptin Enhances Efficacy in the Her2+ Breast Cancer Model BT474

BT474 human breast cancer cells were subcutaneously injected into Balbc nu/nu mice. The mice were randomized into different treatment groups when the tumors reached a mean tumor volume of approximately 125 mm³. Mice received vehicle or 300 mg/kg Cilengitide s.c. formulation by daily subcutaneous injection or 2 mg/kg Herceptin twice weekly by iv injection, Body weight and tumour volume measurements were performed twice a week.

Graphical Display of Treatment Schedule Given in FIG. 20:

BT474*, sc

*Continuous supplementation with estrogen required

Tabular Display of results:

| | Progressive disease | Stable disease | Partial Response | Complete Regression |
| --- | --- | --- | --- | --- |
| Herceptin | 1 | 3 | 5 | 1 |
| Herceptin + Cilengitide s.c. | 1 | 2 | 1 | 6 |

Analysis includes animals which died within experiment due to estrogen toxicity

Results: Monotherapy treatment with 300 mg/kg Cilengitide did not inhibit the tumor growth of Her2+ BT474 tumors. However, continuous treatment with Cilengitide after treatment stop with Herceptin resulted in an enhanced anti-tumor response. In the Herceptin group tumors started to regrow or were stabilized. Only in one animal the tumor completely regressed. In contrast, in the combination group tumors completely regressed in 60% of the animals. Thus, Combination of Herceptin (6 weeks of treatment) with continuous treatment of Cilengitide results in an enhanced anti-tumor response leading to complete regressions in 60% of treated animals compared to 10% in Hercpetin treated animals (See FIG. 20).

The invention claimed is:

1. A method for the treatment of cancer wherein said cancer expresses αvβ3 and/or αvβ5 integrins, comprising a step of subcutaneously and/or intramuscularly administering to a patient who has been identified as having a cancer which expresses αvβ3 and/or αvβ5 integrins an effective amount of a composition which is a suspension comprising:
   a) 12 to 90% of the oligopeptide cyclo-(Arg-Gly-Asp-DPhe-NMeVal) having a solubility in water at 20° C. between 3 mg/ml and 10 mg/ml,
   b) 0.01 to 60% of one or more lipophilic and/or amphiphilic compounds having a molar weight in the range of 200 g/mol to 2000 g/mol, and optionally
   c) 0 to 87.99% of water, with the proviso that the sum of a), b) and c) sums up to 80 or more percent of the total composition with the proviso that said suspension composition contains 100 mg/ml or more of said oligopeptide, and with the further proviso that said suspension composition comprises 40% or more of said oligopeptide as solid particles.

2. The method according to claim 1, wherein said composition is a pharmaceutical composition.

3. The method according to claim 1, wherein said patient is a human.

4. The method as claimed in claim 1, wherein in said composition at least one of the one or more lipophilic and/or amphiphilic compounds according to b) comprises:
   i) a glycerol moiety,
   ii) one or more fatty acid moieties, and/or
   iii) one or more fatty alcohol moieties.

5. The method as claimed in claim 1, wherein in said composition at least one of the one or more amphiphilic compounds according to b) comprises a hydrophilic moiety.

6. The method according to claim 5, wherein in said composition the hydrophilic moiety comprises an ethanolamine moiety, a choline moiety, a phosphatidyl moiety, a sulfatidyl moiety, and/or a salt thereof.

7. The method as claimed in claim 5, wherein in said composition the hydrophilic moiety comprises an phosphoethanolamine moiety, a phosphatidylcholine moiety, a phosphatidylglycerol moiety, a sulfatidylglycerol moiety, and/or a salt thereof.

8. The method as claimed in claim 6, wherein in said composition the hydrophilic moiety comprises an phosphoethanolamine moiety, a phosphatidylcholine moiety, a phosphatidylglycerol moiety, a sulfatidylglycerol moiety, and/or a salt thereof.

9. The method according to claim 1, wherein in said composition the one or more lipophilic compounds according to b) comprise one or more compounds selected from natural oils and synthetic oils, and mixtures thereof, and/or wherein the one or more amphiphilic compounds according to b) comprise one or more compounds selected from amphiphilic lipids having phosphatidyl-polyol or sulfatidyl-polyol groups as the hydrophilic part, and derivatives, salts and/or alcoholates thereof.

10. The method according to claim 9, wherein in said composition the phosphatidyl- or sulfatidyl-polyoles are selected from
   a) polyphosphatidylglycerol, triphosphatidylglycerol, diphosphatidylglycerol, monophosphatidylglycerol, and/or
   b) polysulfatidylglycerol, trisulfatidylglycerol, disulfatidylglycerol, and monosulfatidylglycerol.

11. The method according to claim 1, wherein, in said composition the amphiphilic compounds are selected from the group consisting of dioleoylphosphatidylglycerol, dimyristoylphosphatidylglycerol, dimyristoylphosphatidylcholine, distearoylphosphatidylglycerol, dioleoylglycerophosphocholine, dipalmitoylglycerophosphoglycerol, distearoylglycerophosphoethanolamine, egg phosphatidylcholine, soy phosphatidylcholine, and pharmaceutically acceptable derivatives, salts and alcoholates thereof.

12. The method according to claim 1, wherein, in said composition the amphiphilic compounds are selected from the group consisting of dioleoylphosphatidylglycerol, dimyristoylphosphatidylglycerol, and pharmaceutically acceptable derivatives, salts and alcoholates thereof.

13. The method according to claim 1, wherein the oligopeptide in said composition comprises solid cyclo-(Arg-Gly-Asp-DPhe-NMeVal) in a polymorphic form having crystallographic unit cell with the lattice parameters: a=9.8±0.1 Å, b=19.5±0.5 Å, and c=15.4±0.1 Å.

14. The method as claimed in claim 1, wherein, the ratio between the amphiphilic compounds and the oligopeptide is in the range between 0.01 and 0.5 or is in the range between 0.001 and 0.05.

15. The method according to claim 1, wherein said cancer is metastatic.

16. The method according to claim 15, wherein said metastases are selected from bone metastases, lung metastases, liver metastases and brain metastases.

17. The method according to claim 1, wherein the cancer is selected from breast cancer, lung cancer, head and neck cancer, prostate cancer, brain cancer, colorectal cancer, liver cancer and malignant melanoma.

18. The method according to claim 17, wherein, the lung cancer is selected from non-small cell carcinoma (NSCLC) and small cell carcinoma (SCLC), the head and neck cancer is squamous cell carcinoma of the head and neck (SCCHN), the liver cancer is hepatocellular carcinoma and/or the brain cancer is selected from astrocytoma, gliblastoma and glioblastoma multiforme.

19. The method according to claim 1, wherein, said patient receives radiotherapy.

20. The method according to claim 1, wherein, said method further comprises administering radiotherapy concurrently or consecutively to said patient.

21. The method according to claim 20, wherein, the radiotherapy is selected from radioimmunotherapy and external beam radiation.

22. The method according to claim 16, wherein, the treatment of the bone metastases comprises or induces:
   a) reduced bone resorption,
   b) new bone formation,
   c) regulation or normalisation of the osteoclast activity,
   d) resumption of bone formation and
   e) regrowth of bone or partial re-growth of the bone,
in said subject.

23. The method according to claim 1, wherein said suspension composition comprises 150 to 300 mg/ml of said oligopeptide.

24. The method according to claim 1, wherein said suspension composition comprises 70% or more of said oligopeptide in the form of solid particles.

25. The method according to claim 1, wherein said suspension composition comprises 150 to 300 mg/ml of said oligopeptide and wherein 70% or more of said oligopeptide is contained in the form of solid particles.

* * * * *